US006416960B1

(12) United States Patent
Bryan

(10) Patent No.: US 6,416,960 B1
(45) Date of Patent: Jul. 9, 2002

(54) DETECTION AND VISUALIZATION OF NEOPLASTIC TISSUES AND OTHER TISSUES

(75) Inventor: Bruce Bryan, Beverly Hills, CA (US)

(73) Assignee: Prolume, Ltd., Pittsburgh, PA (US)

( * ) Notice: Subject to any disclaimer, the term of this patent is extended or adjusted under 35 U.S.C. 154(b) by 0 days.

(21) Appl. No.: 08/908,909

(22) Filed: Aug. 8, 1997

Related U.S. Application Data

(60) Provisional application No. 60/023,374, filed on Aug. 8, 1996.

(51) Int. Cl.$^7$ ............................................. G01N 33/574
(52) U.S. Cl. ................. 435/7.23; 424/133.1; 424/130.1; 424/138.1; 424/141.1
(58) Field of Search ................................ 435/7.23, 7.1, 435/7.2; 424/9.1, 9.6, 130.1, 133.1, 138.1, 141.1, 155.1

(56) References Cited

U.S. PATENT DOCUMENTS

| 3,509,344 A | 4/1970 | Bouwers | 250/83.3 |
|---|---|---|---|
| 3,539,794 A | 11/1970 | Rauhut et al. | 240/2.25 |
| 3,597,877 A | 8/1971 | Speers | 46/116 |
| 3,843,443 A | 10/1974 | Fishman | 195/63 |
| 3,859,125 A | 1/1975 | Miller | 117/155 |
| 3,939,123 A | 2/1976 | Matthews | 260/77.5 |
| 4,006,117 A | 2/1977 | Merrifield et al. | 260/45.9 |

(List continued on next page.)

FOREIGN PATENT DOCUMENTS

| EP | 0226979 | 7/1987 | |
|---|---|---|---|
| EP | 0245093 | 11/1987 | |
| EP | 0252683 | 1/1988 | ........... C07H/21/04 |
| EP | 0386691 | 9/1990 | ........... C12Q/1/68 |
| EP | 0387355 | 9/1990 | |
| EP | 0540064 | 5/1993 | |
| WO | 8603840 | 7/1986 | ......... G01N/33/545 |
| WO | 9215673 | 9/1992 | |
| WO | 9313395 | 7/1993 | |
| WO | 9418342 | 8/1994 | |
| WO | 9507463 | 3/1995 | |
| WO | 9513551 | 5/1995 | |
| WO | 9518853 | 7/1995 | ........... C12N/9/15 |
| WO | 9524930 | 9/1995 | |
| WO | 9525798 | 9/1995 | |
| WO | 9532012 | 11/1995 | |
| WO | 9624406 | 8/1996 | |
| WO | 9631451 | 10/1996 | |
| WO | 9711094 | 3/1997 | |
| WO | 9728261 | 8/1997 | |
| WO | 9729319 | 8/1997 | |
| WO | 9814605 | 4/1998 | |
| WO | 9826277 | 6/1998 | |
| WO | 9849336 | 11/1998 | |
| WO | 9949019 | 9/1999 | |

OTHER PUBLICATIONS

US 5,416,927, 05/1995, Spangrud (withdrawn).
Baldwin et al., "Applications of the cloned bacterial luciferase genes LUXA and LUXB to the study of transcriptional promoters and terminators," *Bioluminescence and Chemiluminescence: Basic Chemistry and Analytical Applications*, DeLuca and McElroy, Eds., Academic Press (1981).
Becvar and Wu, "A thermodynamic explanation for the kinetic differences observed using different chain length aldehydes in the in vitro bacterial bioluminescent reaction," *Bioluminescence and Chemiluminescence: New Perspectives*, J. Schölmerich et al., Eds., John Wiley & Sons (1986).
Chalfie, Green fluorescent protein, *Photochemistry and Photobiology*, 62(4):651–656 (1995).
Database EMBL Nucleotide and Protein Sequences, AC=AF025844, Co–reporter vector pRL–Null, complete sequence, abstract, (1997).
Delagrave et al., Red–shifted excitation mutants of the green fluorescent protein, *Bio/Technology* 13(2):151–154 (1995).
Ehrig et al., Green–fluorescent protein mutants with altered fluorence excitationspectra, *FEBS Letters* 367:163–166 (1995).
Fratamico et al., Contstruction and characterization of *Escherichia coli* 0157:H7 strains expressing firefly luciferase and green fluorescent protein and their use in survival studies, *J of Food Protection* 60(10):1167–1173 (1997).
Grentzmann et al., A dual–luciferase system for studying recoding signals, *RNA* 479–486 (1998).
Heim et al., Engineering green fluorescent protein for improved brightness, longer wavelengths and fluorescence resonance energy transfer, *Current Biology* 6(2):178–182 (1996).
Mitra et al., Fluorescence resonance energy tranfer between blue–emitting and red–shifted excitation derivatives of the green fluorescent protein, *Gene* 73(1):13–17 (1996).

(List continued on next page.)

*Primary Examiner*—Sheela Huff
(74) *Attorney, Agent, or Firm*—Stephanie L. Seidman; Heller Ehrman White & McAuliffe LLP

(57) ABSTRACT

Diagnostic systems that rely on bioluminescence for visualizing tissues in situ are provided. The systems are particularly useful for visualizing and detecting neoplastic tissue and specialty tissue during surgical procedures. Kits that provide the components of the systems and methods using the systems for visualizing the tissue are also provided. The systems include compositions containing conjugates that include a tissue specific, particularly a tumor-specific, targeting agent linked to a targeted agent, a luciferase or luciferin. The systems also include a second composition that contains the remaining components of a bioluminescence generating reaction. Administration of the compositions results production of light by targeted tissues that permits the detection and localization of neoplastic tissue for surgical removal. Therapeutic methods in which photosensitizing compounds are administered are also provided.

89 Claims, No Drawings

U.S. PATENT DOCUMENTS

| | | | |
|---|---|---|---|
| 4,016,880 A | 4/1977 | Theeuwes et al. .......... 128/260 |
| 4,021,364 A | 5/1977 | Speiser ...................... 252/316 |
| 4,044,126 A | 8/1977 | Cook et al. ................. 424/243 |
| 4,162,355 A | 7/1979 | Tsibris ....................... 526/293 |
| 4,171,412 A | 10/1979 | Ĉoupek et al. ............. 525/329 |
| 4,175,183 A | 11/1979 | Ayers ......................... 536/57 |
| 4,177,038 A | 12/1979 | Biebricher et al. ............ 8/192 |
| 4,178,439 A | 12/1979 | Ayers et al. ................. 536/59 |
| 4,179,402 A | 12/1979 | Kim et al. .................. 252/431 |
| 4,180,524 A | 12/1979 | Reusser et al. ............. 585/644 |
| 4,225,581 A | 9/1980 | Kreuter et al. ............... 424/88 |
| 4,241,537 A | 12/1980 | Wood ........................... 47/77 |
| 4,244,721 A | 1/1981 | Gupta et al. ................... 65/31 |
| 4,269,821 A | 5/1981 | Kreuter ...................... 424/19 |
| 4,281,645 A | 8/1981 | Jobsis ....................... 128/633 |
| 4,282,287 A | 8/1981 | Giese ........................ 428/407 |
| 4,322,311 A | 3/1982 | Lim et al. .................. 252/316 |
| 4,324,683 A | 4/1982 | Lim et al. .................. 252/316 |
| 4,329,332 A | 5/1982 | Couvreur et al. ............. 424/9 |
| 4,364,923 A | 12/1982 | Cook et al. .................. 424/46 |
| 4,414,209 A | 11/1983 | Cook et al. ................. 424/243 |
| 4,438,869 A | 3/1984 | Vierkötter et al. ............ 222/1 |
| 4,439,585 A | 3/1984 | Gould et al. ................ 525/127 |
| 4,449,783 A | 5/1984 | Witte ..................... 350/96.16 |
| 4,478,817 A | 10/1984 | Campbell et al. ............ 424/7.1 |
| 4,485,227 A | 11/1984 | Fox ............................. 528/61 |
| 4,507,230 A | 3/1985 | Tam et al. ................ 260/112.5 |
| 4,512,762 A | 4/1985 | Spears ....................... 604/21 |
| 4,522,811 A | 6/1985 | Eppstein et al. ............... 514/2 |
| 4,523,224 A | 6/1985 | Longacre, Jr. .................. 358/42 |
| 4,525,306 A | 6/1985 | Yajima .................. 260/428.5 |
| 4,528,180 A | 7/1985 | Schaeffer .................... 424/52 |
| 4,542,102 A | 9/1985 | Dattagupta et al. ............. 435/6 |
| 4,562,157 A | 12/1985 | Lowe et al. ................ 435/291 |
| 4,565,647 A | 1/1986 | Llenado .................... 252/354 |
| 4,569,981 A | 2/1986 | Wenzel et al. ................ 528/67 |
| 4,581,335 A | 4/1986 | Baldwin ................. 435/172.3 |
| 4,614,712 A | * | 9/1986 | Baldwin et al. ............... 435/4 |
| 4,629,295 A | 12/1986 | Vogl ......................... 350/503 |
| 4,642,452 A | 2/1987 | Loy ........................... 250/213 |
| 4,665,022 A | * | 5/1987 | Schaeffer et al. .............. 435/7 |
| 4,676,406 A | 6/1987 | Frischmann et al. ........ 222/136 |
| 4,681,870 A | 7/1987 | Balint et al. ................ 502/403 |
| 4,687,663 A | 8/1987 | Schaeffer .................... 424/52 |
| 4,711,659 A | 12/1987 | Moore ......................... 71/93 |
| 4,714,682 A | 12/1987 | Schwartz .................... 436/10 |
| 4,734,939 A | 4/1988 | Copp ........................... 2/422 |
| 4,762,881 A | 8/1988 | Kauer .................... 525/54.11 |
| 4,767,206 A | 8/1988 | Schwartz .................... 356/73 |
| 4,772,948 A | 9/1988 | Tuck .......................... 358/87 |
| 4,774,189 A | 9/1988 | Schwartz .................... 436/10 |
| 4,782,840 A | 11/1988 | Martin, Jr. et al. ......... 128/654 |
| 4,789,633 A | 12/1988 | Huang .................... 435/240.2 |
| 4,798,719 A | 1/1989 | Ballou ....................... 424/1.1 |
| 4,804,403 A | 2/1989 | Moore ........................ 71/28 |
| 4,822,994 A | 4/1989 | Johnson et al. ............. 250/213 |
| 4,849,213 A | 7/1989 | Schaeffer .................... 424/53 |
| 4,853,327 A | 8/1989 | Dattagupta ................... 435/6 |
| 4,861,876 A | 8/1989 | Kessel ....................... 540/145 |
| 4,867,908 A | 9/1989 | Recktenwald et al. ... 252/408.1 |
| 4,882,165 A | 11/1989 | Hunt et al. ................. 424/450 |
| 4,885,250 A | 12/1989 | Eveleigh et al. ............. 435/181 |
| 4,891,043 A | 1/1990 | Zeimer et al. ............... 604/20 |
| 4,895,721 A | 1/1990 | Drucker ..................... 424/53 |
| 4,908,405 A | 3/1990 | Bayer et al. ................ 525/61 |
| 4,921,757 A | 5/1990 | Wheatley et al. ........ 428/402.2 |
| 4,924,358 A | 5/1990 | Von Heck ................... 362/32 |
| 4,927,879 A | 5/1990 | Pidgeon .................. 525/54.1 |
| 4,927,916 A | 5/1990 | Matsueda et al. .............. 424/9 |
| 4,931,498 A | 6/1990 | Pidgeon .................... 525/54.1 |
| 4,938,948 A | 7/1990 | Ring et al. ...................... 424/9 |
| 4,948,210 A | 8/1990 | Simms ...................... 350/1.4 |
| 4,950,588 A | 8/1990 | Dattagupta ..................... 435/6 |
| 4,953,963 A | 9/1990 | Miller ....................... 350/547 |
| 4,954,444 A | 9/1990 | Eveleigh et al. ............. 435/181 |
| 4,961,920 A | 10/1990 | Ward .............................. 424/9 |
| 4,963,368 A | 10/1990 | Antrim et al. ............... 424/498 |
| 4,968,613 A | 11/1990 | Masuda et al. .......... 435/172.3 |
| 4,978,520 A | 12/1990 | Ballou ........................ 424/1.1 |
| 4,999,208 A | 3/1991 | van Lengerrich ........... 426/549 |
| 5,004,565 A | 4/1991 | Schapp ...................... 252/700 |
| 5,023,181 A | 6/1991 | Inouye ....................... 435/189 |
| 5,023,745 A | 6/1991 | Glass ......................... 361/56 |
| 5,029,963 A | 7/1991 | Naselli et al. ........... 350/96.18 |
| 5,038,963 A | 8/1991 | Pettengill et al. ........... 222/145 |
| 5,049,373 A | 9/1991 | Ballou ....................... 424/1.1 |
| 5,059,417 A | 10/1991 | Williams et al. .............. 424/53 |
| 5,067,019 A | 11/1991 | Juday et al. ................ 358/160 |
| 5,068,735 A | 11/1991 | Tuchiya et al. ............. 358/209 |
| 5,084,780 A | 1/1992 | Phillips ...................... 359/350 |
| 5,085,853 A | 2/1992 | Williams et al. .............. 424/53 |
| 5,092,992 A | 3/1992 | Crane et al. .............. 210/198.2 |
| 5,093,240 A | 3/1992 | Inouye et al. ............... 435/69.1 |
| 5,098,828 A | 3/1992 | Geiger et al. .............. 435/7.72 |
| 5,113,077 A | 5/1992 | Shimizu et al. ........ 250/370.11 |
| 5,116,868 A | 5/1992 | Chen et al. ................. 514/546 |
| 5,117,553 A | 6/1992 | Kliman ....................... 29/598 |
| 5,132,101 A | 7/1992 | Vogel et al. ................... 424/9 |
| 5,139,937 A | 8/1992 | Inouye et al. ............... 435/69.1 |
| 5,146,077 A | 9/1992 | Caserta et al. .............. 250/213 |
| 5,148,022 A | 9/1992 | Kawaguchi et al. ........ 250/341 |
| 5,158,349 A | 10/1992 | Holland et al. ............... 362/34 |
| 5,162,227 A | 11/1992 | Cormier ................ 435/252.33 |
| 5,166,065 A | 11/1992 | Williams et al. ......... 435/240.1 |
| 5,177,812 A | 1/1993 | DeMars ......................... 2/199 |
| 5,179,120 A | 1/1993 | Vogel et al. ................. 514/410 |
| 5,182,202 A | 1/1993 | Kajiyama et al. ........... 435/189 |
| 5,188,837 A | 2/1993 | Domb ........................ 424/450 |
| 5,189,029 A | 2/1993 | Boyer et al. .................. 514/64 |
| 5,190,762 A | 3/1993 | Yarosh ....................... 424/450 |
| 5,192,679 A | 3/1993 | Dawson et al. ............. 435/243 |
| 5,196,318 A | 3/1993 | Baldwin et al. ............ 435/69.1 |
| 5,196,524 A | 3/1993 | Gustafson et al. .......... 536/23.2 |
| 5,206,161 A | 4/1993 | Drayna et al. ............... 435/212 |
| 5,212,085 A | 5/1993 | Wands et al. .......... 435/240.27 |
| 5,219,737 A | 6/1993 | Kajiyama et al. ........... 435/69.1 |
| 5,221,623 A | 6/1993 | Legocki et al. ........... 435/252.3 |
| 5,222,797 A | 6/1993 | Holland ....................... 362/34 |
| 5,225,212 A | 7/1993 | Martin ....................... 424/450 |
| 5,229,285 A | 7/1993 | Kajiyama et al. ........... 435/189 |
| 5,272,079 A | 12/1993 | Yarosh ....................... 435/193 |
| 5,277,913 A | 1/1994 | Thompson et al. ......... 424/450 |
| 5,283,122 A | 2/1994 | Huang et al. ............. 428/402.2 |
| 5,283,911 A | 2/1994 | DeMars ..................... 2/209.13 |
| 5,284,646 A | 2/1994 | Menz et al. .................... 424/9 |
| 5,288,623 A | 2/1994 | Zenno et al. ............... 435/69.7 |
| 5,292,658 A | 3/1994 | Cormier et al. ......... 435/252.33 |
| 5,292,814 A | 3/1994 | Bayer et al. ................ 525/243 |
| 5,296,231 A | 3/1994 | Yarosh ....................... 424/450 |
| 5,311,859 A | 5/1994 | Monroe et al. ................ 126/6 |
| 5,313,306 A | 5/1994 | Kuban et al. ................. 348/65 |
| 5,315,628 A | 5/1994 | Guendel ...................... 378/20 |
| 5,323,492 A | 6/1994 | DeMars ..................... 2/203.13 |
| 5,328,603 A | 7/1994 | Velander et al. .......... 210/198.2 |
| 5,330,906 A | 7/1994 | Kajiyama et al. ........... 435/189 |
| 5,331,950 A | 7/1994 | Wood, Sr. ...................... 128/6 |
| 5,334,640 A | 8/1994 | Desai et al. ................. 524/56 |
| 5,337,745 A | 8/1994 | Benaron .................... 128/633 |
| 5,341,538 A | 8/1994 | Banome ................... 15/210.1 |
| 5,342,607 A | 8/1994 | Josephson .................... 424/9 |
| 5,344,928 A | 9/1994 | Masuya et al. ................ 544/37 |

| | | | |
|---|---|---|---|
| 5,346,455 A | 9/1994 | Volkert | 493/335 |
| 5,351,931 A | 10/1994 | Houben et al. | 249/141 |
| 5,352,432 A | 10/1994 | Menz et al. | 424/9 |
| 5,352,448 A | 10/1994 | Bowersock et al. | 424/438 |
| 5,352,598 A | 10/1994 | Kajiyama et al. | 435/189 |
| 5,353,378 A | 10/1994 | Hoffman et al. | 395/2.81 |
| 5,360,010 A | 11/1994 | Applegate | 128/745 |
| 5,360,726 A | 11/1994 | Raikhel | 435/172.3 |
| 5,360,728 A | 11/1994 | Prasher | 435/189 |
| 5,362,865 A | 11/1994 | Austin | 536/24.1 |
| 5,363,984 A | 11/1994 | Laird | 221/24 |
| 5,366,881 A | 11/1994 | Singh et al. | 435/177 |
| 5,368,518 A | 11/1994 | Hitchcock | 446/329 |
| 5,374,534 A | 12/1994 | Zomer et al. | 435/8 |
| 5,374,805 A | 12/1994 | DiFranco | 219/121 |
| 5,381,956 A | 1/1995 | Robinson et al. | 239/22 |
| 5,383,684 A | 1/1995 | Smath | 281/29 |
| 5,387,526 A | 2/1995 | Garner et al. | 436/169 |
| 5,389,033 A | 2/1995 | Rauch | 446/473 |
| 5,389,449 A | 2/1995 | Afeyan et al. | 428/523 |
| 5,390,086 A | 2/1995 | Holland | 362/34 |
| 5,393,580 A | 2/1995 | Ma et al. | 428/29 |
| 5,396,069 A | 3/1995 | Craig et al. | 250/330 |
| 5,396,408 A | 3/1995 | Szczech | 362/397 |
| 5,397,014 A | 3/1995 | Aydt | 220/269 |
| 5,397,609 A | 3/1995 | Chapman | 428/17 |
| 5,398,972 A | 3/1995 | Todaro | 283/67 |
| 5,399,122 A | 3/1995 | Slater | 472/51 |
| 5,400,698 A | 3/1995 | Savage | 99/439 |
| 5,401,773 A | 3/1995 | Noel | 514/547 |
| 5,403,713 A | 4/1995 | Bevilacqua et al. | 435/7.1 |
| 5,403,750 A | 4/1995 | Braatz et al. | 436/531 |
| 5,405,056 A | 4/1995 | Mills | 222/136 |
| 5,405,206 A | 4/1995 | Bedol | 401/7 |
| 5,405,958 A | 4/1995 | VanGermert | 544/71 |
| 5,407,391 A | 4/1995 | Monroe et al. | 472/61 |
| 5,407,691 A | 4/1995 | Przelomski et al. | 426/249 |
| 5,409,900 A | 4/1995 | Vogel et al. | 514/17 |
| 5,410,962 A | 5/1995 | Collier | 101/375 |
| 5,411,427 A | 5/1995 | Nelson et al. | 446/71 |
| 5,411,730 A | 5/1995 | Kirpotin et al. | 424/322 |
| 5,412,085 A | 5/1995 | Allen et al. | 536/24.1 |
| 5,412,118 A | 5/1995 | Vermeer et al. | 549/417 |
| 5,413,098 A | 5/1995 | Benaron | 128/633 |
| 5,413,332 A | 5/1995 | Montgomery | 273/58 |
| 5,413,454 A | 5/1995 | Movesesian | 414/729 |
| 5,416,017 A | 5/1995 | Burton et al. | 435/240.2 |
| 5,416,193 A | 5/1995 | Desai | 530/334 |
| 5,418,155 A | 5/1995 | Cormier et al. | 435/189 |
| 5,419,558 A | 5/1995 | Jones | 273/153 |
| 5,421,583 A | 6/1995 | Gluck | 273/293 |
| 5,422,266 A | 6/1995 | Cormier et al. | 435/252.3 |
| 5,432,623 A | 7/1995 | Egan et al. | 359/15 |
| 5,433,896 A | 7/1995 | Kang et al. | 252/700 |
| 5,435,010 A | 7/1995 | May | 2/67 |
| 5,435,787 A | 7/1995 | Ratcliffe | 472/57 |
| 5,439,797 A | 8/1995 | Tsien et al. | 435/7.21 |
| 5,441,867 A | 8/1995 | Garman et al. | 435/6 |
| 5,446,157 A | 8/1995 | Morgan et al. | 546/13 |
| 5,451,683 A | 9/1995 | Barrett et al. | 548/302.7 |
| 5,455,357 A | 10/1995 | Herrmann et al. | 548/147 |
| 5,458,931 A | 10/1995 | Mankes | 428/14 |
| 5,460,022 A | 10/1995 | Parsons | 70/456 |
| 5,468,468 A | 11/1995 | LaRochelle et al. | 424/1.49 |
| 5,470,881 A | 11/1995 | Charlton et al. | 514/588 |
| 5,478,490 A | 12/1995 | Russo et al. | 252/153 |
| 5,478,501 A | 12/1995 | Rau | 252/547 |
| 5,482,719 A | 1/1996 | Guillet et al. | 424/486 |
| 5,484,589 A | 1/1996 | Salganik | 424/94.2 |
| 5,484,723 A | 1/1996 | Zenno et al. | 435/189 |
| 5,486,161 A | 1/1996 | Lax et al. | 604/22 |
| 5,486,455 A | 1/1996 | Stults | 435/6 |
| 5,491,084 A | 2/1996 | Chalfie et al. | 435/189 |
| 5,511,564 A | 4/1996 | Wilk | 128/898 |
| 5,532,171 A | 7/1996 | Motsenbocker | 436/533 |
| 5,533,082 A | 7/1996 | Gronemeyer | 378/20 |
| 5,535,053 A | 7/1996 | Baril et al. | 359/409 |
| 5,536,382 A | 7/1996 | Sunzeri | 204/451 |
| 5,540,649 A | 7/1996 | Bonnell et al. | 600/114 |
| 5,547,486 A | 8/1996 | Detrick et al. | 71/28 |
| 5,553,853 A | 9/1996 | Sackitey | 273/236 |
| 5,569,588 A | 10/1996 | Ashby et al. | 435/6 |
| 5,575,288 A | 11/1996 | Sliwa, Jr. et al. | 128/660.09 |
| 5,604,123 A | 2/1997 | Kazami et al. | 435/189 |
| 5,612,474 A | 3/1997 | Patel | 536/27.14 |
| 5,619,995 A | 4/1997 | Lobodzinski | 128/653.1 |
| 5,619,999 A | 4/1997 | Von Behren et al. | 128/661.01 |
| 5,622,172 A | 4/1997 | Li et al. | 128/660.04 |
| 5,625,048 A | 4/1997 | Tsien et al. | 536/23.4 |
| 5,630,426 A | 5/1997 | Eggers et al. | 128/734 |
| 5,637,463 A | 6/1997 | Dalton et al. | 435/6 |
| 5,650,135 A | 7/1997 | Contag et al. | 424/9.1 |
| 5,686,578 A | * 11/1997 | Goldenberg | 530/387.3 |
| 5,688,657 A | * 11/1997 | Tsang et al. | 435/7.23 |
| 5,741,668 A | 4/1998 | Ward et al. | 435/69.1 |
| 5,747,338 A | 5/1998 | Giese et al. | 435/348 |
| 5,770,371 A | 6/1998 | Thompson | 435/6 |
| 5,776,681 A | 7/1998 | Virta et al. | 435/6 |
| 5,777,079 A | 7/1998 | Tsien et al. | 530/350 |
| 5,792,456 A | * 8/1998 | Yelton et al. | 424/133.1 |
| 5,795,737 A | 8/1998 | Seed et al. | 435/69.1 |
| 5,804,387 A | 9/1998 | Cormack et al. | 435/6 |
| 5,876,995 A | 3/1999 | Bryan | 435/189 |

OTHER PUBLICATIONS

Romoser et al., Detection in living cells of Ca2+–dependent changes in the fluorescence emission of an indicator composed of two green fluorescent protein variants liked by a calmodulin–binding sequence, *J. of Biolog. Chem.* 272(20):13270–13274 (1997).

Sandalova, Some notions about structure of bacterial luciferase, obtained by analysis of amino acid sequence, and study of monoclonal antibodies binding, In *Biological Luminescence, Proceedings of International School*, 1st, ed., Jezowska–Trzebiatowska et al., World Science (1990).

Sherf et al., Dual–luciferase reporter assay: an advanced co–reporter technology integrating firefly and *Renilla* luciferase assays, *Promega Notes* 57:2–5 (1996) downloaded from the Promega website at http://www.promega.com.

Spurlok et al., A fine structure study of the anthocodium in *Renilla mulleri*, *J. of Cell Biology* 64:15–28 (1975).

Xu et al., A bioluminescence resonance energy transfer (BRET) system: application ot interacting circadian clock proteins, *Proceedings of the National Academy of Sciences of the United States of America*, 9(1):151–156, abstract (1999).

Arai M. et al., "Detection of tumor associated antigen, PA8–15, in sera from pancreatic and gastrointestinal carcinoma patients", *Jpn. J. Clin. Oncol.* 20:145–153 (1990).

Ballesta et al., "Carcinoembryonic antigen in staging and follow–up of patients with solid tumors", *Tumor Biol.* 16:32–41 (1995).

Ballou et al., "Tumor labeling in vivo using Cy5–monoclonal antibody", *Proc. Am. Assoc. Canc. Res.* 35:504, Abstract #3005, (1994).

Behr et al., "Factors influencing the pharmacokinetics, dosimetry, and diagnositic accuracy of radioimmunodetection and radioimmunotherapy of carcinoembryonic antigen–expressing tumors", *Cancer Research* 56:1805–1816 (1996).

Brezicka and Olling, "L3p40–50—A new lung–tumor–associated 40– to 50–kDa antigen defined by a monoclonal antibody (L3)", *Int. J. Cancer Suppl.* 8:121–124 (1994).

Childress, "Oxygen minimum layer: Vertical distribution and respiration of the mysid gnathophausia ingens", *Science* 160:1242–1243 (1968).

Cohn et al. "Cloning of the *Vibrio harveyi* luciferase genes: use of a synthetic oligonucleotide probe", *Proc. Natl. Acad. Sci. U.S.A.* 80(1):120–123 (1983).

Cole et al., "Characterization of the functional specificity of a cloned t–cell receptor heterodimer recognized the MART–1 melanoma antigen", *Cancer Research* 55:748–752 (1995).

Derwent #008580311 WPI Acc. No. 91–084343/199112 (citing, Japanese Patent Application No. JP 3030678 published Feb. 8, 1991).

Derwent #010423635 WPI Acc. No. 95–324955/199542 (citing, Japanese Patent Application No. JP 7222590, published Aug. 22, 1995).

Derwent #007778737 WPI Acc. No. 89–043849/198906 (citing, Japanese Patent Application No. JP 63317079, published Dec. 26, 1988).

Derwent #009227258 WPI Acc. No. 92–354680/199243 (citing, Japanese Patent Application No. JP 4258288, published Sep. 14, 1993).

Finn, "Pancreatic tumor antigens: Diagnostics markers and targets of immunotherapy", *Important Advances in Oncology*, pp. 61–77 (1992).

Fredman, "Glycosphigolipid tumor antigens", *Adv. Lipid Res.* 25:213–234 (1993).

Greenberg et al., "Prostate cancer in a trangentic mouse", *Proc. Natl. Acad. Sci. USA* 92:3439–3443 (1995).

Hart et al., "*Renilla reniformis* bioluminescence: Luciferase– catalyzed production of nonradiating excited states from luciferin analogues and elucidation of the excited state species involved in energy transfer to Renilla green fluorescent protein", (1979) *Biochemistry* 18:2204–2210 (1979).

*Bioluminescence and Chemiluminescence. Basic Chemistry and Analytical Applications*, DeLuca et al., eds., Academic Press (1981) Table of Contents.

Hazum et al., A photocleavable protecting group for the thiol function of cysteine, *Pept., Proc. Eur. Pept. Symp.*, 16th, Brunfeldt, K (Ed) pp. 105–110 (1981).

Hellström and Hellström, "Oncogene–associated tumor antigens as targets for immunotherapy", *FASEB* 3(6):1715–1722 (1989).

*Immobilized Biochemicals and Affinity Chromatography*, Advances in Experimental Medicine and Biology, vol. 42, ed. R. Dunlap, Plenum Press, N.Y. (1974) Table of Contents.

Inoue et al., "Squid bioluminescence II. Isolation from *Watasenia scintillans* and synthesis of 2–(p–hydroxybenzyl)–6–(p–hydroxyphenyl)–3,7–dihydroimidazo[1,2–a]pyrazin–3–one", *Jap. Soc. Chem. Lett.* 141–144 (1975).

Johnson et la., "Compartmentalization of algal bioluminescence: autofluorescence of bioluminescent particles in the dinoflagellate Gonyoulax as studied with image–intensified video microscopy and flow cytometry", *J. Cell. Biol.* 100(5):1435–1446 (1985).

Juweid et al., "Improved detection of medullary thyroid cancer with radiolabeled antibodies to carcinoembryonic antigen", *J. Clin. Oncol.* 14(4):1209–1217 (1996).

Kamigaki et al., "Improved tumor detection by anti–cea chimeric Fab oligomers with disulfied linkages in a pancreatic–carcinoma–xenograft model", *Int. J. Cancer* 66:261–267 (1996).

Karsten et al., "A new monoclonal antibody (A78–G/A7) to the Thomsen–Friedenreich pan tumor antigen", *Hybridoma* 14(1):37–44 (1995).

Kashiwabara et al., "Comparative vasodepressor effects of 3–pyridine derivatives possessing the cyanoamidine or amide structure in pithed rats", *Arch. int. Pharmacodyn.* 328:297–306 (1994).

Kawakami et al., Identification of the Immunodominant Peptides of the MART–1 Human Melanoma Antigen Recognized by the Majority of HLA–A2–restricted Tumor Infiltrating Lymphocytes *J. Exp. Med.* 180:347–352 (1994).

Kennedy and Cabral, Immobilized Enzymes, in *Solid Phase Biochemistry, Analytical and Synthetic Aspects*, Scouten, Ed., 7:253–391 (1983).

Lai et al., "CYFRA 21–1 enzyme–linked immunosorbent assay: Evaluation as a tumor marker in non–small cell lung cancer", *CHEST* 109:995–1000 (1996).

*Liposome Technology, Targeted Drug Delivery and Biological Interaction*, vol. III, G. Gregoriadis (ed.), CRC Press, Inc. (1984) Table of Contents.

Lloyd, "Tumor antigens known to be immunogenic in man", *Ann. N.Y. Acad. Sci.*, 690:50–57 (1993).

Maroulakou et al., "Prostate and mammary adenocarcinoma in transgenic mice carrying a rat C3(1) simian virus 40 large tumor antigen fusion gene", *Proc. Natl. Acad. Sci. USA* 91:11236–11240 (1994).

Metze et al., "Expression of a glycoprotein of the carcinoembryonic antigen family in normal and neoplastic sebaceous glands", *J. Am. Acad. Dermatol.* 34:735–744 (1996).

Murkherji and Chakraborty, "Immunobiology and immunotherapy of melanoma", *Curr. Opin. Oncol.* 7:175–184 (1995).

Müller and Campbell, "The chromophore of pholasin: A highly luminescent protein", *J. Biolumin. Chemilum.* 5:25–30 (1990).

Neville, "Detection of tumor antigens with monoclonal antibodies: immunopathology and immunodiagnosis", *Curr. Opin. Immunol.* 3(5):674–678 (1991).

Niklinski and Furman, "Clinical tumour markers in lung cancer", *Europ. J. Canc. Prevent.* 4:129–138 (1995).

Nogrady, *Medicinal Chemistry A Biological Approach*, Oxford University Press, New York pp. 388–392 (1985).

Pèlegrin et al., "Antibody–fluorescein conjugates for photoimmunodiagnosis of human colon carcinoma in nude mice", *Cancer* 67:2529–2537 (1991).

Percivale et al., "Radioimmunoguided surgery after primary treatment of locally advanced breast cancer", *J. Clin. Oncol.* 14(5):1599–1603 (1996).

*PIERCE Catalog & Handbook*, pp. 090–0110, T155–T200 (1994).

Rokkones et al., Microinjection and expression of a mouse metallothionein human growth hormone fusion gene in fertilized salmonid eggs, *J. Comp. Phyiol.B* 158:751–758 (1989).

Romero et al., "Multiple specificities in the repertoire of a melanoma patients's cytolytic T lymphocytes directed against tumor antigen MAGE–1.A1", *J. Exp. Med.* 182:1091–1028 (1995).

Rowland et al., "Antitumor properties of vindesine–monoclonal antibody conjugates", *Cancer Immunol. Immunother.* 19:1–7 (1985).

Shimomura, "Cause of spectral variation in the luminescence of semisynthetic aequorins", *Biochem J.* 306:537–543 (1995).

Smalley et al., "Localization of fluorescent compounds in the firefly light organ", *J. Histochem. Cytochem.* 28(4):323–329 (1980).

Smith et al., Kinetically inert Co(III) linkage through an engineered metal binding site: specific orientation of recombinant human papillomavirus type 16 E7 protein on a solid support, *Methods: A Companion to Methods in Enzymology*, 4: 73–78, (1992).

Srivastana, "Protein tumor antigens", *Curr. Opin. Immunol.* 3(5):654–658 (1991).

Stephens et al., "Comprehensive pharmacokinetics of a humanized antibody and analysis of residual anti–idiotypic responses", *Immunology* 85:668–674 (1995).

Sung et al., "Humanized anti–Lewis Y antibodies: In Vitro properties and pharmakokinetics in rhesus monkeys", *Cancer Research* 56:1118–1125 (1996).

Tjoa et al., "Presentation of prostate tumor antigens by dendritic cells stimulates T–cell proliferation and cytotoxicity", *The Prostate* 28:65–69 (1996).

Wang et al., "Utilization of an alternative open reading frame of a normal gene in generating a novel human cancer antigen", *J. Exp. Med.* 183:1131–1140 (1996).

Watson et al. *Molecular Biology of the Gene* 4th Edition, The Benjamin/Cummings Pub. Co., p. 224–225 (1987).

Welches and Baldwin, "Active center studies on bacterial luciferase: Modification of the enzyme with 2,4–dinitrofluorobenzene", *Biochem.* 20: 512–517 (1981).

Widder et al., "Far red bioluminescence from two deep–sea fishes", *Science* 225:512–514 (1984).

Wiels et al., "Monoclonal antibody against a Burkitt lymphoma–associated antigen", *Proc Natl Acad. Sci. U.S.A.* 78:6485–6488 (1981).

Wright and Cox, "Monoclonal antibodies to human tumor antigens", *Curr. Topics Pathol.*, 77:1–18 (1987).

Yamaguchi et al. "Cell–surface antigens of melanoma recognized by human monoclonal antibodies", *Proc. Natl. Sci. U.S.A.* 84:2416–2420 (1987).

Yuan S. et al. "Human pancreatic cancer–associated antigens detected by murine monoclonal antibodies", *Cancer Res.* 45:6179 (1985).

"Aqualite®. A calcium–triggered photoprotein," *SeaLite Sciences Technical Report No. 3* (1994).

Assil et al., Sustained release of the antimetabolite cytarabine in the eye multivesicular liposomes, *Arch. Opthalmol.* 105:400–403 (1987).

Baldwin et al., Cloning of the luciferase structural genes from *Vibro harveyi* and expression of bioluminescene in *Escherichia coli*, *Biochemistry* 23: 3663–3667 (1984).

Batra et al., Insertion of constant region domains of human $IgG_1$ Into CD4–PE40 increases its plasma half–life, *Mol. Immunol.* 30 : 379–386 (1993).

Belas et al., Bacterial bioluminescene: Isolation and expression of the luciferase genes from *Vibrio harveyi*, *Science* 218: 791–793 (1982).

Berg et al., Long–chain polystyrene–grafted polyethylene film matrix: a new support for solid–phase peptide synthesis, *J. Am. Chem. Soc. 111*: 8026–8027 (1989).

Berg et al., Polystyrene–grafted polyethylene: Design of film and felt matrices for solid–phase peptide synthesis, *Innovation Perspect. Solid Phase Synth. Collect. Pap., Int. Symp.*, 1st, Epton (ed.), pp. 453–459 (1990).

Berg et al., Peptide synthesis on polystyrene–grafted polyethylene sheets, *Pept., Proc. Eur. Pept. Symp.*, 20th, Jung et al. (Eds.), pp. 196–198 (1989).

Blinks et al., Multiple forms of the calcium–sensitive bioluminescent protein aequorin, *Fed. Proc.* 1435: 474 (1975).

Bunnin et al. The combinatorial synthesis and chemical and biological evaluation of a 1,4–benzodiazepine library, *Proc. Natl. Acad. Sci. USA*, 91:4708–4712 (1994).

Butz et al., Immunization and affinity purification of antibodies using resin–immobilized lysine–branced synthetic peptides, *Peptide Res.* 7: 20–23 (1994).

Charbonneau et al., "Amino acid sequence of the calcium–dependent photoprotein aequorin," *Biochem.* 24:6762–6771 (1985).

Cohn et al., Nucleotide sequence of the luxa gene of *Vibrio harveyi* and the complete amino acid sequence of the α subunit of bacterial luciferase, *J. Biol. Chem.* 260: 6139–6146 (1985).

Cormier et al., Evidence for similar biochemical requirements for bioluminescene among the colenterates, *J. Cell Physiol.* 81: 291–298 (1972).

de Wet et al., "Cloning of firefly luciferase cDNA and the expression of active luciferase in *Escherichia coli*," *Proc. Natl. Acad. Sci. USA* 82:7870–7873 (1985).

de Wet et al., "Cloning firefly luciferase," *Meth. Enzymol.* 133:311 (1986).

DeWitt et al., Diversomers: an approach to nonpeptide, nonoligomeric chemical diversity, *Proc. Natl. Acad. Sci. USA 90*: 6909–6913 (1993).

Düzgunes et al., Fusion of phospholipid vesicles induced by divalent cations and protons; modulation by phase transitions, free fatty acids, monovalent cations, and polyamines, *Cell Fusion, Ch. 11 Divalent Cations and Protons*, Sowers, A.E. (ed.) pp. 241–267 (1984).

Eichler et al., Identification of substrate–analog trypsin inhibitors through the screening of synthetic peptide combinatorial libraries, *Biochemistry* 32: 11035–11041 (1993).

Ellens et al., pH–induced Destabilization of phosphatidylethanolamine–containing liposomes: Role of bilayer contact, *Biochemistry*, 23: 1532–1538 (1984).

Engebrecht et al., Bacterial bioluminescence: Isolation and genetic analysis of functions from *Vibrio fischeri*, *Cell 32*: 773–781 (1983).

Engebrecht et al., Identification of genes and gene products necessary for bacterial bioluminescene, *Proc. Natl. Acad. Sci. USA 81*: 4154–4158 (1984).

Engebrecht et al., "Techniques for cloning and analyzing bioluminescence genes from marine bacteria," *Meth. Enzymol. 133*:83–99, 234 (1986).

Frackman et al., "Cloning, organization, and expression of the bioluminescence genes of *Xenorhabdus luminescens*," *J. Bacteriol.* 127(10):5767–5773 (1990).

Gesztes et al., Topical anesthesia of the skin by liposome–encapsulated tetracaine, *Anesthesia Analg.* 67: 1079–1081 (1988).

Goldmacher et al., Photoactivation of toxin conjugates, *Bioconj. Chem.* 3:104–107 (1992).

Hart et al., *Renilla reniformis* bioluminescence: luciferase–catalyzed production of nonradiating excited states from luciferin analogues and elucidation of the excited states species involved in energy transfer to Renilla green fluorescent protein, *Biochemistry 18:* 2204–2210, (1979).

Hastings, Bioluminescence, in *Cell Physiol.: Source Book*, Sperelakis, ed., pp. 665–681, Academic Press (1995).

Hermanson et al., *Immobilized Affinity Ligand Techniques*, Chaps. 1 and 2, Academic Press, Inc. (1992).

Hori et al., Renilla luciferin as the substrate for calcium induced photoprotein bioluminescence. Assignment of luciferin plutomers in aequorin and mnemiopsin, *Biochemistry 14:* 2371–2376, (1975).

Hori et al., Structure of native *Renilla reniformis* luciferin, *Proc. Natl. Acad. Sci. USA 74:* 4285–4287 (1977).

*Immobilized Enzyme, Antigens, Antibodies and Peptides. Preparation and Characterization*, Marcel Dekker, Inc., N.Y., Howard H. Weetall (ed.) (1975).

Inouye et al., "Cloning and sequence analysis of cDNA for the luminescent protein aequorin," *Proc. Natl. Acad. Sci. USA* 82:3154–3158 (1985).

Inouye et al., "Expression of apoaequorin complementary DNA in *Escherichia coli*," *Biochem.* 25:8425–8429 (1986).

Inouye et al., "Overexpression and purification of the recombinant $Ca^{2+}$—binding protein, apoaequorin," *J. Biochem.* 105(3):473–477 (1989).

Inouye et al., "Imaging of luciferase secretion from transformed Chinese hamster ovary cells," *Proc. Natl. Acad. Sci. USA* 89:9584–9587 (1992).

Johnson et al., "Introduction to the Cypridina system," *Methods in Enzymology. Bioluminescence and Chemiluminescence.* 57:331–349 (1978).

Kent et al., Preparation and properties of tert–butyloxcarbonylaminocayl–4–(oxymethyl) phenylacetamidomethyl–(Kel F–g–styrene) resin, an insoluble, non–crosslinked support for solid phase peptide synthesis, *Israel J. Chem.* 17: 243–247 (1978).

Kim et al., Preparation of multivesicular liposomes, *Biochim. Biophys. Acta.* 728: 339–34 (1983).

Kleine et al., Lipopeptide–polyoxyethylene conjugates as mitogens and adjuvants, *Immunobiology* 190: 53–66 (1994).

Koch et al., The oxidative cleavability of protein cross–linking reagents containing organoselenium bridges, *Bioconj. Chem.* 1: 296–304 (1990).

Kohama et al., Molecular weight of the photoprotein aequorin, *Biochemistry* 10 : 4149–4152 (1971).

Kusumi et al., Liposomes that can be disintegrated by photo–irradiation, *Chemistry Letters* 433–436 (1989).

Leach et al., Commercially available firefly luciferase reagents, in *Methods in Enzymology. Bioluminescence and Chemiluminescence Part B 133:*51–69, Academic Press (1986).

Legocki et al., Bioluminescence in soybean root nodules: Demonstration of a general approach to assay gene expression in vivo by using bacterial luciferase, *Proc. Natl. Acad. Sci. USA 81:* 9080–9084 (1986).

Lorenz et al., Isolation and expression of a cDNA encoding *Renilla reniformis* luciferase, *Proc. Natl. Acad. Sci. USA* 88: 4438–4442 (1991).

Matthews et al., Purification and properties of *Renilla reniformis* luciferase, *Biochemistry*, 16: 85–91 (1977).

McElroy et al., The colors of bioluminescence: Role of enzyme and substrate structure, in *Molecular Architecture in Cell Physiology*, pp. 63–80, Hayashi et al., eds., Prentice–Hall, Inc., Englewood Cliffs, NJ (1966).

Merrifield, Solid–phase peptide synthesis. III. An improved synthesis of bradykinin, *Biochemistry* 3(9): 1385–1390 (1964).

Mezei et al., Liposomes—A selective drug delivery system for the topical route of administration, *Life Sci.* 26: 1473–1477 (1980).

Mezei et al., Liposomes—A selective drug delivery system for the topical route of administration: Gel dosage form, *J. Pham. Pharmacol.* 34: 473–474 (1981).

Mitchell et al., Preparation of aminomethyl–polystyrene resin by direct aminomethylation, *Tetra. Lett.*, 42 : 3795–3798 (1976).

Miyamoto et al., Cloning and expression of the genes from the bioluminescent system of marine bacteria, *Meth. Enzymol.* 133:70–81 (1986).

Mosbach, AMP and NAD as 'general ligands', *Affinity Techniques. Enzyme Purification: Part B. Methods in Enzymology*, vol. 34, W. B. Jakoby, et al. (eds.), Acad. Press, N.Y. (1974).

Nicoli et al., Bacterial luciferase: The hydrophobic environment of the reactive sulfhydryl, *J. Biol. Chem.* 249: 2393–2396 (1974).

Patel, Liposomes as a controlled–release system, *Biochem. Soc. Trans.* 13: 513–516 (1985).

Pidgeon, Solid Phase membrane mimetics: Immobilized artificial membranes, *Enzyme Microbiology Technology* 12:149–150 (1990).

Pierce Catalog, pp. T123–T154, 1994.

Prasher et al., Cloning and expression of the cDNA coding for aequorin, a bioluminescent calcium–binding protein, *Biochem. Biophys. Res. Commun.* 126(3):1259–1268 (1985).

Prasher et al., Isolation and expression of a cDNA coding for aequorin, the $Ca^{2+}$—activated photoprotein from *Aequorea victoria*, *Meth. Enzymol.* 133:288–297 (1986).

Prasher et al., Sequence comparisons of complementary DNAs encoding aequorin isotypes, *Biochem.* 26:1326–1332 (1987).

Prasher et al., Primary structure of the *Aequorea victoria* green–fluorescent protein, *Gene* 111:229–233 (1992).

Prendergast et al., Chemical and physical properties of aequorin and the green fluorescent protein isolated from *Aequorea forskålea*, *Biochemistry* 17: 3448–53 (1978).

Senter et al., Novel photocleavable protein crosslinking regents and their use in the preparation of antibody–toxin conjugates, *Protochem. Photobiol.* 42: 231–237 (1985).

Shimomura et al., Extraction, purification and properties of a aequorin, a bioluminescent protein from the luminous hydromedusan, *Aequorea, J. Cell. Comp. Physiol.* 59: 233–238 (1962).

Shimomura et al., Properties of the bioluminescent protein aequorin, *Biochemistry* 8: 3991–3997 (1969).

Shimomura et al., Regeneration of the photoprotein aequorin, *Nature* 256: 236–238 (1975).

Shimomura et al., Resistivity to denaturation of the apoprotein of aequorin and reconstitution of the luminescent photoprotein from the partially denatured apoprotein, *Biochem J. 199*:825–828 (1981).

Smith et al., Bioluminescent immunoassays using streptavidin and biotin conjugates of recombinant aequorin, reprinted from *American Biotechnology Laboratory*, Apr. 1995.

Stephenson et al., Studies on the luminescent response of the $Ca^{2+}$–activated photoprotein, obelin, *Biochim. Biophys. Acta 687*: 65–75 (1981).

Stewart and Young, Laboratory techniques in solid phase peptide synthesis, *Solid Phase Peptide Synthesis*, 2d Ed., Pierce Chemical Co., pp. 53–73 (1984).

Straubinger et al., Endocytosis of liposomes and intracellular fate of encapsulated molecules: Encounter with a low pH compartment after internalization in coated vesicles, *Cell 32*: 1069–1079 (1983).

Straubinger et al., pH–sensitive liposomes mediate cytoplasmic delivery of encapsulated macromolecules, *FEBS Letters 179*: 148–154 (1985).

Sucholeiki, Solid–phase photochemical C-S Bond cleavage of thioethers—A New approach to the solid–phase production of non–peptide molecules, *Tetrahedron Lttrs. 35*:7307 (1994).

Thompson et al., Cloning and expression of cDNA for the luciferase from the marine ostracod *Vargula hilgendorfi xi*, *Proc. Natl. Acad. Sci. USA 86*: 6567–6571 (1989).

Thompson et al., *Vargula hilgendorfii* luciferase: a secreted reporter enzyme for monitoring gene expression in mammalian cells, *Gene 96*:257–262 (1990).

Tsuji et al., Some properties of luciferase from the bioluminescent crustacean, *Cypridina hilgendorfii*, *Biochem. 13(25)*:5204–5209 (1974).

Tsuji, Cypridina luciferin and luciferase, *Meth. Enzymol. 57*:364–372 (1978).

Tsuji et al., Site–specific mutagenesis of the calcium–binding photoprotein aequorin, *Proc. Natl. Acad. Sci. USA 83*:8107–8111 (1986).

Vedejs et al., A method for mild photochemical oxidation: Conversion of phenacyl sulfides into carbonyl compounds, *J. Org. Chem. 49*: 573–575 (1984).

Wang, Solid phase synthesis of protected peptides via photolytic cleavage of the a–methylphenacyl ester anchoring linkage, *J. Org. Chem. 41*: 3258–3261 (1976).

Ward et al., An energy transfer protein in coelenterate bioluminescence, *J. Biol. Chem. 254*: 781–788 (1979).

Ward et al., Extraction of Renilla–type luciferin from the calcium–activated photoproteins aequorin, mnemiopsin, and berovin, *Proc. Natl. Acad. Sci. USA 72*: 2530–2534 (1975).

Welches et al., Active center studies on bacterial luciferase: Modification of the enzyme with 2,4–dinitrofluorobenzene, *Biochemistry 20*: 512–517 (1981).

Wienhausen et al., Luciferases from different species of fireflies are antigenically similar, *Photochem. Photobiol. 42*: 609–611 (1985).

Wohlrab et al., Penetration Kinetics of liposomal hydrocortisone in human skin, *Dermatologica 174*: 18–22 (1987).

Wong, Conjugation of proteins to solid matrices, *Chemisry of Protein Conjugation and Cross Linking*, 12:295–317 (1993).

Yatvin et al., Temperature– and pH–sensitive liposomes for drug targeting, *Meth. Enzymol. 149*: 77–87 (1987).

Yen et al., Synthesis of water–soluble copolymers containing photocleavable bonds, *Makromol. Chemisry 190*: 69–82 (1989).

Derwent #008580311 WPI Acc. No. 91–084343/199112 (citing Japanese Patent Application No. JP 3030678, published Feb. 8, 1991).

Derwent #009443237 WPI Acc. No. 93–136754/199317 (citing Japanese Patent Application No. JP 5064583, published Mar. 19, 1993).

Apt et al., Evolution of phycobiliproteins, *J. Mol. Biol. 248*: 79–96 (1995).

Bondar et al., Cadmium–induced luminescence of recombinant photoprotein obelin, *Biochim. Biophys. Acta 1231*: 29–32 (1995).

Fairchild et al., Oligomeric structure, enzyme kinetics, and substrate specificity of the phycocyanin α subunit phycocyanobilin lyase, *J. Biol. Chem. 269(12)*: 8686–8694 (1994).

Gast et al., Separation of a blue fluorescence protein from bacterial luciferase. Biochem. Biopys. Res. Commun. 80(1): 14–21 (1978).

Glazer, Phycobilisomes: structure and dynamics, *Ann. Rev. Microbiol. 36*: 173–98 (1982).

Houmard et al., Genes encoding core components of the phycobilisome in cyanobacterium *Calothrix sp.* strain PCC 7601: occurrence of a multigene family, *J. Bacteriol. 170(12)*: 5512–5321 (1988).

Illarionov et al., Sequence of the cDNA encoding the $Ca^{2+}$–activated photoprotein obelin from the hydroid poly *Obelia longissima*, *Gene 153*:273–274 (1995).

Inoue et al., Electroporation as a new technique for producing transgenic fish, *Cell Differ. Devel. 29*:123–128 (1990).

Karatani et al., A blue fluorescent protein from a yellow–emitting luminous bacterium, *Photochem. Photobiol. 55(2)*: 293–299 (1992).

Kronick, The use of phycobiliproteins as fluorescent labels in immunoassay, *J. Immunolog. Meth. 92*: 1–13 (1986).

Liu et al., A cyanidium caldarium Allophycocyanin β subunit gene, *Plant Physiol. 103*:293–294 (1993).

O'Day et al., *Aristostomias scintillans* (Malacostiedae): a deep sea fish with visual pigments apparently adapted to its own bioluminescence, *Vision Res. 14*:545–550 (1974).

Ozato et al., Production of transgeniuc fish: introduction and expression of chicken γ–crystalline gene in medaka embryos, *Cell Differ. Devel. 19*:237–244 (1986).

Pilot et al., Cloning and sequencing of the genes encoding the α and β subunits of C–phycocyanin from the cyanobacterium *Agmenellum quadruplicatum*, *Proc. Natl. Acad. Sci. USA 81*: 6983–6987 (1984).

Rizzuto et al., Rapid changes of mitochondrial $Ca^{2+}$ revealed by specifically targeted recombinant aequorin, *Nature 358(6384)*: 325–327 (1992).

Vysotski et al., $Mn^{2+}$–activated luminescence of the photoprotein obelin, *Arch. Bioch. Biophys. 316*:92–93 (1995).

Vysotski et al., Luminescence of $Ca^{2+}$–activated photoprotein obelin initiated by NaOCl and $MnCl_2$, *J. Biolumin. Chemilumin. 8*:301–305 (1993).

Abe et al. The Monoclonal Antibody Directed to Difucosylated Type 2 Chain (Fucα1→2Galβ1→4[Fucα1→3]GlcNAc; Y Determinant) J. Biol. Chem. 258:11793–11797 (1983).

Amato, Race quickens for non–stick blood monitoring technology, *Science 258*:892–893 (1992).

Arridge et al. Reconstruction methods for infra–red absorption imaging *Proc. SPIE 1431*:204–215 (1991).

Arridge et al. The Use of Multiple Data Types in Time–resolved Optical Absorption and Scattering Tomography *Proc. SPIE* 2035:218–229 (1993).

Bakker et al. Melanocyte Lineage–specific Antigen gp100 Is Recognized by Melanoma–derived Tumor–infiltrating Lymphocytes *J. Exp. Med.* 179:1005–1009 (1993).

Ban T. et al. Immunohistological and Immunochemical Characterization of a Novel Pancreatic Cancer–associated Antigen MUSE11 *Cancer Res* 49:7141–7146 (1989).

Bast et al. A Radioimmunoassay Using a Monoclonal Antibody to Monitor the Course of Epithelial Ovarian Cancer *Eng. J. Med.* 309(15):883–887 (1983).

Bayer and Wichek (1980) *The Use of Avidin/Biotin Complex as a Tool in Molecular Biology. Meth. Biochem. Anal.* 26, 1–45.

Benaron et al., Tomographic time–of–flight optical device, *Oxygen Transport to Tissue* 16:207–214, 1994.

Benaron et al., Non–recursive linear algorithms for optical imaging in diffusive media, *Oxygen Transport to Tissue* 16:215–222 1994.

Benaron et al. Optical Time–of Flight and Absorbance Imaging of Biologic Media *Science* 259: 1463–1466 (1993).

Blaszczyk M. et al. Characterization of Lewis Antigens in Normal Colon and Gastrointestinal Adenocarcinomas *Proc. Natl. Acad. Sci. U.S.A.* 82:3552–3556 (1985).

Boel et al. BAGE: a New Gene Encoding an Antigen Recognized on Human Melanomas by Cytolytic T Lymphocytes *Immunity* 2:167–175 (1995).

Bosslet et al. Monoclonal antibodies against epitopes on ganglioside $GD_2$ and its lactones *Cancer Res.* 29:171–178 (1989).

Bosslet K. et al. A monoclonal antibody with binding and ihibiting activity towards human pancreatic carcinoma cells *Cancer Immunol Immunother* 23: 185–191 (1986).

Bremer et al. Characterization of a Glycosphingolipid Antigen Defined by the Monoclonal Antibody MBr1 Expressed in Normal and Neoplastic Epithelial Cells of Human Mammary Gland *J. Biol. Chem.* 259:14773–14777 (1984).

Brockhaus et al. Monoclonal Antibodies Directed against the Sugar Sequence of Lacto–N–fucopentaose III Are Obtained from Mice Immunized with Human Tumors *Arch. Biochem. Biophys.* 217:647–651 (1982).

Brockhaus M. et al. Monoclonal Antibodies Directed against the Human $Le^b$ Blood Group Antigen *J Biol Chem* 256:13223–13225 (1981).

Brodin et al. Mouse monoclonal antibodies with specificity for the melanoma–associated ganglioside disialyllactosylceramide ($G_{D3}$) also react with the structural analogue disialylparagloboside *Biochim. Biophys. Acta.* 837:349–353 (1985).

Brown et al. A monoclonal antibody against human colonic adenoma recognizes difucosylated Type–2 blood–group chains *Biosci. Rep.* 3:163–170 (1983).

Burtin B. et al. Carcinoembryonic Antigen *Scand J Immunol* 8, Suppl.8:27–38 (1978).

Cahan et al. Identification of a human neuroectodermal tumor antigen (OFA–1–2) as ganglioside GD2 *Proc. Natl. Acad. Sci. U.S.A.* 79:7629–7633 (1982).

Carlsson et al. Protein Thiolation and Reversible Protein–Protein Conjugation *Biochem. J.* 173: 723–737 (1978).

Charbonneau et al. $Ca^{2+}$–induced Bioluminescence in *Renilla reniformis* Purification and Characterization of a Calcium–Triggered Luciferin–Binding Protein *J. Biol. Chem.* 254:769–780 (1979).

Chen et al., "Analogous" organic synthesis of small–compound libraries: Validation of combinatorial chemistry in small–molecule synthesis, *J. Am. Chem. Soc.* 116:2661–2662, 1994.

Cheresh et al. O–Acetylation of Disialoganglioside $GD_3$ by Human Melanoma Cells Creates a Unique Antigenic Determinant *Science* 225:844–846 (1984c).

Cheresh et al. A Monoclonal Antibody Recognizes an O–Acylated Sialic Acid in a Human Melanoma–associated Ganglioside *J. Biol. Chem.* 259:7453–7459 (1984b).

Cheresh et al. Biosynthesis and expression of the Disialoganglioside $G_{D2}$, a Relevant Target Antigen on Small Cell Lung Carcinoma for Monoclonal Antibody–mediated Cytolysis *Cancer Res.* 46:5112–5118 (1986a).

Cheung et al. Monclonal Antibodies to a Glycolipid Antigen on Human Neuroblastoma Cells *Cancer Res.* 45:2642–2649 (1995).

Chia et al. Use of Monoclonal Antibodies to a Sialylated $Lewis^x$ and Sialylated $Lewis^a$ for Seriological Tests of Cancer *Cancer Res.* 45:435–437 (1985).

Cormier (1981) "Renilla and Aequorea bioluminescence" in *Bioluminescence and Chemiluminescence*, pp. 225–233.

Cumber et al. Structural Features of the Antibody–A Chain Linkage that Influence the Activity and Stability of Ricin A Chain Immunotoxins *Bioconjugate Chem.* 3:397–401 (1992).

Davidsson et al. Ganglioside Composition in Human Meningiomas *J. Neurochem.* 53:705–709 (1989).

Domenech et al. Identification of an HLA–A11–Restricted Epitope from the Tandem Repeat Domain of the Epithelial Tumor Antigen Mucin *J. Immunol.* 155:4766–4774 (1995).

Dubois et al. An Isolated Enriched Organ–specific Cancer Neoantigen of Human Lung Cancer for Leukocyte Adherence Inhibition Assays *Cancer Res.* 45:2661–2669 (1985).

Embleton et al. Antigenicity and drug susceptibility of human osteogenic sarcoma cells "escaping" a cytotoxi methotrexate–albumin–monoclonal antibody conjugate *Br. J. Cancer* 49:559–565 (1984).

Escribano MJ. et al. Differentiation Antigens in Fetal Human Pancreas Reexpression in Cancer *Int J Cancer* 38:155–160 (1986).

Fattom et al. Comparative Immunogenicity of Conjugates Composed of the *Staphylococcis aureus* Type 8 Capsular Polysaccharide Bound to Carrier Proteins by Adipic Acid Dihydrazide of N–Succinimidyl 1–3–(2–Pyridyldithio) propionate *Infection & Immun.* 60:584–589 (1992).

Fredman et al. Gangliosides in the human glioma cell line U–118 MG grown in culture or as xenografts in nude rats *Biochim Biophys Acta* 1045:239–244 (1990a).

Fredman et al. A New Ganglioside of the Lactotetraose Series GalNAc–3'–isoL$_{M1}$, Detected in Human Meconium(1989) *J. Biol. Chem.* 264(21):12122–12125.

Fredman et al. Characterization of the binding epitope of a monoclonal antibody to sulphatide *Biochem. J.* 251 :17–22 (1988a).

Fredman P. et al. Sialyllactotetraosylceramide, a Ganglioside Marker for Human Malignant Gliomas *J Neurochem* 50:912–919 (1988b).

Fredman P. et al. Binding specificity of monoclonal antibodies to ganglioside, Fuc–G Biochim. Biophys. Acta. 875:316–323 (1986a).

Fredman et al. Potential ganglioside antigens associated with human gliomas *Neurol. Res.* 8:123–126 (1986b).

Fukuda, M. Structures of Glycosphingolipids Isolated from Human Embryonal Carcinoma Cells et al. *J Biol Chem* 261:5145–5153 (1986).

Fukushi, et al. Novel Fucolipids Accumulating in Human Adenocarcinoma *J. Biol. Chem.* 259:10511–10517 (1984b).

Fukushi Y. et al. A Novel Disisaloganlioside (IV$^3$NeuAcIII$^6$NeuAcLc$_4$) of Human Adenocarcinoma and the Monoclonal Antibody (FH9) Defining This Disialosyl Structure *Biochemistry* 25 :2859–2866 (1986).

Fukushi et al. Location and Distribution of Difucoganglioside (VI$^3$NeuAcV$^3$III$^3$Fuc$_2$nLc$_6$) in Normal and Tumor Tissues Defined by its Monoclonal Antibody FH6 *Cancer Res.* 45:3711–3717 (1985).

Fukushi, et al., Novel fucolipids accumulating in human adenocarcinoma, *J. Biol. Chem.* 259:4681:4685, (1984).

Fukushima et al. Characterization of Sialosylated Lewis* as a New Tumor–associated Antigen *Cancer Res.* 44:5279–5285 (1984).

Furukawa et al. A Unique Antigenic Epitope of Human Melanoma is Carried on the Common Melanoma Glycoprotein $_{gp}$95/$_p$97 *J. Exp. Med.* 169:585 (1989).

Furukawa et al. Two Human Monoclonal Antibodies Reacting with the Major Gangliosides of Human Melanomas and Comparison with Corresponding Mouse Monoclonal Antibodies *Cancer Res.* 49:191–196 (1989).

Gelder FB. et al. Purification, Partial Characterization, and Clinical Evaluation of a Pancreatic Oncofetal Antigen *Cancer Res* 38:313 (1978).

Gordon et al. Topographical localization of the C–terminal region of the voltage–dependent sodium channel from *Electrophorus eletricus* using antibodies raised against a synthetic peptide *Proc. Natl. Acad Sci.* 84:308–312 (1987).

Gottfries J. et al. Determination of Gangliosides in Six Human Primary Medulloblastomas *J. Neurochem* 55:1322–1326 (1990).

Haglund C. et al. Tissue expression of the tumour associated antigen CA242 in benign and malignant pancreatic lesions. A comparison with CA 50 and CA 19–9 *Br J Cancer* 60:845–851 (1989).

Hakomori S. and Andrews H. Sphingoglycolipids with Le$^b$ activity, and the co–presnece of Le$^{2-}$, Le$^{b-}$ glycolipids ion human tumor tissue *Biochim Biophys Acta* 202:225–228 (1970).

Hakomori, et al. Novel Fucolipids Accumulating in Human Adenocarcinoma *J. Biol. Chem.* 252:4672–4680 (1984).

He et al. GD3 expression by cultured human tumor cells of neuroectodermal origin *Acta Neuropathol.* 79:317–325 (1989).

Higashi et al. Characterization of N–Glycolylneuraminic Acid–containing Gangliosides as Tumor–associated Hanganutziu–Deicher Antigen in Human Colon Cancer *Cancer Res.* 45:3796–3802 (1985).

Hilditch et al. Poor Results with Technetium–99m (V) DMS and Iodine–131 MIBG in the Imaging of Medullary Thyroid Carcinoma *J. Nucl. Med.* 27:1150–1153 (1986).

Hinoda et al. Detection of Circulating Adenocarcinoma–Associated Antigen in the Sera of Cancer Patients with a Monoclonal Antibody *Jpn. J. Cancer Res.* 76(12):1203–1211 (1985).

Hirabayashi et al. Reactivity of mouse monoclonal antibody M2590 against B16 melanoma cells wit chemically synthesized G$_{M3}$ ganglioside *Bichim. Biophys. Acta* 875:126–128 (1986).

Hiraiwa et al. Accumulation of Highly Acidic Sufated Glycosphingolipids in Human Hepatocellular Carcinoma Defined by a Series of Monoclonal Antibodies *Cancer Res.* 50:2917–2928 (1990).

Hirohashi et al. A Human Monoclonal Antibody Directed to Blood Group in Antigen: Heterohybridoma Between Human Lymphocytes from Regional Lymph Nodes of a Lung Cancer patient and Mouse Myeloma *J. Immunol.* 136(11):4163–4168 (1986).

Irie et al. Human antibody to OFA–I, a tumor antigen, produced in vitro by Epstein–Barr virus–transformed human B–lymphoid cell lines *Proc. Natl. Acad. Sci. U.S.A.* 79:5666–5670 (1982).

Juweid et al. Clinical Evaluation of Tumor Targeting with the Anticarcinoembryonic Antigen Murine Monoclonal Antibody Fragment, MN–14 F(ab)$_2$ *Cancer* 78(1):157–168 (1996).

Kawai et al. Quantitative Determination of N–Glycolylneuramini Acid Expression in Human Cancerous Tissues and Avain Lymphoma Cell Lines as a Tumor–associated Sialic Acid by Gas Chromatography–Mass Spectrometry *Cancer Res.* 51:1242–1246 (1991).

Kawakaii et al. Identification of the Immunodominant Peptides of the MART–1 Human Melanoma Antigen Recognized by the Majority of HLA–A2–restricted TumorInfiltrating Lymphocytes *J. Exp. Med.* 180:347 (1994).

Kiguchi et al. Glycosphingolipids of Various Human Ovarian Tumors: A Significantly High Expression of I$^3$SO$_3$GalCer and Lewis Antigen in Mucinous *Cancer Res.* 52:416–421 (1992).

Koizumi et al. Immunoscintigraphy and Pharmacokinetics of Indium–111–labeled ZME–018 Monoclonal Antibody in Patients with Malignant Melanoma *Jpn. J. Cancer Res.* 79:973–981 (1988).

Kondo et al. A Single Retroviral Gag Precursor Signal Peptide Recognized by FBL–3 Tumor–Specific Cytotoxic T Lymphocytes *J. Viol.* 69:6735–6741 (1995).

Koprowski et al. Colorectal Carcinoma Antigens Detected by Hybridoma Antibodies *Somatic Cell Genet* 5:957–972 (1979).

Lan, M. S. et al. Molecular Characterization of a Mucin–type Antigen Associated with Human Pancreatic Cancer *J. Biol. Chem.* 262:12863 (1997).

Lindholm, L. et al. Monoclonal Antibodies against Gastrointestinal Tumour–Associated Antigens Isolated as Monosialogangliosides *Int Arch Allergy Appl Immunol* 71:178 (1992).

Linnebach et al. Sequence investigation of the major gastrointestinal tumor–associated antigen gene family, GA733 *PNAS* 86:27–31 (1989).

Lloyd et al. Mouse Monoclonal Antibody F–3 Recognized the Difucosyl Type–2 Blood Group Structure *Immunogenetics* (N.Y.) 17:537–541 (1983).

Longee et al. Disialoganglioside GD2 in human neuroectodermal tumor cell lines and gliomas *Acta Neuropathol.* 82:45–54 (1991).

Magnani et al. A Monoclonal Antibody–defined Antigen Associated with Gastrointestinal Cancer Is a Ganglioside Containing Sialylated Lacto–N–fucopentaose II* *J. Biol. Chem.* 257:14365–14369 (1982).

Mahan et al. Phase Change Enzyme Immunoassay *Anal. Biochem* 162:163–170 (1987).

Mansson et al. Chemical structure of carcinoma ganglioside antigens defined by monoclonal antibody C–50 and some allied gangliosides of human pancreatic adenocarcinoma *Biochim. Biophys. Acta* 834:110–117 (1985).

Martensson S. et al. A Carbohydrate Epitope Associated with Human Squamous Lung Cancer *Cancer Res.* 48:2125–2131 (1988).

Masui et al. Mechanism of Antitumor Activity in Mice for Anti–Epidermal Growth Factor Receptor Monoclonal Antibodies with Different Isotypes *Cancer Res.* 46:5592 (1986).

Menard et al. Generation of Monoclonal Antibodies Reacting with Normal and Cancer Cells of Human Breast *Cancer Res.* 43:1295–1300 (1983).

Mengeling et al., A microplate assay for analysis of solution–phase glycosyltransferase reactions: Determination of kinetic constants, *Anal. Biochem.* 199:286–292 (1991).

Metzgar et al. Detection of pancreatic cancer–associated antigen (DU–PAN–2 antigen) in serum and ascites of patients with adenocarcinoma *PNAS* 81:5245 (1984).

Mitchell et al. A New Synthetic Route to tert–Butyloxycarbonylaminoacyl1–4–(oxymethyl)phenyl-acetamidomethyl–resin, an Improved Support for Solid-–Phase Peptide Synthesis *J. Org. Chem.* 43: 2845–2852 (1978).

Miyake et al. The Abnormal Occurrence and the Differentiation–Dependent Distribution of N–Acetyl and N–Glycolyl Species of the Ganglioside $GM_2$ in Human Germ Cell Tumors *Cancer* (Philadelphia) 65:499–505 (1990).

Molthoff et al. Comparisons of the pharmacokinetics, biodistribution and dosimetry of monoclonal antibodies OC125, Ov–TL 3, and 139H2 as IgG and $F(ab')_2$ fragments in experimental ovarian cancer *Br. J. Cancer* 65:677–683 (1992).

Myoga et al. Detection of Patients with Cancer by Monoclonal Antibody Directed to Lactoneotetraosylceramide (Paragloboside) *Cancer Res.* 48:1512–1516 (1988).

Nataoli et al. A Murine Monoclonal Antibody Detecting N–Acetyl– and N–Glycolyl–$G_{M2}$: Characterization of Cell Surface Reactivity *Cancer Res.* 46:4116–4120 (1986).

Nilsson et al. Monoclonal antibodies raised against NeuAcα2–6neolactotetraosylceramide detect carcinoma–associated gangliosides *Biochim. Biophys. Acta* 835:577–583 (1985b).

Nilsson et al. Detection of a Ganglioside Antigen Associated with Small Cell Lung Carcinomas Using Monoclonal Antibodies Directed against Fucosyl–GM1[1] *Cancer Res.* 46:1403–1407 (1986).

Nilsson et al. Sialosyllactotetraosylceramide, a novel ganglioside antigen detected in human carcinomas by a monoclonal antibody *FEBS Letters* 182(2)398–402 (1985).

Nudelman et al. Novel Fucolipids of Hukman Adenocarcinoma: Disialosyl Le$^a$ Antigen (III[4]FucIII[6]NeuAcIV[3]NeuAcLa$_4$) of Human Colonic Adenocarcinoma and the Monoclonal Antibody (FH7) Defining This Structure *J. Biol. Chem.* 261:5487–5495 (1986).

Nudelman et al. Characterization of a Human Melanoma–associated Ganglioside Antigen Defined by a Monoclonal Antibody, 4.2 *J. Biol. Chem.* 257: 12752–12756 (1982).

Padwa et al. Photoelimination of a β–Keto Sulfide with a Low–Lyingπ–π* Triple State *J. Org. Chem.* 36(23):3550–3552 (1971).

Paterson et al. A Radioimunoassay for the Detection of a Human Tumor–Associated Glycoprotein (TAG–72) Using Monoclonal Antibody B72.3 *Int. J. Cancer* 37:659–666 (1986).

Pant et al. Production of Monoclonal Antibody SP–21 to Colon–Ovarian Tumor Antigen, COTA *Hybridoma* 5:129–135 (1986).

Powers et al. Protein Purification by Affinity Binding to Unilamellar Vesicles Biotechnol. *Bioeng.* 33:173–182 (1989).

Prall et al. CD66a (BGP), an Adhesion Molecule of the Carcinoembryonic Antigen Family, Is Expressed in Epithelium, Endothelium, and Myeloid Cells in a Wide Range of Normal Human Tissues *J. Histochem. Cytochem* 44:35–41 (1996).

Prat, M. et al. Biochemical and Immunological Properties of the Human Carcinoma–associated CAR–3 Epitope Defined by the Monoclonal Antibody AR–3 *Cancer Res.* 49:1415–1421 (1989).

Primus et al. Immunological Heterogeneity of Carcinoembryonic Antigen: Antigenic Determinants on Carcinoembryonic Antigen Distinguished by Monoclonal Antibodies *Cancer Res.* 43:686–692 (1983).

Pukel et al. $G_{D3}$ A Prominent Ganglioside of Human Melanoma *J. Exp. Med.* 155:1133–1147 (1982).

Rettig G. et al. High–Molecular–Weight Glycoproteins of Human Teratocarcinoma Defined by Monoclonal Antibodies to Carbohydrate Determinants *Cancer Res.* 45:815–821 (1985).

Rose et al. Primary structure of the human melanoma–associated antigen p97 (melanotransferin) deduced from the mRNA sequence *PNAS* 83:1261–1265 (1986).

Russo et al. Expressions of the MAGE Gene Family in Primary and Metastatic Human Breast Cancer: Implications for Tumor Antigen–Specific Immunotherapy *Int. J. Cancer P. Oncol.* 64:216–221 (1995).

Saga et al. An Antibody–Tumor Model for the Targeting of CA125–producing Gyecologic Malignancies *Jpn. J. Cancer Res.* 81:1141–1148 (1980).

Schmitt et al. Production of Mouse Monoclonal Anti–Idiotypic Antibodies Specific to Epitopes of Tumor–Associated Mucin TAG–12 *Hybridoma* 13:389–396 (1994).

Schultz et al.Detection of Ganglioside $G_{D2}$ in Tumor Tissues and Sera of Neuroblastoma Patients *Cancer Res.* 44:5914–5920 (1984).

Sensi et al. Cytotoxic T–lymphocyte clones from different patients display limited T–cell–receptor variable–region gene usage in HLA–A2–restricted recognition of the melanoma antigen Melan–A/MART–1 *PNAS* 92:5674–5678 (1995).

Sharkey et al. Phase 1 Clinical Evaluation of a New Murine Monoclonal Antibody (Mu–9) against Colon–Specific Antigen–p for Targeting Gastrointestinal Carcinomas *Cancer* 73:864–877 (1994).

Shaw et al. Characterization of a Mouse/Human Chimeric Monoclonal Antibody (17–1A) to a Colon Cancer Tumor–Associated Antigen *J. Immunol.* 138:4534–4538 (1987).

Shimomura et al. Reactions Involved in Bioluminescence of Limpet (*Latia neritoides*) and Luminous Bacteria *Proc. Natl. Acad. Sci. U.S.A.* 69:2086–2089 (1972).

Shimomura et al. Structure of Light–Emitting Moiety of Aequorin *Biochemistry* 11:1602–1608 (1972).

Shimomura et al. The Structure of Latia Luciferin *Biochemistry* 7:1734–1738 (1968).

Siddique et al. Differential Expression of Ganglioside $G_{D3}$ by Human Leukocytes and Leukemia Cells *Cancer Res.* 44:5262–5265 (1984).

Siegel et al. Tumor and Organ Dosimetry for I–131–Labeled LL2 (EPB–2) Monoclonal Antibody inPatients with B–Cell Lymphoma *Antib. Immunoconj. Radiopharm* 4:649–654 (1991).

Solter and Knowles Monoclonal antibody defining a stage–specific mouse embryonic antigen (SSEA–1) *Proc. Natl. Acad. Sci. U.S.A.* 75:5565–5569 (1978).

Sonoda et al. A Novel Tumor–Associated Antigen Expressed in Human Uterine and Ovarian Carcinomas *Cancer* 77:1501–1509 (1996).

Starling et al. Human Prostate Tissue Antigens Defined by Murine Monoclonal Antibodies *Cancer Res.* 46:367–374 (1986).

Stephenson et al. Studies on the Luminescent Response of the $Ca^{2+}$–Activated Photoprotein, Obelin *Biochimica et Biophysica Acta* 678:65–75 (1981).

Strous and Dekker et al. Mucin–Type Glycoproteins *Crit. Rev. Biochem. Mol. Biol.* 27:57–92 (1992).

Stults et al. Use of Recombinant Biotinylated Apoaequorin in Microtiter and Membrane–Based Assays: Purification of Recombinant Apoaequorin from Escherichia coli *Biochemistry* 31:1433–1442 (1992).

Tai et al. Ganglioside GM2 as a human tumor antigen (OFA–I–1) *Proc. Natl. Acad. Sci. U.S.A.* 80:5392–5396 (1983).

Taki et al. Accumulation of Ganglioside with N–Acetylneuraminosyl($\alpha$2–6)lactosamine Structure in Primary Human Hepatoma *Cancer Res.* 50:1284–1290 (1990).

Tempero et al. Phase II Trial of Interferon Gamma and Monoclonal Antibody 17–1A in Pancreatic Cancer: Biologic and Clinical Effects *J. Clin. Oncol.* 8:2019–2026 (1990).

Tempero M. et al. Relationship of Carbohydrate Antigen 19–9 and Lewis Antigens in Pancreatic Cancer *Cancer Res.* 47:5501–5503 (1987).

Thorpe et al. New Coupling Agents for the Synthesis of Immunotoxins Containing a Hindered Disulfide Bond with Improved Stability in Vivo *Cancer Res.* 47:5924–5931 (1987).

Tinari et al. Identification of the Tumor Antigen 90K Domains Recognized by Monoclonal Antibodies SP2 and L3 and Preparation and Characterization of Novel Anti–90K Monoclonal Antibodies *Biochem. Biophys. Res. Commun.* 232:367–372 (1997).

Toso et al. MAGE–1–specific Precursor Cytotoxic T–Lymphocytes Present among Tumor–infiltrating Lymphocytes from a Patient with Breast Cancer: Characterization and Antigen–specific Activation *Cancer Res.* 56:16–20 (1996).

Travis, J. Following the Inner Light, Glow Genes provide revealing pictures of infections *Science News* 150:220–221 (1996).

Travis, J., X–rays speed healing of rat spinal cords, *Science News* 150:214, (1996).

Tsuchida et al. Ganglioside of Human Melanoma *JNCI J. Natl. Cancer Inst.* 78:45–54 (1987a).

Tsuchida et al. Gangliosides of Human Melanoma: Altered Expression in vivo and in Vitro *Cancer Res.* 47:1278–1281 (1987b).

Urdal et al. A Granulocyte Reactive Monoclonal Antibody, IG10, Identifies the Gal$\beta$1–4(Fuc$\alpha$1–3)GlcNAc(X Determinant) Expressed in HL–60 Cells on Both Glycolipid and Glycoprotein Molecules *Blood* 62(5):1022–1026 (1983).

Usuba et al. Establishment of a Human Monoclonal Antibody to Hanganutziu–Deicher Antigen as a Tumor–associated Carbohydrate Antigen as a Tumor–associated Carbohydrate Antigen *J. Chem. Res.* 79:1340–48 (1988).

Van den Eynde et al. A New Family of Genes Coding for an Antigen Recognized by Autologous Cytolytic T Lymphocytes on a Human Melanoma *J. Exp. Med.* 182:689–698 (1995).

Vrionis et al. Five New Epitope–defined Monoclonal Antibodies Reactive with $G_{M2}$ and Human Glioma and Medulloblastoma Cell Lines *Cancer Res.* 49:6641–6649 (1989).

Wakabayashi et al. Syngenic Monoclonal Antibodies Against Melanoma Antigen s With Species Specificity and Interspecies Cross–Reactivity *J. Invest. Dermatol.* 83:128–133 (1984).

Walden et al. Major Histocompatability Complex–Restricted and Unrestricted Activation of Helper T Cell lines by Liposome–Bound Antigens *J. Mol. Cell Immunol.* 2:191–197 (1986).

Wawryznaczak et al. Molecular and biological properties of an abrin A chain immunotoxin designed for therapy of human small cell lung cancer *Br. J. Cancer* 66:361–366 (1992).

Wellhoner et al. Uptake and Concentration of Bioactive Macromolecules by K562 Cells via the Transferrin Cycle Utilizing an Acid–labile Transferrin Conjugate *J. Biol. Chem.* 266:4309–4314 (1991).

Wikstrand C.J. et al. Occurrence of Lacto Series Gangliosides 3'–isoLM1 and 3', 6'–isoLD1 in Human Gliomas in vitro and in vivo *J. Neurophathol Exp. Neurol* 50:765–769 (1991).

Wu et al. Expression of $G_{D2}$ Ganglioside by Untreated Primary Human Neuroblastomas *Cancer Res.* 46:440–443 (1986).

Yamamoto et al. Anti–Idiotype Monoclonal Antibody Carrying the Internal Image of Ganglioside GM3 *J. Natl. Cancer Inst.* 82:1757–1760 (1990).

Zuckermann et al. Efficient Method for the Preparation of Peptoids [Oligo(N–substituted glycines)] by Submonomer Solid–Phase Synthesis *J. Am. Chem.Soc.* 114:10646 (1992).

* cited by examiner

```
                          SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 1196 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
```

(ix) FEATURE:
    (A) NAME/KEY: Coding Sequence
    (B) LOCATION: 1...942
    (D) OTHER INFORMATION: Renilla Reinformis Luciferase (x) PUBLICATION INFORMATION:
    (H) DOCUMENT NUMBER: 5,418,155

(xi) SEQUENCE DESCRIPTION: SEQ ID NO: 1:

| | | | | | | | | | | | | | | | | |
|---|---|---|---|---|---|---|---|---|---|---|---|---|---|---|---|---|
| AGC | TTA | AAG | ATG | ACT | TCG | AAA | GTT | TAT | GAT | CCA | GAA | CAA | AGG | AAA | CGG | 48 |
| Ser | Leu | Lys | Met | Thr | Ser | Lys | Val | Tyr | Asp | Pro | Glu | Gln | Arg | Lys | Arg | |
| 1 | | | | 5 | | | | | 10 | | | | | 15 | | |
| ATG | ATA | ACT | GGT | CCG | CAG | TGG | TGG | GCC | AGA | TGT | AAA | CAA | ATG | AAT | GTT | 96 |
| Met | Ile | Thr | Gly | Pro | Gln | Trp | Trp | Ala | Arg | Cys | Lys | Gln | Met | Asn | Val | |
| | | | 20 | | | | | 25 | | | | | 30 | | | |
| CTT | GAT | TCA | TTT | ATT | AAT | TAT | TAT | GAT | TCA | GAA | AAA | CAT | GCA | GAA | AAT | 144 |
| Leu | Asp | Ser | Phe | Ile | Asn | Tyr | Tyr | Asp | Ser | Glu | Lys | His | Ala | Glu | Asn | |
| | | 35 | | | | | 40 | | | | | 45 | | | | |
| GCT | GTT | ATT | TTT | TTA | CAT | GGT | AAC | GCG | GCC | TCT | TCT | TAT | TTA | TGG | CGA | 192 |
| Ala | Val | Ile | Phe | Leu | His | Gly | Asn | Ala | Ala | Ser | Ser | Tyr | Leu | Trp | Arg | |
| | 50 | | | | | 55 | | | | | 60 | | | | | |
| CAT | GTT | GTG | CCA | CAT | ATT | GAG | CCA | GTA | GCG | CGG | TGT | ATT | ATA | CCA | GAT | 240 |
| His | Val | Val | Pro | His | Ile | Glu | Pro | Val | Ala | Arg | Cys | Ile | Ile | Pro | Asp | |
| 65 | | | | | 70 | | | | | 75 | | | | | 80 | |
| CTT | ATT | GGT | ATG | GGC | AAA | TCA | GGC | AAA | TCT | GGT | AAT | GGT | TCT | TAT | AGG | 288 |
| Leu | Ile | Gly | Met | Gly | Lys | Ser | Gly | Lys | Ser | Gly | Asn | Gly | Ser | Tyr | Arg | |
| | | | | 85 | | | | | 90 | | | | | 95 | | |
| TTA | CTT | GAT | CAT | TAC | AAA | TAT | CTT | ACT | GCA | TGG | TTG | AAC | TTC | TTA | ATT | 336 |
| Leu | Leu | Asp | His | Tyr | Lys | Tyr | Leu | Thr | Ala | Trp | Leu | Asn | Phe | Leu | Ile | |
| | | | | 100 | | | | | 105 | | | | | 110 | | |
| TAC | CAA | AGA | AGA | TCA | TTT | TTT | GTC | GGC | CAT | GAT | TGG | GGT | GCT | TGT | TTG | 384 |
| Tyr | Gln | Arg | Arg | Ser | Phe | Phe | Val | Gly | His | Asp | Trp | Gly | Ala | Cys | Leu | |
| | | | 115 | | | | | 120 | | | | | 125 | | | |
| GCA | TTT | CAT | TAT | AGC | TAT | GAG | CAT | CAA | GAT | AAG | ATC | AAA | GCA | ATA | GTT | 432 |
| Ala | Phe | His | Tyr | Ser | Tyr | Glu | His | Gln | Asp | Lys | Ile | Lys | Ala | Ile | Val | |
| | | 130 | | | | | 135 | | | | | 140 | | | | |
| CAC | GCT | GAA | AGT | GTA | GTA | GAT | GTG | ATT | GAA | TCA | TGG | GAT | GAA | TGG | CCT | 480 |
| His | Ala | Glu | Ser | Val | Val | Asp | Val | Ile | Glu | Ser | Trp | Asp | Glu | Trp | Pro | |
| 145 | | | | | 150 | | | | | 155 | | | | | 160 | |
| GAT | ATT | GAA | GAA | GAT | ATT | GCG | TTG | ATC | AAA | TCT | GAA | GAA | GGA | GAA | AAA | 528 |
| Asp | Ile | Glu | Glu | Asp | Ile | Ala | Leu | Ile | Lys | Ser | Glu | Glu | Gly | Glu | Lys | |
| | | | | 165 | | | | | 170 | | | | | 175 | | |
| ATG | GTT | TTG | GAG | AAT | AAC | TTC | TTC | GTG | GAA | ACC | ATG | TTG | CCA | TCA | AAA | 576 |
| Met | Val | Leu | Glu | Asn | Asn | Phe | Phe | Val | Glu | Thr | Met | Leu | Pro | Ser | Lys | |
| | | | | 180 | | | | | 185 | | | | | 190 | | |
| ATC | ATG | AGA | AAG | TTA | GAA | CCA | GAA | GAA | TTT | GCA | GCA | TAT | CTT | GAA | CCA | 624 |
| Ile | Met | Arg | Lys | Leu | Glu | Pro | Glu | Glu | Phe | Ala | Ala | Tyr | Leu | Glu | Pro | |
| | | | 195 | | | | | 200 | | | | | 205 | | | |
| TTC | AAA | GAG | AAA | GGT | GAA | GTT | CGT | CGT | CCA | ACA | TTA | TCA | TGG | CCT | CGT | 672 |
| Phe | Lys | Glu | Lys | Gly | Glu | Val | Arg | Arg | Pro | Thr | Leu | Ser | Trp | Pro | Arg | |
| | | 210 | | | | | 215 | | | | | 220 | | | | |
| GAA | ATC | CCG | TTA | GTA | AAA | GGT | GGT | AAA | CCT | GAC | GTT | GTA | CAA | ATT | GTT | 720 |
| Glu | Ile | Pro | Leu | Val | Lys | Gly | Gly | Lys | Pro | Asp | Val | Val | Gln | Ile | Val | |
| 225 | | | | | 230 | | | | | 235 | | | | | 240 | |
| AGG | AAT | TAT | AAT | GCT | TAT | CTA | CGT | GCA | AGT | GAT | GAT | TTA | CCA | AAA | ATG | 768 |
| Arg | Asn | Tyr | Asn | Ala | Tyr | Leu | Arg | Ala | Ser | Asp | Asp | Leu | Pro | Lys | Met | |
| | | | | 245 | | | | | 250 | | | | | 255 | | |
| TTT | ATT | GAA | TCG | GAT | CCA | GGA | TTC | TTT | TCC | AAT | GCT | ATT | GTT | GAA | GGC | 816 |
| Phe | Ile | Glu | Ser | Asp | Pro | Gly | Phe | Phe | Ser | Asn | Ala | Ile | Val | Glu | Gly | |
| | | | | 260 | | | | | 265 | | | | | 270 | | |
| GCC | AAG | AAG | TTT | CCT | AAT | ACT | GAA | TTT | GTC | AAA | GTA | AAA | GGT | CTT | CAT | 864 |

-continued

```
Ala Lys Lys Phe Pro Asn Thr Glu Phe Val Lys Val Lys Gly Leu His
        275                 280                 285

TTT TCG CAA GAA GAT GCA CCT GAT GAA ATG GGA AAA TAT ATC AAA TCG      912
Phe Ser Gln Glu Asp Ala Pro Asp Glu Met Gly Lys Tyr Ile Lys Ser
    290                 295                 300

TTC GTT GAG CGA GTT CTC AAA AAT GAA CAA TAA TTACTTTGGT TTTTTATTTA    965
Phe Val Glu Arg Val Leu Lys Asn Glu Gln
305                 310

CATTTTTCCC GGGTTTAATA ATATAAATGT CATTTTCAAC AATTTTATTT TAACTGAATA   1025

TTTCACAGGG AACATTCATA TATGTTGATT AATTTAGCTC GAACTTTACT CTGTCATATC   1085

ATTTTGGAAT ATTACCTCTT TCAATGAAAC TTTATAAACA GTGGTTCAAT TAATTAATAT   1145

ATATTATAAT TACATTTGTT ATGTAATAAA CTCGGTTTTA TTATAAAAAA A            1196

(2) INFORMATION FOR SEQ ID NO: 2:

(i) SEQUENCE CHARACTERISTICS:
        (A) LENGTH: 1822 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1665
        (D) OTHER INFORMATION:  Cypridina hilgendorfii luciferase (x) PUBLICATION INFORMATION:
        (H) DOCUMENT NUMBER: EP 0 387 355 TORAY (xi) SEQUENCE DESCRIPTION: SEQ ID NO: 2:

ATG AAG CTA ATA ATT CTG TCT ATT ATA TTG GCC TAC TGT GTC ACA GTC       48
Met Lys Leu Ile Ile Leu Ser Ile Ile Leu Ala Tyr Cys Val Thr Val
1               5                   10                  15

AAC TGC CAG GAT GCA TGT CCT GTA GAA GCT GAA GCA CCG TCA AGT ACA       96
Asn Cys Gln Asp Ala Cys Pro Val Glu Ala Glu Ala Pro Ser Ser Thr
            20                  25                  30

CCA ACA GTC CCA ACA TCT TGT GAA GCT AAA GAA GGA GAA TGT ATC GAT      144
Pro Thr Val Pro Thr Ser Cys Glu Ala Lys Glu Gly Glu Cys Ile Asp
        35                  40                  45

ACC AGA TGC GCA ACA TGT AAA CGA GAC ATA CTA TCA GAC GGA CTG TGT      192
Thr Arg Cys Ala Thr Cys Lys Arg Asp Ile Leu Ser Asp Gly Leu Cys
50                  55                  60

GAA AAT AAA CCA GGG AAG ACA TGC TGT AGA ATG TGC CAG TAT GTA ATT      240
Glu Asn Lys Pro Gly Lys Thr Cys Cys Arg Met Cys Gln Tyr Val Ile
65                  70                  75                  80

GAA TCC AGA GTA GAA GCT GCT GGA TAT TTT AGA ACG TTT TAC GCC AAA      288
Glu Ser Arg Val Glu Ala Ala Gly Tyr Phe Arg Thr Phe Tyr Ala Lys
                85                  90                  95

AGA TTT AAT TTT CAG GAA CCT GGT AAA TAT GTG CTG GCT CGA GGA ACC      336
Arg Phe Asn Phe Gln Glu Pro Gly Lys Tyr Val Leu Ala Arg Gly Thr
                100                 105                 110

AAG GGT GGC GAC TGG TCT GTA ACC CTC ACC ATG GAG AAT CTA GAT GGA      384
Lys Gly Gly Asp Trp Ser Val Thr Leu Thr Met Glu Asn Leu Asp Gly
        115                 120                 125

CAG AAG GGA GCT GTA CTG ACT AAG ACA ACA CTG GAG GTA GTA GGA GAC      432
Gln Lys Gly Ala Val Leu Thr Lys Thr Thr Leu Glu Val Val Gly Asp
    130                 135                 140

GTA ATA GAC ATT ACT CAA GCT ACT GCA GAT CCT ATC ACA GTT AAC GGA      480
Val Ile Asp Ile Thr Gln Ala Thr Ala Asp Pro Ile Thr Val Asn Gly
145                 150                 155                 160
```

```
GGA GCT GAC CCA GTT ATC GCT AAC CCG TTC ACA ATT GGT GAG GTG ACC      528
Gly Ala Asp Pro Val Ile Ala Asn Pro Phe Thr Ile Gly Glu Val Thr
            165                 170                 175

ATT GCT GTT GTC GAA ATA CCC GGC TTC AAT ATT ACA GTC ATC GAA TTC      576
Ile Ala Val Val Glu Ile Pro Gly Phe Asn Ile Thr Val Ile Glu Phe
                180                 185                 190

TTT AAA CTA ATC GTG ATA GAT ATT CTG GGA GGA AGA TCT GTG AGA ATT      624
Phe Lys Leu Ile Val Ile Asp Ile Leu Gly Gly Arg Ser Val Arg Ile
        195                 200                 205

GCT CCA GAC ACA GCA AAC AAA GGA CTG ATA TCT GGT ATC TGT GGT AAT      672
Ala Pro Asp Thr Ala Asn Lys Gly Leu Ile Ser Gly Ile Cys Gly Asn
    210                 215                 220

CTG GAG ATG AAT GAC GCT GAT GAC TTT ACT ACA GAC GCA GAT CAG CTG      720
Leu Glu Met Asn Asp Ala Asp Asp Phe Thr Thr Asp Ala Asp Gln Leu
225                 230                 235                 240

GCG ATC CAA CCC AAC ATA AAC AAA GAG TTC GAC GGC TGC CCA TTC TAC      768
Ala Ile Gln Pro Asn Ile Asn Lys Glu Phe Asp Gly Cys Pro Phe Tyr
                245                 250                 255

GGG AAT CCT TCT GAT ATC GAA TAC TGC AAA GGT CTC ATG GAG CCA TAC      816
Gly Asn Pro Ser Asp Ile Glu Tyr Cys Lys Gly Leu Met Glu Pro Tyr
            260                 265                 270

AGA GCT GTA TGT CGT AAC AAT ATC AAC TTC TAC TAT TAC ACT CTG TCC      864
Arg Ala Val Cys Arg Asn Asn Ile Asn Phe Tyr Tyr Tyr Thr Leu Ser
        275                 280                 285

TGC GCC TTC GCT TAC TGT ATG GGA GGA GAA GAA AGA GCT AAA CAC GTC      912
Cys Ala Phe Ala Tyr Cys Met Gly Gly Glu Glu Arg Ala Lys His Val
    290                 295                 300

CTT TTC GAC TAT GTT GAG ACA TGC GCT GCA CCG GAA ACG AGA GGA ACG      960
Leu Phe Asp Tyr Val Glu Thr Cys Ala Ala Pro Glu Thr Arg Gly Thr
305                 310                 315                 320

TGT GTT TTA TCA GGA CAT ACT TTC TAT GAC ACA TTC GAC AAA GCC AGA     1008
Cys Val Leu Ser Gly His Thr Phe Tyr Asp Thr Phe Asp Lys Ala Arg
                325                 330                 335

TAT CAA TTC CAG GGC CCA TGC AAA GAG CTT CTG ATG GCC GCA GAC TGT     1056
Tyr Gln Phe Gln Gly Pro Cys Lys Glu Leu Leu Met Ala Ala Asp Cys
            340                 345                 350

TAC TGG AAC ACA TGG GAT GTA AAG GTT TCA CAT AGA GAT GTT GAG TCA     1104
Tyr Trp Asn Thr Trp Asp Val Lys Val Ser His Arg Asp Val Glu Ser
        355                 360                 365

TAC ACT GAG GTA GAG AAA GTA ACA ATC AGG AAA CAG TCA ACT GTA GTA     1152
Tyr Thr Glu Val Glu Lys Val Thr Ile Arg Lys Gln Ser Thr Val Val
    370                 375                 380

GAT TTG ATT GTG GAT GGC AAG CAG GTC AAG GTT GGA GGA GTG GAT GTA     1200
Asp Leu Ile Val Asp Gly Lys Gln Val Lys Val Gly Gly Val Asp Val
385                 390                 395                 400

TCT ATC CCG TAC AGT TCT GAG AAC ACA TCC ATA TAC TGG CAG GAT GGA     1248
Ser Ile Pro Tyr Ser Ser Glu Asn Thr Ser Ile Tyr Trp Gln Asp Gly
                405                 410                 415

GAC ATC CTG ACG ACG GCC ATC CTA CCT GAA GCT CTT GTC GTT AAG TTC     1296
Asp Ile Leu Thr Thr Ala Ile Leu Pro Glu Ala Leu Val Val Lys Phe
            420                 425                 430

AAC TTT AAG CAG CTC CTT GTA GTT CAT ATC AGA GAT CCA TTC GAT GGA     1344
Asn Phe Lys Gln Leu Leu Val Val His Ile Arg Asp Pro Phe Asp Gly
        435                 440                 445

AAG ACA TGC GGC ATA TGT GGT AAC TAT AAT CAA GAT TCA ACT GAT GAT     1392
Lys Thr Cys Gly Ile Cys Gly Asn Tyr Asn Gln Asp Ser Thr Asp Asp
    450                 455                 460

TTC TTT GAC GCA GAA GGA GCA TGC GCT CTG ACC CCC AAT CCC CCA GGA     1440
Phe Phe Asp Ala Glu Gly Ala Cys Ala Leu Thr Pro Asn Pro Pro Gly
```

```
465              470              475              480
TGT ACA GAG GAG CAG AAA CCA GAA GCT GAG CGA CTC TGC AAT AGT CTA    1488
Cys Thr Glu Glu Gln Lys Pro Glu Ala Glu Arg Leu Cys Asn Ser Leu
                    485              490              495

TTT GAT AGT TCT ATC GAC GAG AAA TGT AAT GTC TGC TAC AAG CCT GAC    1536
Phe Asp Ser Ser Ile Asp Glu Lys Cys Asn Val Cys Tyr Lys Pro Asp
                500              505              510

CGT ATT GCA CGA TGT ATG TAC GAG TAT TGC CTG AGG GGA CAG CAA GGA    1584
Arg Ile Ala Arg Cys Met Tyr Glu Tyr Cys Leu Arg Gly Gln Gln Gly
            515              520              525

TTC TGT GAC CAT GCT TGG GAG TTC AAA AAA GAA TGC TAC ATA AAG CAT    1632
Phe Cys Asp His Ala Trp Glu Phe Lys Lys Glu Cys Tyr Ile Lys His
        530              535              540

GGA GAC ACT CTA GAA GTA CCA CCT GAA TGC CAA TAA ATGAACAAAG         1678
Gly Asp Thr Leu Glu Val Pro Pro Glu Cys Gln
545              550              555

ATACAGAAGC TAAGACTACT ACAGCAGAAG ATAAAAGAGA AGCTGTAGTT CTTCAAAAAC  1738

AGTATATTTT GATGTACTCA TTGTTTACTT ACATAAAAAT AAATTGTTAT TATCATAACG  1798

TAAAGAAAAA AAAAAAAAAA AAAA                                        1822

(2) INFORMATION FOR SEQ ID NO: 3:

(i) SEQUENCE CHARACTERISTICS:
        (A) LENGTH: 1644 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1644
        (D) OTHER INFORMATION: Luciola Cruciata Luciferase (Firefly)

(x) PUBLICATION INFORMATION:
        (H) DOCUMENT NUMBER: 4,968,613

(xi) SEQUENCE DESCRIPTION: SEQ ID NO: 3:

ATG GAA AAC ATG GAA AAC GAT GAA AAT ATT GTA GTT GGA CCT AAA CCG    48
Met Glu Asn Met Glu Asn Asp Glu Asn Ile Val Val Gly Pro Lys Pro
1                5                  10                  15

TTT TAC CCT ATC GAA GAG GGA TCT GCT GGA ACA CAA TTA CGC AAA TAC    96
Phe Tyr Pro Ile Glu Glu Gly Ser Ala Gly Thr Gln Leu Arg Lys Tyr
                20                  25                  30

ATG GAG CGA TAT GCA AAA CTT GGC GCA ATT GCT TTT ACA AAT GCA GTT    144
Met Glu Arg Tyr Ala Lys Leu Gly Ala Ile Ala Phe Thr Asn Ala Val
            35                  40                  45

ACT GGT GTT GAT TAT TCT TAC GCC GAA TAC TTG GAG AAA TCA TGT TGT    192
Thr Gly Val Asp Tyr Ser Tyr Ala Glu Tyr Leu Glu Lys Ser Cys Cys
        50                  55                  60

CTA GGA AAA GCT TTG CAA AAT TAT GGT TTG GTT GTT GAT GGC AGA ATT    240
Leu Gly Lys Ala Leu Gln Asn Tyr Gly Leu Val Val Asp Gly Arg Ile
65                  70                  75                  80

GCG TTA TGC AGT GAA AAC TGT GAA GAA TTT TTT ATT CCT GTA ATA GCC    288
Ala Leu Cys Ser Glu Asn Cys Glu Glu Phe Phe Ile Pro Val Ile Ala
                85                  90                  95

GGA CTG TTT ATA GGT GTA GGT GTT GCA CCC ACT AAT GAG ATT TAC ACT    336
Gly Leu Phe Ile Gly Val Gly Val Ala Pro Thr Asn Glu Ile Tyr Thr
                100                 105                 110

TTA CGT GAA CTG GTT CAC AGT TTA GGT ATC TCT AAA CCA ACA ATT GTA    384
Leu Arg Glu Leu Val His Ser Leu Gly Ile Ser Lys Pro Thr Ile Val
```

|  |  |  |  |  |  |  |  |  |  |  |  |  |  |  |  |
|---|---|---|---|---|---|---|---|---|---|---|---|---|---|---|---|
|  |  |  | 115 |  |  |  | 120 |  |  |  |  | 125 |  |  |  |
| TTT | AGT | TCT | AAA | AAA | GGC | TTA | GAT | AAA | GTT | ATA | ACA | GTA | CAG | AAA | ACA |
| Phe | Ser | Ser | Lys | Lys | Gly | Leu | Asp | Lys | Val | Ile | Thr | Val | Gln | Lys | Thr |
|  | 130 |  |  |  | 135 |  |  |  | 140 |  |  |  |  |  |  |

432

GTA ACT ACT ATT AAA ACC ATT GTT ATA CTA GAT AGC AAA GTT GAT TAT   480
Val Thr Thr Ile Lys Thr Ile Val Ile Leu Asp Ser Lys Val Asp Tyr
145             150             155             160

CGA GGA TAT CAA TGT CTG GAC ACC TTT ATA AAA AGA AAC ACT CCA CCA   528
Arg Gly Tyr Gln Cys Leu Asp Thr Phe Ile Lys Arg Asn Thr Pro Pro
        165             170             175

GGT TTT CAA GCA TCC AGT TTC AAA ACT GTG GAA GTT GAC CGT AAA GAA   576
Gly Phe Gln Ala Ser Ser Phe Lys Thr Val Glu Val Asp Arg Lys Glu
            180             185             190

CAA GTT GCT CTT ATA ATG AAC TCT TCG GGT TCT ACC GGT TTG CCA AAA   624
Gln Val Ala Leu Ile Met Asn Ser Ser Gly Ser Thr Gly Leu Pro Lys
        195             200             205

GGC GTA CAA CTT ACT CAC GAA AAT ACA GTC ACT AGA TTT TCT CAT GCT   672
Gly Val Gln Leu Thr His Glu Asn Thr Val Thr Arg Phe Ser His Ala
            210             215             220

AGA GAT CCG ATT TAT GGT AAC CAA GTT TCA CCA GGC ACC GCT GTT TTA   720
Arg Asp Pro Ile Tyr Gly Asn Gln Val Ser Pro Gly Thr Ala Val Leu
225             230             235             240

ACT GTC GTT CCA TTC CAT CAT GGT TTT GGT ATG TTC ACT ACT CTA GGG   768
Thr Val Val Pro Phe His His Gly Phe Gly Met Phe Thr Thr Leu Gly
        245             250             255

TAT TTA ATT TGT GGT TTT CGT GTT GTA ATG TTA ACA AAA TTC GAT GAA   816
Tyr Leu Ile Cys Gly Phe Arg Val Val Met Leu Thr Lys Phe Asp Glu
        260             265             270

GAA ACA TTT TTA AAA ACT CTA CAA GAT TAT AAA TGT ACA AGT GTT ATT   864
Glu Thr Phe Leu Lys Thr Leu Gln Asp Tyr Lys Cys Thr Ser Val Ile
        275             280             285

CTT GTA CCG ACC TTG TTT GCA ATT CTC AAC AAA AGT GAA TTA CTC AAT   912
Leu Val Pro Thr Leu Phe Ala Ile Leu Asn Lys Ser Glu Leu Leu Asn
        290             295             300

AAA TAC GAT TTG TCA AAT TTA GTT GAG ATT GCA TCT GGC GGA GCA CCT   960
Lys Tyr Asp Leu Ser Asn Leu Val Glu Ile Ala Ser Gly Gly Ala Pro
305             310             315             320

TTA TCA AAA GAA GTT GGT GAA GCT GTT GCT AGA CGC TTT AAT CTT CCC   1008
Leu Ser Lys Glu Val Gly Glu Ala Val Ala Arg Arg Phe Asn Leu Pro
            325             330             335

GGT GTT CGT CAA GGT TAT GGT TTA ACA GAA ACA ACA TCT GCC ATT ATT   1056
Gly Val Arg Gln Gly Tyr Gly Leu Thr Glu Thr Thr Ser Ala Ile Ile
            340             345             350

ATT ACA CCA GAA GGA GAC GAT AAA CCA GGA GCT TCT GGA AAA GTC GTG   1104
Ile Thr Pro Glu Gly Asp Asp Lys Pro Gly Ala Ser Gly Lys Val Val
        355             360             365

CCG TTG TTT AAA GCA AAA GTT ATT GAT CTT GAT ACC AAA AAA TCT TTA   1152
Pro Leu Phe Lys Ala Lys Val Ile Asp Leu Asp Thr Lys Lys Ser Leu
        370             375             380

GGT CCT AAC AGA CGT GGA GAA GTT TGT GTT AAA GGA CCT ATG CTT ATG   1200
Gly Pro Asn Arg Arg Gly Glu Val Cys Val Lys Gly Pro Met Leu Met
385             390             395             400

AAA GGT TAT GTA AAT AAT CCA GAA GCA ACA AAA GAA CTT ATT GAC GAA   1248
Lys Gly Tyr Val Asn Asn Pro Glu Ala Thr Lys Glu Leu Ile Asp Glu
            405             410             415

GAA GGT TGG CTG CAC ACC GGA GAT ATT GGA TAT TAT GAT GAA GAA AAA   1296
Glu Gly Trp Leu His Thr Gly Asp Ile Gly Tyr Tyr Asp Glu Glu Lys
            420             425             430

CAT TTC TTT ATT GTC GAT CGT TTG AAG TCT TTA ATC AAA TAC AAA GGA   1344

```
His Phe Phe Ile Val Asp Arg Leu Lys Ser Leu Ile Lys Tyr Lys Gly
            435                 440                 445

TAC CAA GTA CCA CCT GCC GAA TTA GAA TCC GTT CTT TTG CAA CAT CCA      1392
Tyr Gln Val Pro Pro Ala Glu Leu Glu Ser Val Leu Leu Gln His Pro
        450                 455                 460

TCT ATC TTT GAT GCT GGT GTT GCC GGC GTT CCT GAT CCT GTA GCT GGC      1440
Ser Ile Phe Asp Ala Gly Val Ala Gly Val Pro Asp Pro Val Ala Gly
465                 470                 475                 480

GAG CTT CCA GGA GCC GTT GTT GTA CTG GAA AGC GGA AAA AAT ATG ACC      1488
Glu Leu Pro GLy Ala Val Val Val Leu Glu Ser Gly Lys Asn Met Thr
                485                 490                 495

GAA AAA GAA GTA ATG GAT TAT GTT GCA AGT CAA GTT TCA AAT GCA AAA      1536
Glu Lys Glu Val Met Asp Tyr Val Als Ser Gln Val Ser Asn Ala Lys
            500                 505                 510

CGT TTA CGT GGT GGT GTT CGT TTT GTG GAT GAA GTA CCT AAA GGT CTT      1584
Arg Leu Arg Gly Gly Val Arg Phe Val Asp Glu Val Pro Lys Gly Leu
        515                 520                 525

ACT GGA AAA ATT GAC GGC AGA GCA ATT AGA GAA ATC CTT AAG AAA CCA      1632
Thr Gly Lys Ile Asp Gly Arg Ala Ile Arg Glu Ile Leu Lys Lys Pro
530                 535                 540

GTT GCT AAG ATG                                                      1644
Val Ala Lys Met
545

(2) INFORMATION FOR SEQ ID NO: 4:

(i) SEQUENCE CHARACTERISTICS:
        (A) LENGTH: 1820 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1664
        (D) OTHER INFORMATION: Vargula (cypridina) luciferase (x) PUBLICATION INFORMATION:
        (A) AUTHORS: Thompson et al.
        (C) JOURNAL: Proc. Natl. Acad. Sci. U.S.A.
        (D) VOLUME: 86
        (F) PAGES: 1326-1332
        (G) DATE: (1989)
        (H) DOCUMENT NUMBER: JP 3-30678 Osaka (Tsuji)

(xi) SEQUENCE DESCRIPTION: SEQ ID NO: 4:

ATG AAG ATA ATA ATT CTG TCT GTT ATA TTG GCC TAC TGT GTC ACC GAC        48
Met Lys Ile Ile Ile Leu Ser Val Ile Leu Ala Tyr Cys Val Thr Asp
1                   5                  10                  15

AAC TGT CAA GAT GCA TGT CCT GTA GAA GCG GAA CCG CCA TCA AGT ACA        96
Asn Cys Gln Asp Ala Cys Pro Val Glu Ala Glu Pro Pro Ser Ser Thr
                20                  25                  30

CCA ACA GTT CCA ACT TCT TGT GAA GCT AAA GAA GGA GAA TGT ATA GAT       144
Pro Thr Val Pro Thr Ser Cys Glu Ala Lys Glu Gly Glu Cys Ile Asp
            35                  40                  45

ACC AGA TGC GCA ACA TGT AAA CGA GAT ATA CTA TCA GAT GGA CTG TGT       192
Thr Arg Cys Ala Thr Cys Lys Arg Asp Ile Leu Ser Asp Gly Leu Cys
        50                  55                  60

GAA AAT AAA CCA GGG AAG ACA TGC TGT AGA ATG TGC CAG TAT GTG ATT       240
Glu Asn Lys Pro Gly Lys Thr Cys Cys Arg Met Cys Gln Tyr Val Ile
65                  70                  75                  80

GAA TGC AGA GTA GAA GCA GCT GGT TAT TTT AGA ACG TTT TAC GGC AAA       288
Glu Cys Arg Val Glu Ala Ala Gly Tyr Phe Arg Thr Phe Tyr Gly Lys
```

|  |  |  |  |  |  |  |  |  |  |  |  |  |  |  |  |  |
|---|---|---|---|---|---|---|---|---|---|---|---|---|---|---|---|---|
|  |  |  |  |  | 85 |  |  |  | 90 |  |  |  |  | 95 |  |  |
| AGA | TTT | AAT | TTT | CAG | GAA | CCT | GGT | AAA | TAT | GTG | CTG | GCT | AGG | GGA | ACC | 336 |
| Arg | Phe | Asn | Phe | Gln | Glu | Pro | Gly | Lys | Tyr | Val | Leu | Ala | Arg | Gly | Thr |  |
|  |  |  | 100 |  |  |  |  | 105 |  |  |  |  | 110 |  |  |  |
| AAG | GGT | GGC | GAT | TGG | TCT | GTA | ACC | CTC | ACC | ATG | GAG | AAT | CTA | GAT | GGA | 384 |
| Lys | Gly | Gly | Asp | Trp | Ser | Val | Thr | Leu | Thr | Met | Glu | Asn | Leu | Asp | Gly |  |
|  |  | 115 |  |  |  |  | 120 |  |  |  |  | 125 |  |  |  |  |
| CAG | AAG | GGA | GCT | GTG | CTG | ACT | AAG | ACA | ACA | CTG | GAG | GTT | GCA | GGA | GAC | 432 |
| Gln | Lys | Gly | Ala | Val | Leu | Thr | Lys | Thr | Thr | Leu | Glu | Val | Ala | Gly | Asp |  |
|  | 130 |  |  |  |  | 135 |  |  |  |  | 140 |  |  |  |  |  |
| GTA | ATA | GAC | ATT | ACT | CAA | GCT | ACT | GCA | GAT | CCT | ATC | ACA | GTT | AAC | GGA | 480 |
| Val | Ile | Asp | Ile | Thr | Gln | Ala | Thr | Ala | Asp | Pro | Ile | Thr | Val | Asn | Gly |  |
| 145 |  |  |  |  | 150 |  |  |  |  | 155 |  |  |  |  | 160 |  |
| GGA | GCT | GAC | CCA | GTT | ATC | GCT | AAC | CCG | TTC | ACA | ATT | GGT | GAG | GTG | ACC | 528 |
| Gly | Ala | Asp | Pro | Val | Ile | Ala | Asn | Pro | Phe | Thr | Ile | Gly | Glu | Val | Thr |  |
|  |  |  |  | 165 |  |  |  |  | 170 |  |  |  |  | 175 |  |  |
| ATT | GCT | GTT | GTT | GAA | ATA | CCG | GGC | TTC | AAT | ATC | ACA | GTC | ATC | GAA | TTC | 576 |
| Ile | Ala | Val | Val | Glu | Ile | Pro | Gly | Phe | Asn | Ile | Thr | Val | Ile | Glu | Phe |  |
|  |  |  | 180 |  |  |  |  | 185 |  |  |  |  | 190 |  |  |  |
| TTT | AAA | CTA | ATC | GTG | ATT | GAT | ATT | CTG | GGA | GGA | AGA | TCT | GTC | AGA | ATT | 624 |
| Phe | Lys | Leu | Ile | Val | Ile | Asp | Ile | Leu | Gly | Gly | Arg | Ser | Val | Arg | Ile |  |
|  |  | 195 |  |  |  |  | 200 |  |  |  |  | 205 |  |  |  |  |
| GCT | CCA | GAC | ACA | GCA | AAC | AAA | GGA | CTG | ATA | TCT | GGT | ATC | TGT | GGT | AAT | 672 |
| Ala | Pro | Asp | Thr | Ala | Asn | Lys | Gly | Leu | Ile | Ser | Gly | Ile | Cys | Gly | Asn |  |
|  | 210 |  |  |  |  | 215 |  |  |  |  | 220 |  |  |  |  |  |
| CTG | GAG | ATG | AAT | GAC | GCT | GAT | GAC | TTT | ACT | ACA | GAT | GCA | GAT | CAG | CTG | 720 |
| Leu | Glu | Met | Asn | Asp | Ala | Asp | Asp | Phe | Thr | Thr | Asp | Ala | Asp | Gln | Leu |  |
| 225 |  |  |  |  | 230 |  |  |  |  | 235 |  |  |  |  | 240 |  |
| GCG | ATC | CAA | CCC | AAC | ATA | AAC | AAA | GAG | TTC | GAC | GGC | TGC | CCA | TTC | TAT | 768 |
| Ala | Ile | Gln | Pro | Asn | Ile | Asn | Lys | Glu | Phe | Asp | Gly | Cys | Pro | Phe | Tyr |  |
|  |  |  |  | 245 |  |  |  |  | 250 |  |  |  |  | 255 |  |  |
| GGC | AAT | CCT | TCT | GAT | ATC | GAA | TAC | TGC | AAA | GGT | CTG | ATG | GAG | CCA | TAC | 816 |
| Gly | Asn | Pro | Ser | Asp | Ile | Glu | Tyr | Cys | Lys | Gly | Leu | Met | Glu | Pro | Tyr |  |
|  |  |  | 260 |  |  |  |  | 265 |  |  |  |  | 270 |  |  |  |
| AGA | GCT | GTA | TGT | CGT | AAC | AAT | ATC | AAC | TTC | TAC | TAT | TAC | ACT | CTA | TCC | 864 |
| Arg | Ala | Val | Cys | Arg | Asn | Asn | Ile | Asn | Phe | Tyr | Tyr | Tyr | Thr | Leu | Ser |  |
|  |  | 275 |  |  |  |  | 280 |  |  |  |  | 285 |  |  |  |  |
| TGT | GCC | TTC | GCT | TAC | TGT | ATG | GGA | GGA | GAA | GAA | AGA | GCT | AAA | CAC | GTC | 912 |
| Cys | Ala | Phe | Ala | Tyr | Cys | Met | Gly | Gly | Glu | Glu | Arg | Ala | Lys | His | Val |  |
|  | 290 |  |  |  |  | 295 |  |  |  |  | 300 |  |  |  |  |  |
| CTT | TTC | GAC | TAT | GTT | GAG | ACA | TGC | GCT | GCG | CCG | GAA | ACG | AGA | GGA | ACG | 960 |
| Leu | Phe | Asp | Tyr | Val | Glu | Thr | Cys | Ala | Ala | Pro | Glu | Thr | Arg | Gly | Thr |  |
| 305 |  |  |  |  | 310 |  |  |  |  | 315 |  |  |  |  | 320 |  |
| TGT | GTT | TTA | TCA | GGA | CAT | ACT | TTC | TAT | GAC | ACA | TTC | GAC | AAA | GCA | AGA | 1008 |
| Cys | Val | Leu | Ser | Gly | His | Thr | Phe | Tyr | Asp | Thr | Phe | Asp | Lys | Ala | Arg |  |
|  |  |  |  | 325 |  |  |  |  | 330 |  |  |  |  | 335 |  |  |
| TAT | CAA | TTC | CAG | GGC | CCA | TGC | AAG | GAG | ATT | CTG | ATG | GCC | GCA | GAC | TGT | 1056 |
| Tyr | Gln | Phe | Gln | Gly | Pro | Cys | Lys | Glu | Ile | Leu | Met | Ala | Ala | Asp | Cys |  |
|  |  |  | 340 |  |  |  |  | 345 |  |  |  |  | 350 |  |  |  |
| TAC | TGG | AAC | ACA | TGG | GAT | GTA | AAG | GTT | TCA | CAT | AGA | GAC | GTC | GAA | TCA | 1104 |
| Tyr | Trp | Asn | Thr | Trp | Asp | Val | Lys | Val | Ser | His | Arg | Asp | Val | Glu | Ser |  |
|  |  | 355 |  |  |  |  | 360 |  |  |  |  | 365 |  |  |  |  |
| TAC | ACT | GAG | GTA | GAG | AAA | GTA | ACA | ATC | AGG | AAA | CAG | TCA | ACT | GTA | GTA | 1152 |
| Tyr | Thr | Glu | Val | Glu | Lys | Val | Thr | Ile | Arg | Lys | Gln | Ser | Thr | Val | Val |  |
|  | 370 |  |  |  |  | 375 |  |  |  |  | 380 |  |  |  |  |  |
| GAT | CTC | ATT | GTG | GAT | GGC | AAG | CAG | GTC | AAG | GTT | GGA | GGA | GTG | GAT | GTA | 1200 |
| Asp | Leu | Ile | Val | Asp | Gly | Lys | Gln | Val | Lys | Val | Gly | Gly | Val | Asp | Val |  |
| 385 |  |  |  |  | 390 |  |  |  |  | 395 |  |  |  |  | 400 |  |
| TCT | ATC | CCG | TAC | AGC | TCT | GAG | AAC | ACT | TCC | ATA | TAC | TGG | CAG | GAT | GGA | 1248 |

```
Ser Ile Pro Tyr Ser Ser Glu Asn Thr Ser Ile Tyr Trp Gln Asp Gly
            405                 410                 415

GAC ATC CTG ACG ACG GCC ATC CTA CCT GAA GCT CTT GTC GTT AAG TTC    1296
Asp Ile Leu Thr Thr Ala Ile Leu Pro Glu Ala Leu Val Val Lys Phe
            420                 425                 430

AAC TTT AAG CAG CTC CTT GTA GTT CAT ATC AGA GAT CCA TTC GAT GCA    1344
Asn Phe Lys Gln Leu Leu Val Val His Ile Arg Asp Pro Phe Asp Ala
            435                 440                 445

AAG ACA TGC GGC ATA TGT GGT AAC TAT AAT CAA GAT TCA ACT GAT GAT    1392
Lys Thr Cys Gly Ile Cys Gly Asn Tyr Asn Gln Asp Ser Thr Asp Asp
450                 455                 460

TTC TTT GAC GCA GAA GGA GCA TGC GCT CTA ACC CCC AAC CCC CCA GGA    1440
Phe Phe Asp Ala Glu Gly Ala Cys Ala Leu Thr Pro Asn Pro Pro Gly
465                 470                 475                 480

TGT ACA GAG GAA CAG AAA CCA GAA GCT GAG CGA CTT TGC AAT AAT CTC    1488
Cys Thr Glu Glu Gln Lys Pro Glu Ala Glu Arg Leu Cys Asn Asn Leu
                485                 490                 495

TTT GAT TCT TCT ATC GAC GAG AAA TGT AAT GTC TGC TAC AAG CCT GAC    1536
Phe Asp Ser Ser Ile Asp Glu Lys Cys Asn Val Cys Tyr Lys Pro Asp
            500                 505                 510

CGG ATT GCC CGA TGT ATG TAC GAG TAT TGC CTG AGG GGA CAA CAA GGA    1584
Arg Ile Ala Arg Cys Met Tyr Glu Tyr Cys Leu Arg Gly Gln Gln Gly
            515                 520                 525

TTT TGT GAC CAT GCT TGG GAG TTC AAG AAA GAA TGC TAC ATA AAA CAT    1632
Phe Cys Asp His Ala Trp Glu Phe Lys Lys Glu Cys Tyr Ile Lys His
530                 535                 540

GGA GAC ACT CTA GAA GTA CCA CCT GAA TGT CAA TAA ACGTACAAAG         1678
Gly Asp Thr Leu Glu Val Pro Pro Glu Cys Gln
545                 550                 555

ATACAGAAGC TAAGGCTACT ACAGCAGAAG ATAAAAAGA AACTGTAGTT CCTTCAAAAA   1738

CCGTGTATTT TATGTACTCA TTGTTTAATT AGAGCAAAAT AAATTGTTAT TATCATAACT  1798

TAAACTAAAA AAAAAAAAAA AA                                           1820
```

(2) INFORMATION FOR SEQ ID NO: 5:

(i) SEQUENCE CHARACTERISTICS:
        (A) LENGTH: 958 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 115...702
        (D) OTHER INFORMATION: apoaequorin-encoding gene (x) PUBLICATION INFORMATION:
        (A) AUTHORS: Inouye et al.
        (C) JOURNAL: Proc. Natl. Acad. Sci. U.S.A.
        (D) VOLUME: 82
        (F) PAGES: 3154-3158
        (G) DATE: (1985)
        (H) DOCUMENT NUMBER: 5,093,240

(xi) SEQUENCE DESCRIPTION: SEQ ID NO: 5:

```
GGGGGGGGGG GGGGGGGGGG GGGGGGGGGG GGGAATGCAA TTCATCTTTG CATCAAAGAA         60

TTACATCAAA TCTCTAGTTG ATCAACTAAA TTGTCTCGAC AACAACAAGC AAAC ATG         117
                                                            Met
                                                             1

ACA AGC AAA CAA TAC TCA GTC AAG CTT ACA TCA GAC TTC GAC AAC CCA         165
Thr Ser Lys Gln Tyr Ser Val Lys Leu Thr Ser Asp Phe Asp Asn Pro
            5                  10                  15

AGA TGG ATT GGA CGA CAC AAG CAT ATG TTC AAT TTC CTT GAT GTC AAC         213
Arg Trp Ile Gly Arg His Lys His Met Phe Asn Phe Leu Asp Val Asn
            20                  25                  30

CAC AAT GGA AAA ATC TCT CTT GAC GAG ATG GTC TAC AAG GCA TCT GAT         261
His Asn Gly Lys Ile Ser Leu Asp Glu Met Val Tyr Lys Ala Ser Asp
 35                  40                  45

ATT GTC ATC AAT AAC CTT GGA GCA ACA CCT GAG CAA GCC AAA CGA CAC         309
Ile Val Ile Asn Asn Leu Gly Ala Thr Pro Glu Gln Ala Lys Arg His
 50                  55                  60                  65

AAA GAT GCT GTA GAA GCC TTC TTC GGA GGA GCT GGA ATG AAA TAT GGT         357
Lys Asp Ala Val Glu Ala Phe Phe Gly Gly Ala Gly Met Lys Tyr Gly
                 70                  75                  80

GTG GAA ACT GAT TGG CCT GCA TAT ATT GAA GGA TGG AAA AAA TTG GCT         405
Val Glu Thr Asp Trp Pro Ala Tyr Ile Glu Gly Trp Lys Lys Leu Ala
             85                  90                  95

ACT GAT GAA TTG GAG AAA TAC GCC AAA AAC GAA CCA ACG CTC ATC CGT         453
Thr Asp Glu Leu Glu Lys Tyr Ala Lys Asn Glu Pro Thr Leu Ile Arg
             100                 105                 110

ATA TGG GGT GAT GCT TTG TTT GAT ATC GTT GAC AAA GAT CAA AAT GGA         501
Ile Trp Gly Asp Ala Leu Phe Asp Ile Val Asp Lys Asp Gln Asn Gly
 115                 120                 125

GCC ATT ACA CTG GAT GAA TGG AAA GCA TAC ACC AAA GCT GCT GGT ATC         549
Ala Ile Thr Leu Asp Glu Trp Lys Ala Tyr Thr Lys Ala Ala Gly Ile
130                 135                 140                 145

ATC CAA TCA TCA GAA GAT TGC GAG GAA ACA TTC AGA GTG TGC GAT ATT         597
Ile Gln Ser Ser Glu Asp Cys Glu Glu Thr Phe Arg Val Cys Asp Ile
                 150                 155                 160

GAT GAA AGT GGA CAA CTC GAT GTT GAT GAG ATG ACA AGA CAA CAT TTA         645
Asp Glu Ser Gly Gln Leu Asp Val Asp Glu Met Thr Arg Gln His Leu
             165                 170                 175

GGA TTT TGG TAC ACC ATG GAT CCT GCT TGC GAA AAG CTC TAC GGT GGA         693
Gly Phe Trp Tyr Thr Met Asp Pro Ala Cys Glu Lys Leu Tyr Gly Gly
             180                 185                 190

GCT GTC CCC TAAGAAGCTC TACGGTGGTG ATGCACCCTA GGAAGATGAT GTGATTTTGA      752
Ala Val Pro
     195

ATAAAACACT GATGAATTCA ATCAAAATTT TCCAAATTTT TGAACGATTT CAATCGTTTG       812

TGTTGATTTT TGTAATTAGG AACAGATTAA ATCGAATGAT TAGTTGTTTT TTTAATCAAC       872

AGAACTTACA AATCGAAAAA GTAAAAAAAA AAAAAAAAAA AAAAAAAAAA AAAAAAAAA        932

AAAAAAAAAA AAAAAAAAAA AAAAA                                            958

(2) INFORMATION FOR SEQ ID NO: 6:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: cDNA (iii) HYPOTHETICAL: NO
```

(iv) ANTI-SENSE: NO (v) FRAGMENT TYPE:

(vi) ORIGINAL SOURCE:

(ix) FEATURE:
            (A) NAME/KEY: Coding Sequence
            (B) LOCATION: 1...588
            (D) OTHER INFORMATION: Recombinant Aequorin AEQ1

(x) PUBLICATION INFORMATION:
            (A) AUTHORS: Prasher et al.
            (B) TITLE: Sequence Comparisons of Complementary
                DNAs Encoding Aequorin Isotypes
            (C) JOURNAL: Biochemistry
            (D) VOLUME: 26
            (F) PAGES: 1326-1332
            (G) DATE: 1987

(xi) SEQUENCE DESCRIPTION: SEQ ID NO: 6:

```
ATG ACC AGC GAA CAA TAC TCA GTC AAG CTT ACA CCA GAC TTC GAC AAC         48
Met Thr Ser Glu Gln Tyr Ser Val Lys Leu Thr Pro Asp Phe Asp Asn
 1               5                  10                  15

CCA AAA TGG ATT GGA CGA CAC AAG CAC ATG TTT AAT TTT CTT GAT GTC         96
Pro Lys Trp Ile Gly Arg His Lys His Met Phe Asn Phe Leu Asp Val
             20                  25                  30

AAC CAC AAT GGA AGG ATC TCT CTT GAC GAG ATG GTC TAC AAG GCG TCC        144
Asn His Asn Gly Arg Ile Ser Leu Asp Glu Met Val Tyr Lys Ala Ser
         35                  40                  45

GAT ATT GTT ATA AAC AAT CTT GGA GCA ACA CCT GAA CAA GCC AAA CGT        192
Asp Ile Val Ile Asn Asn Leu Gly Ala Thr Pro Glu Gln Ala Lys Arg
     50                  55                  60

CAC AAA GAT GCT GTA GAA GCC TTC TTC GGA GGA GCT GGA ATG AAA TAT        240
His Lys Asp Ala Val Glu Ala Phe Phe Gly Gly Ala Gly Met Lys Tyr
 65                  70                  75                  80

GGT GTA GAA ACT GAA TGG CCT GAA TAC ATC GAA GGA TGG AAA AGA CTG        288
Gly Val Glu Thr Glu Trp Pro Glu Tyr Ile Glu Gly Trp Lys Arg Leu
                 85                  90                  95

GCT TCC GAG GAA TTG AAA AGG TAT TCA AAA AAC CAA ATC ACA CTT ATT        336
Ala Ser Glu Glu Leu Lys Arg Tyr Ser Lys Asn Gln Ile Thr Leu Ile
            100                 105                 110

CGT TTA TGG GGT GAT GCA TTG TTC GAT ATC ATT GAC AAA GAC CAA AAT        384
Arg Leu Trp Gly Asp Ala Leu Phe Asp Ile Ile Asp Lys Asp Gln Asn
        115                 120                 125

GGA GCT ATT TCA CTG GAT GAA TGG AAA GCA TAC ACC AAA TCT GAT GGC        432
Gly Ala Ile Ser Leu Asp Glu Trp Lys Ala Tyr Thr Lys Ser Asp Gly
    130                 135                 140

ATC ATC CAA TCG TCA GAA GAT TGC GAG GAA ACA TTC AGA GTG TGC GAT        480
Ile Ile Gln Ser Ser Glu Asp Cys Glu Glu Thr Phe Arg Val Cys Asp
145                 150                 155                 160

ATT GAT GAA AGT GGA CAG CTC GAT GTT GAT GAG ATG ACA AGA CAA CAT        528
Ile Asp Glu Ser Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT        576
Leu Gly Phe Trp Tyr Thr Met Asp Pro Ala Cys Glu Lys Leu Tyr Gly
            180                 185                 190

GGA GCT GTC CCC TAA                                                    591
Gly Ala Val Pro *
        195
```

(2) INFORMATION FOR SEQ ID NO: 7:

(i) SEQUENCE CHARACTERISTICS:
        (A) LENGTH: 591 base pairs (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
    (A) NAME/KEY: Coding Sequence
    (B) LOCATION: 1...588
    (D) OTHER INFORMATION: Recombinant Aequorin AEQ2

(x) PUBLICATION INFORMATION:
    (A) AUTHORS: Prasher et al.
    (B) TITLE: Sequence Comparisons of Complementary
        DNAs Encoding Aequorin Isotypes
    (C) JOURNAL: Biochemistry
    (D) VOLUME: 26
    (F) PAGES: 1326-1332
    (G) DATE: 1987

(xi) SEQUENCE DESCRIPTION: SEQ ID NO: 7:

```
ATG ACC AGC GAA CAA TAC TCA GTC AAG CTT ACA TCA GAC TTC GAC AAC        48
Met Thr Ser Glu Gln Tyr Ser Val Lys Leu Thr Ser Asp Phe Asp Asn
 1               5                  10                  15

CCA AGA TGG ATT GGA CGA CAC AAG CAT ATG TTC AAT TTC CTT GAT GTC        96
Pro Arg Trp Ile Gly Arg His Lys His Met Phe Asn Phe Leu Asp Val
             20                  25                  30

AAC CAC AAT GGA AAA ATC TCT CTT GAC GAG ATG GTC TAC AAG GCA TCT       144
Asn His Asn Gly Lys Ile Ser Leu Asp Glu Met Val Tyr Lys Ala Ser
         35                  40                  45

GAT ATT GTC ATC AAT AAC CTT GGA GCA ACA CCT GAG CAA GCC AAA CGA       192
Asp Ile Val Ile Asn Asn Leu Gly Ala Thr Pro Glu Gln Ala Lys Arg
     50                  55                  60

CAC AAA GAT GCT GTA GAA GCC TTC TTC GGA GGA GCT GGA ATG AAA TAT       240
His Lys Asp Ala Val Glu Ala Phe Phe Gly Gly Ala Gly Met Lys Tyr
 65                  70                  75                  80

GGT GTG GAA ACT GAT TGG CCT GCA TAT ATT GAA GGA TGG AAA AAA TTG       288
Gly Val Glu Thr Asp Trp Pro Ala Tyr Ile Glu Gly Trp Lys Lys Leu
                 85                  90                  95

GCT ACT GAT GAA TTG GAG AAA TAC GCC AAA AAC GAA CCA ACG CTC ATC       336
Ala Thr Asp Glu Leu Glu Lys Tyr Ala Lys Asn Glu Pro Thr Leu Ile
            100                 105                 110

CGT ATA TGG GGT GAT GCT TTG TTC GAT ATC GTT GAC AAA GAT CAA AAT       384
Arg Ile Trp Gly Asp Ala Leu Phe Asp Ile Val Asp Lys Asp Gln Asn
        115                 120                 125

GGA GCC ATT ACA CTG GAT GAA TGG AAA GCA TAC ACC AAA GCT GCT GGT       432
Gly Ala Ile Thr Leu Asp Glu Trp Lys Ala Tyr Thr Lys Ala Ala Gly
    130                 135                 140

ATC ATC CAA TCA TCA GAA GAT TGC GAG GAA ACA TTC AGA GTG TGC GAT       480
Ile Ile Gln Ser Ser Glu Asp Cys Glu Glu Thr Phe Arg Val Cys Asp
145                 150                 155                 160

ATT GAT GAA AGT GGA CAA CTC GAT GTT GAT GAG ATG ACA AGA CAA CAT       528
Ile Asp Glu Ser Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT       576
Leu Gly Phe Trp Tyr Thr Met Asp Pro Ala Cys Glu Lys Leu Tyr Gly
            180                 185                 190

GGA GCT GTC CCC TAA                                                    591
```

```
Gly Ala Val Pro *
        195

(2) INFORMATION FOR SEQ ID NO: 8:

(i) SEQUENCE CHARACTERISTICS:
        (A) LENGTH: 591 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...588
        (D) OTHER INFORMATION: Recombinant Aequorin AEQ3

(x) PUBLICATION INFORMATION:
        (A) AUTHORS: Prasher et al.
        (B) TITLE: Sequence Comparisons of Complementary
              DNAs Encoding Aequorin Isotypes
        (C) JOURNAL: Biochemistry
        (D) VOLUME: 26
        (F) PAGES: 1326-1332
        (G) DATE: 1987

(xi) SEQUENCE DESCRIPTION: SEQ ID NO: 8:

ATG ACC AGC GAA CAA TAC TCA GTC AAG CTT ACA TCA GAC TTC GAC AAC        48
Met Thr Ser Glu Gln Tyr Ser Val Lys Leu Thr Ser Asp Phe Asp Asn
 1               5                  10                  15

CCA AGA TGG ATT GGA CGA CAC AAG CAT ATG TTC AAT TTC CTT GAT GTC        96
Pro Arg Trp Ile Gly Arg His Lys His Met Phe Asn Phe Leu Asp Val
            20                  25                  30

AAC CAC AAT GGA AAA ATC TCT CTT GAC GAG ATG GTC TAC AAG GCA TCT       144
Asn His Asn Gly Lys Ile Ser Leu Asp Glu Met Val Tyr Lys Ala Ser
        35                  40                  45

GAT ATT GTC ATC AAT AAC CTT GGA GCA ACA CCT GAG CAA GCC AAA CGA       192
Asp Ile Val Ile Asn Asn Leu Gly Ala Thr Pro Glu Gln Ala Lys Arg
    50                  55                  60

CAC AAA GAT GCT GTA GGA GAC TTC TTC GGA GGA GCT GGA ATG AAA TAT       240
His Lys Asp Ala Val Gly Asp Phe Phe Gly Gly Ala Gly Met Lys Tyr
 65                 70                  75                  80

GGT GTG GAA ACT GAT TGG CCT GCA TAC ATT GAA GGA TGG AAA AAA TTG       288
Gly Val Glu Thr Asp Trp Pro Ala Tyr Ile Glu Gly Trp Lys Lys Leu
                85                  90                  95

GCT ACT GAT GAA TTG GAG AAA TAC GCC AAA AAC GAA CCA ACG CTC ATC       336
Ala Thr Asp Glu Leu Glu Lys Tyr Ala Lys Asn Glu Pro Thr Leu Ile
            100                 105                 110

CGT ATA TGG GGT GAT GCT TTG TTC GAT ATC GTT GAC AAA GAT CAA AAT       384
Arg Ile Trp Gly Asp Ala Leu Phe Asp Ile Val Asp Lys Asp Gln Asn
        115                 120                 125

GGA GCC ATT ACA CTG GAT GAA TGG AAA GCA TAC ACC AAA GCT GCT GGT       432
Gly Ala Ile Thr Leu Asp Glu Trp Lys Ala Tyr Thr Lys Ala Ala Gly
    130                 135                 140

ATC ATC CAA TCA TCA GAA GAT TGC GAG GAA ACA TTC AGA GTG TGC GAT       480
Ile Ile Gln Ser Ser Glu Asp Cys Glu Glu Thr Phe Arg Val Cys Asp
145                 150                 155                 160

ATT GAT GAA AAT GGA CAA CTC GAT GTT GAT GAG ATG ACA AGA CAA CAT       528
```

```
Ile Asp Glu Asn Gly Gln Leu Asp Val Asp Glu Met Thr Arg Gln His
            165                 170                 175

TTA GGA TTT TGG TAC ACC ATG GAT CCT GCT TGC GAA AAG CTC TAC GGT      576
Leu Gly Phe Trp Tyr Thr Met Asp Pro Ala Cys Glu Lys Leu Tyr Gly
            180                 185                 190

GGA GCT GTC CCC TAA                                                  591
Gly Ala Val Pro *
        195

(2) INFORMATION FOR SEQ ID NO: 9:

(i) SEQUENCE CHARACTERISTICS:
        (A) LENGTH: 567 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...567
        (D) OTHER INFORMATION: Aequorin photoprotein (x) PUBLICATION INFORMATION:
        (A) AUTHORS: Charbonneau et al.
        (B) TITLE: Amino acid sequence of the calcium-dependent
            photoprotein aequorin
        (C) JOURNAL: Am. Chem. Soc.
        (D) VOLUME: 24
        (E) ISSUE: 24
        (F) PAGES: 6762-6771
        (G) DATE: 1985

(xi) SEQUENCE DESCRIPTION: SEQ ID NO: 9:

GTC AAG CTT ACA CCA GAC TTC GAC AAC CCA AAA TGG ATT GGA CGA CAC      48
Val Lys Leu Thr Pro Asp Phe Asp Asn Pro Lys Trp Ile Gly Arg His
 1               5                  10                  15

AAG CAC ATG TTT AAT TTT CTT GAT GTC AAC CAC AAT GGA AGG ATC TCT      96
Lys His Met Phe Asn Phe Leu Asp Val Asn His Asn Gly Arg Ile Ser
             20                  25                  30

CTT GAC GAG ATG GTC TAC AAG GCG TCC GAT ATT GTT ATA AAC AAT CTT     144
Leu Asp Glu Met Val Tyr Lys Ala Ser Asp Ile Val Ile Asn Asn Leu
         35                  40                  45

GGA GCA ACA CCT GAA CAA GCC AAA CGT CAC AAA GAT GCT GTA GAA GCC     192
Gly Ala Thr Pro Glu Gln Ala Lys Arg His Lys Asp Ala Val Glu Ala
     50                  55                  60

TTC TTC GGA GGA GCT GCA ATG AAA TAT GGT GTA GAA ACT GAA TGG CCT     240
Phe Phe Gly Gly Ala Ala Met Lys Tyr Gly Val Glu Thr Glu Trp Pro
 65                  70                  75                  80

GAA TAC ATC GAA GGA TGG AAA AGA CTG GCT TCC GAG GAA TTG AAA AGG     288
Glu Tyr Ile Glu Gly Trp Lys Arg Leu Ala Ser Glu Glu Leu Lys Arg
                 85                  90                  95

TAT TCA AAA AAC CAA ATC ACA CTT ATT CGT TTA TGG GGT GAT GCA TTG     336
Tyr Ser Lys Asn Gln Ile Thr Leu Ile Arg Leu Trp Gly Asp Ala Leu
            100                 105                 110

TTC GAT ATC ATT GAC AAA GAC CAA AAT GGA GCT ATT TCA CTG GAT GAA     384
Phe Asp Ile Ile Asp Lys Asp Gln Asn Gly Ala Ile Ser Leu Asp Glu
        115                 120                 125
```

```
TGG AAA GCA TAC ACC AAA TCT GCT GGC ATC ATC CAA TCG TCA GAA GAT      432
Trp Lys Ala Tyr Thr Lys Ser Ala Gly Ile Ile Gln Ser Ser Glu Asp
    130                 135                 140

TGC GAG GAA ACA TTC AGA GTG TGC GAT ATT GAT GAA AGT GGA CAG CTC      480
Cys Glu Glu Thr Phe Arg Val Cys Asp Ile Asp Glu Ser Gly Gln Leu
145                 150                 155                 160

GAT GTT GAT GAG ATG ACA AGA CAA CAT TTA GGA TTT TGG TAC ACC ATG      528
Asp Val Asp Glu Met Thr Arg Gln His Leu Gly Phe Trp Tyr Thr Met
                165                 170                 175

GAT CCT GCT TGC GAA AAG CTC TAC GGT GGA GCT GTC CCC                  567
Asp Pro Ala Cys Glu Lys Leu Tyr Gly Gly Ala Val Pro
            180                 185
```

(2) INFORMATION FOR SEQ ID NO: 10:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...588
        (D) OTHER INFORMATION: Aequorin mutant w/increased
            bioluminescence activity (x) PUBLICATION INFORMATION:
        (H) DOCUMENT NUMBER: 5,360,728
        (K) RELEVANT RESIDUES IN SEQ ID NO: 10: Asp 124 changed to
           Ser (xi) SEQUENCE DESCRIPTION: SEQ ID NO: 10:

```
ATG ACC AGC GAA CAA TAC TCA GTC AAG CTT ACA CCA GAC TTC GAC AAC       48
Met Thr Ser Glu Gln Tyr Ser Val Lys Leu Thr Pro Asp Phe Asp Asn
1                   5                   10                  15

CCA AAA TGG ATT GGA CGA CAC AAG CAC ATG TTT AAT TTT CTT GAT GTC       96
Pro Lys Trp Ile Gly Arg His Lys His Met Phe Asn Phe Leu Asp Val
                20                  25                  30

AAC CAC AAT GGA AGG ATC TCT CTT GAC GAG ATG GTC TAC AAG GCG TCC      144
Asn His Asn Gly Arg Ile Ser Leu Asp Glu Met Val Tyr Lys Ala Ser
                35                  40                  45

GAT ATT GTT ATA AAC AAT CTT GGA GCA ACA CCT GAA CAA GCC AAA CGT      192
Asp Ile Val Ile Asn Asn Leu Gly Ala Thr Pro Glu Gln Ala Lys Arg
    50                  55                  60

CAC AAA GAT GCT GTA GAA GCC TTC TTC GGA GGA GCT GCA ATG AAA TAT      240
His Lys Asp Ala Val Glu Ala Phe Phe Gly Gly Ala Ala Met Lys Tyr
65                  70                  75                  80

GGT GTA GAA ACT GAA TGG CCT GAA TAC ATC GAA GGA TGG AAA AGA CTG      288
Gly Val Glu Thr Glu Trp Pro Glu Tyr Ile Glu Gly Trp Lys Arg Leu
                85                  90                  95

GCT TCC GAG GAA TTG AAA AGG TAT TCA AAA AAC CAA ATC ACA CTT ATT      336
Ala Ser Glu Glu Leu Lys Arg Tyr Ser Lys Asn Gln Ile Thr Leu Ile
                100                 105                 110

CGT TTA TGG GGT GAT GCA TTG TTC GAT ATC ATT TCC AAA GAC CAA AAT      384
Arg Leu Trp Gly Asp Ala Leu Phe Asp Ile Ile Ser Lys Asp Gln Asn
            115                 120                 125
```

```
GGA GCT ATT TCA CTG GAT GAA TGG AAA GCA TAC ACC AAA TCT GCT GGC    432
Gly Ala Ile Ser Leu Asp Glu Trp Lys Ala Tyr Thr Lys Ser Ala Gly
    130                 135                 140

ATC ATC CAA TCG TCA GAA GAT TGC GAG GAA ACA TTC AGA GTG TGC GAT    480
Ile Ile Gln Ser Ser Glu Asp Cys Glu Glu Thr Phe Arg Val Cys Asp
145                 150                 155                 160

ATT GAT GAA AGT GGA CAG CTC GAT GTT GAT GAG ATG ACA AGA CAA CAT    528
Ile Asp Glu Ser Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT    576
Leu Gly Phe Trp Tyr Thr Met Asp Pro Ala Cys Glu Lys Leu Tyr Gly
        180                 185                 190

GGA GCT GTC CCC                                                    588
Gly Ala Val Pro
        195
```

(2) INFORMATION FOR SEQ ID NO: 11:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...588
        (D) OTHER INFORMATION: Recombinant site-directed Aequorin
            mutant w/increased biolum. activity (x) PUBLICATION INFORMATION:
        (H) DOCUMENT NUMBER: 5,360,728
        (K) RELEVANT RESIDUES IN SEQ ID NO: 11: Glu 135 changed to Ser (xi) SEQUENCE DESCRIPTION: SEQ ID NO: 11:

```
ATG ACC AGC GAA CAA TAC TCA GTC AAG CTT ACA CCA GAC TTC GAC AAC     48
Met Thr Ser Glu Gln Tyr Ser Val Lys Leu Thr Pro Asp Phe Asp Asn
1                   5                  10                  15

CCA AAA TGG ATT GGA CGA CAC AAG CAC ATG TTT AAT TTT CTT GAT GTC     96
Pro Lys Trp Ile Gly Arg His Lys His Met Phe Asn Phe Leu Asp Val
                20                  25                  30

AAC CAC AAT GGA AGG ATC TCT CTT GAC GAG ATG GTC TAC AAG GCG TCC    144
Asn His Asn Gly Arg Ile Ser Leu Asp Glu Met Val Tyr Lys Ala Ser
            35                  40                  45

GAT ATT GTT ATA AAC AAT CTT GGA GCA ACA CCT GAA CAA GCC AAA CGT    192
Asp Ile Val Ile Asn Asn Leu Gly Ala Thr Pro Glu Gln Ala Lys Arg
        50                  55                  60

CAC AAA GAT GCT GTA GAA GCC TTC TTC GGA GGA GCT GCA ATG AAA TAT    240
His Lys Asp Ala Val Glu Ala Phe Phe Gly Gly Ala Ala Met Lys Tyr
65                  70                  75                  80

GGT GTA GAA ACT GAA TGG CCT GAA TAC ATC GAA GGA TGG AAA AGA CTG    288
Gly Val Glu Thr Glu Trp Pro Glu Tyr Ile Glu Gly Trp Lys Arg Leu
                85                  90                  95

GCT TCC GAG GAA TTG AAA AGG TAT TCA AAA AAC CAA ATC ACA CTT ATT    336
Ala Ser Glu Glu Leu Lys Arg Tyr Ser Lys Asn Gln Ile Thr Leu Ile
            100                 105                 110
```

```
CGT TTA TGG GGT GAT GCA TTG TTC GAT ATC ATT TCC AAA GAC CAA AAT        384
Arg Leu Trp Gly Asp Ala Leu Phe Asp Ile Ile Ser Lys Asp Gln Asn
        115                 120                 125

GGA GCT ATT TCA CTG GAT TCA TGG AAA GCA TAC ACC AAA TCT GCT GGC        432
Gly Ala Ile Ser Leu Asp Ser Trp Lys Ala Tyr Thr Lys Ser Ala Gly
        130                 135                 140

ATC ATC CAA TCG TCA GAA GAT TGC GAG GAA ACA TTC AGA GTG TGC GAT        480
Ile Ile Gln Ser Ser Glu Asp Cys Glu Glu Thr Phe Arg Val Cys Asp
145                 150                 155                 160

ATT GAT GAA AGT GGA CAG CTC GAT GTT GAT GAG ATG ACA AGA CAA CAT        528
Ile Asp Glu Ser Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT        576
Leu Gly Phe Trp Tyr Thr Met Asp Pro Ala Cys Glu Lys Leu Tyr Gly
        180                 185                 190

GGA GCT GTC CCC                                                        588
Gly Ala Val Pro
        195

(2) INFORMATION FOR SEQ ID NO: 12:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...588
        (D) OTHER INFORMATION: Recombinant site-directed
            Aequorin mutant w/increased biolum. activity (x) PUBLICATION INFORMATION:
        (H) DOCUMENT NUMBER:  5,360,728

(xi) SEQUENCE DESCRIPTION: SEQ ID NO: 12:

ATG ACC AGC GAA CAA TAC TCA GTC AAG CTT ACA CCA GAC TTC GAC AAC         48
Met Thr Ser Glu Gln Tyr Ser Val Lys Leu Thr Pro Asp Phe Asp Asn
1                   5                   10                  15

CCA AAA TGG ATT GGA CGA CAC AAG CAC ATG TTT AAT TTT CTT GAT GTC         96
Pro Lys Trp Ile Gly Arg His Lys His Met Phe Asn Phe Leu Asp Val
        20                  25                  30

AAC CAC AAT GGA AGG ATC TCT CTT GAC GAG ATG GTC TAC AAG GCG TCC        144
Asn His Asn Gly Arg Ile Ser Leu Asp Glu Met Val Tyr Lys Ala Ser
                35                  40                  45

GAT ATT GTT ATA AAC AAT CTT GGA GCA ACA CCT GAA CAA GCC AAA CGT        192
Asp Ile Val Ile Asn Asn Leu Gly Ala Thr Pro Glu Gln Ala Lys Arg
50                  55                  60

CAC AAA GAT GCT GTA GAA GCC TTC TTC GGA GGA GCT GCA ATG AAA TAT        240
His Lys Asp Ala Val Glu Ala Phe Phe Gly Gly Ala Ala Met Lys Tyr
65                  70                  75                  80

GGT GTA GAA ACT GAA TGG CCT GAA TAC ATC GAA GGA TGG AAA AGA CTG        288
Gly Val Glu Thr Glu Trp Pro Glu Tyr Ile Glu Gly Trp Lys Arg Leu
                85                  90                  95
```

```
GCT TCC GAG GAA TTG AAA AGG TAT TCA AAA AAC CAA ATC ACA CTT ATT      336
Ala Ser Glu Glu Leu Lys Arg Tyr Ser Lys Asn Gln Ile Thr Leu Ile
            100                 105                 110

CGT TTA TGG GGT GAT GCA TTG TTC GAT ATC ATT TCC AAA GAC CAA AAT      384
Arg Leu Trp Gly Asp Ala Leu Phe Asp Ile Ile Ser Lys Asp Gln Asn
            115                 120                 125

GCA GCT ATT TCA CTG GAT GAA TGG AAA GCA TAC ACC AAA TCT GCT GGC      432
Ala Ala Ile Ser Leu Asp Glu Trp Lys Ala Tyr Thr Lys Ser Ala Gly
130                 135                 140

ATC ATC CAA TCG TCA GAA GAT TGC GAG GAA ACA TTC AGA GTG TGC GAT      480
Ile Ile Gln Ser Ser Glu Asp Cys Glu Glu Thr Phe Arg Val Cys Asp
145                 150                 155                 160

ATT GAT GAA AGT GGA CAG CTC GAT GTT GAT GAG ATG ACA AGA CAA CAT      528
Ile Asp Glu Ser Gly Gln Leu Asp Val Asp Glu Met Thr Arg Gln His
                165                 170                 175

TTA GGA TTT TGG TAC ACC ATG GAT CCT GCT TGC GAA AAG CTC TAC GGT      576
Leu Gly Phe Trp Tyr Thr Met Asp Pro Ala Cys Glu Lys Leu Tyr Gly
            180                 185                 190

GGA GCT GTC CCC                                                      588
Gly Ala Val Pro
            195

(2) INFORMATION FOR SEQ ID NO: 13:

(i) SEQUENCE CHARACTERISTICS:
        (A) LENGTH: 567 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...567
        (D) OTHER INFORMATION: Recombinant apoaequorin (AQUALITE)

(xi) SEQUENCE DESCRIPTION: SEQ ID NO: 13:

GTC AAG CTT ACA CCA GAC TTC GAC AAC CCA AAA TGG ATT GGA CGA CAC       48
Val Lys Leu Thr Pro Asp Phe Asp Asn Pro Lys Trp Ile Gly Arg His
1               5                   10                  15

AAG CAC ATG TTT AAT TTT CTT GAT GTC AAC CAC AAT GGA AGG ATC TCT       96
Lys His Met Phe Asn Phe Leu Asp Val Asn His Asn Gly Arg Ile Ser
            20                  25                  30

CTT GAC GAG ATG GTC TAC AAG GCG TCC GAT ATT GTT ATA AAC AAT CTT      144
Leu Asp Glu Met Val Tyr Lys Ala Ser Asp Ile Val Ile Asn Asn Leu
        35                  40                  45

GGA GCA ACA CCT GAA CAA GCC AAA CGT CAC AAA GAT GCT GTA GAA GCC      192
Gly Ala Thr Pro Glu Gln Ala Lys Arg His Lys Asp Ala Val Glu Ala
50                  55                  60

TTC TTC GGA GGA GCT GGA ATG AAA TAT GGT GTA GAA ACT GAA TGG CCT      240
Phe Phe Gly Gly Ala Gly Met Lys Tyr Gly Val Glu Thr Glu Trp Pro
65                  70                  75                  80

GAA TAC ATC GAA GGA TGG AAA AAA CTG GCT TCC GAG GAA TTG AAA AGG      288
Glu Tyr Ile Glu Gly Trp Lys Lys Leu Ala Ser Glu Glu Leu Lys Arg
                85                  90                  95

TAT TCA AAA AAC CAA ATC ACA CTT ATT CGT TTA TGG GGT GAT GCA TTG      336
Tyr Ser Lys Asn Gln Ile Thr Leu Ile Arg Leu Trp Gly Asp Ala Leu
            100                 105                 110

TTC GAT ATC ATT GAC AAA GAC CAA AAT GGA GCT ATT CTG TCA GAT GAA      384
Phe Asp Ile Ile Asp Lys Asp Gln Asn Gly Ala Ile Leu Ser Asp Glu
            115                 120                 125

TGG AAA GCA TAC ACC AAA TCT GAT GGC ATC ATC CAA TCG TCA GAA GAT      432
```

```
Trp Lys Ala Tyr Thr Lys Ser Asp Gly Ile Ile Gln Ser Ser Glu Asp
    130                 135                 140

TGC GAG GAA ACA TTC AGA GTG TGC GAT ATT GAT GAA AGT GGA CAG CTC         480
Cys Glu Glu Thr Phe Arg Val Cys Asp Ile Asp Glu Ser Gly Gln Leu
145                 150                 155                 160

GAT GTT GAT GAG ATG ACA AGA CAA CAT TTA GGA TTT TGG TAC ACC ATG         528
Asp Val Asp Glu Met Thr Arg Gln His Leu Gly Phe Trp Tyr Thr Met
                165                 170                 175

GAT CCT GCT TGC GAA AAG CTC TAC GGT GGA GCT GTC CCC                     567
Asp Pro Ala Cys Glu Lys Leu Tyr Gly Gly Ala Val Pro
            180                 185
```

(2) INFORMATION FOR SEQ ID NO: 14:

(i) SEQUENCE CHARACTERISTICS:
        (A) LENGTH: 236 amino acids
        (B) TYPE: amino acid
        (D) TOPOLOGY: linear (ii) MOLECULE TYPE: protein (ix) FEATURE:
        (D) OTHER INFORMATION: Vibrio fisheri Flavin reductase (x) PUBLICATION INFORMATION:
        (H) DOCUMENT NUMBER: 5,484,723

(xi) SEQUENCE DESCRIPTION: SEQ ID NO: 14:

```
Met Pro Ile Asn Cys Lys Val Lys Ser Ile Glu Pro Leu Ala Cys Asn
1               5                   10                  15

Thr Phe Arg Ile Leu Leu His Pro Glu Gln Pro Val Ala Phe Lys Ala
                20                  25                  30

Gly Gln Tyr Leu Thr Val Val Met Gly Glu Lys Asp Lys Arg Pro Phe
            35                  40                  45

Ser Ile Ala Ser Ser Pro Cys Arg His Glu Gly Glu Ile Glu Leu His
        50                  55                  60

Ile Gly Ala Ala Glu His Asn Ala Tyr Ala Gly Glu Val Val Glu Ser
65                  70                  75                  80

Met Lys Ser Ala Leu Glu Thr Gly Gly Asp Ile Leu Ile Asp Ala Pro
                85                  90                  95

His Gly Glu Ala Trp Ile Arg Glu Asp Ser Asp Arg Ser Met Leu Leu
            100                 105                 110

Ile Ala Gly Gly Thr Gly Phe Ser Tyr Val Arg Ser Ile Leu Asp His
        115                 120                 125

Cys Ile Ser Gln Gln Ile Gln Lys Pro Ile Tyr Leu Tyr Trp Gly Gly
130                 135                 140

Arg Asp Glu Cys Gln Leu Tyr Ala Lys Ala Glu Leu Glu Ser Ile Ala
145                 150                 155                 160

Gln Ala His Ser His Ile Thr Phe Val Pro Val Val Glu Lys Ser Glu
                165                 170                 175

Gly Trp Thr Gly Lys Thr Gly Asn Val Leu Glu Ala Val Lys Ala Asp
            180                 185                 190

Phe Asn Ser Leu Ala Asp Met Asp Ile Tyr Ile Ala Gly Arg Phe Glu
        195                 200                 205

Met Ala Gly Ala Ala Arg Glu Gln Phe Thr Thr Glu Lys Gln Ala Lys
    210                 215                 220

Lys Glu Gln Leu Phe Gly Asp Ala Phe Ala Phe Ile
225                 230                 235
```

DETECTION AND VISUALIZATION OF NEOPLASTIC TISSUES AND OTHER TISSUES

CROSS REFERENCE TO RELATED APPLICATIONS

This application claims the benefit of priority under 35 U.S.C. §119(e) to U.S. provisional application Ser. No. 60/023,374 to Bruce Bryan, filed Aug. 8, 1996, and entitled DETECTION AND VISUALIZATION OF NEOPLASMS AND OTHER TISSUES.

RELATED APPLICATIONS

Subject matter in this application is related to subject matter in U.S. application Ser. No. 08/597,274 to Bruce Bryan, filed Feb. 6, 1996, entitled "BIOLUMINESCENT NOVELTY ITEMS", and U.S. application Ser. No. 08/757,046 to Bruce Bryan, filed Nov. 25, 1996, entitled "BIOLUMINESCENT NOVELTY ITEMS". The subject matter of each of U.S. application Ser. No. 08/597,274 and U.S. application Ser. No. 081757,046, and U.S. provisional application Ser. No. 60/023,374 is herein incorporated in its entirety by reference thereto.

FIELD OF INVENTION

The present invention relates to bioluminescence generating agents, conjugates containing such agents linked to targeting agents, and methods of use of the conjugates for visualization neoplastic or specialty tissue during invasive and non-invasive surgical procedures.

BACKGROUND OF THE INVENTION

Luminescence is a phenomenon in which energy is specifically channeled to a molecule to produce an excited state. Return to a lower energy state is accompanied by release of a photon (hv). Luminescence includes fluorescence, phosphorescence, chemiluminescence and bioluminescence. Bioluminescence is the process by which living organisms emit light that is visible to other organisms. Luminescence may be represented as follows:

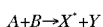

where $X^*$ is an electronically excited molecule and hv represents light emission upon return of $X^*$ to a lower energy state. Where the luminescence is bioluminescence, creation of the excited state derives from an enzyme catalyzed reaction. The color of the emitted light in a bioluminescent (or chemiluminescent or other luminescent) reaction is characteristic of the excited molecule, and is independent from its source of excitation and temperature.

An essential condition for bioluminescence is the use of molecular oxygen, either bound or free in the presence of a luciferase. Luciferases, are oxygenases, that act on a substrate, luciferin, in the presence of molecular oxygen and transform the substrate to an excited state. Upon return to a lower energy level, energy is released in the form of light [for reviews see, e.g., McElroy et al. (1966) in *Molecular Architecture in Cell Physiology*, Hayashi et al., eds., Prentice-Hall, Inc., Englewood Cliffs, N.J., pp. 63–80; Ward et al., Chapter 7 in *Chemi-and Bioluminescence,* Burr, ed., Marcel Dekker, Inc. NY, pp.321–358; Hastings, J. W. in (1995) *Cell Physiology:Source Book,* N. Sperelakis (ed.), Academic Press, pp 665–681; *Luminescence, Narcosis and Life in the Deep Sea,* Johnson, Vantage Press, NY, see, esp. pp. 50–56].

Though rare overall, bioluminescence is more common in marine organisms than in terrestrial organisms. Bioluminescence has developed from as many as thirty evolutionarily distinct origins and, thus, is manifested in a variety of ways so that the biochemical and physiological mechanisms responsible for bioluminescence in different organisms are distinct. Bioluminescent species span many genera and include microscopic organisms, such as bacteria [primarily marine bacteria including Vibrio species], fungi, algae and dinoflagellates, to marine organisms, including arthropods, mollusks, echinoderms, and chordates, and terrestrial organism including annelid worms and insects.

Bioluminescence, as well as other types of chemiluminescence, is used for quantitative determinations of specific substances in biology and medicine. For example, luciferase genes have been cloned and exploited as reporter genes in numerous assays, for many purposes. Since the different luciferase systems have different specific requirements, they may be used to detect and quantify a variety of substances. The majority of commercial bioluminescence applications are based on firefly [*Photinus pyralis*] luciferase. One of the first and still widely used assays involves the use of firefly luciferase to detect the presence of ATP. It is also used to detect and quantify other substrates or co-factors in the reaction. Any reaction that produces or utilizes NAD(H), NADP(H) or long chain aldehyde, either directly or indirectly, can be coupled to the light-emitting reaction of bacterial luciferase.

Another luciferase system that has been used commercially for analytical purposes is the Aequorin system. The purified jellyfish photoprotein, aequorin, is used to detect and quantify intracellular $Ca^{2+}$ and its changes under various experimental conditions. The Aequorin photoprotein is relatively small [~20 kDa], nontoxic, and can be injected into cells in quantities adequate to detect calcium over a large concentration range [$3 \times 10^{-7}$ to $10^{-4}$ M].

Because of their analytical utility, many luciferases and substrates have been studied and well-characterized and are commercially available [e.g., firefly luciferase is available from Sigma, St. Louis, Mo., and Boehringer Mannheim Biochemicals, Indianapolis, Ind.; recombinantly produced firefly luciferase and other reagents based on this gene or for use with this protein are available from Promega Corporation, Madison, Wis.; the aequorin photoprotein luciferase from jellyfish and luciferase from Renilla are commercially available from Sealite Sciences, Bogart, Ga.; coelenterazine, the naturally-occurring substrate for these luciferases, is available from Molecular Probes, Eugene, Oreg.]. These luciferases and related reagents are used as reagents for diagnostics, quality control, environmental testing and other such analyses.

Surgical Procedures

One difficulty encountered by surgeons during surgical procedures either for diagnosis or treatment is to find the tissue of interest. For example, during surgeries in which tumors are excised it is difficult to localize the neoplastic tissue and to be sure to remove all of it, yet not remove healthy tissue. It is also difficult to readily detect metastases, and also, for example to locate the embryo in ectopic pregnancies.

For these reasons and others, it is an object herein to provide means for visualizing neoplastic tissue and specialty tissue during surgical procedures. It is also an object herein to provide methods of detecting neoplastic and specialty tissue.

SUMMARY OF THE INVENTION

Diagnostic systems that rely on bioluminescence for visualizing tissues in situ are provided. The systems are particularly useful for visualizing and detecting neoplastic tissue and specialty tissue, such as during non-invasive and invasive procedures. Kits that provide the components of the systems and methods using the systems for visualizing the tissue are also provided. Therapeutic methods in which photosensitizing compounds are administered are also provided.

The systems include compositions containing conjugates that include a tissue specific, particularly a tumor-specific, targeting agent linked to a targeted agent, a luciferase or luciferin. The systems also include a second composition that contains the remaining components of a bioluminescence generating reaction. In some embodiments, all components, except for activators, which are provided in situ or are present in the body or tissue, are included in a single composition.

In particular, the diagnostic systems include two compositions. A first composition that contains conjugates that, in preferred embodiments, include antibodies directed against tumor antigens conjugated to a component of the bioluminescence generating reaction, a luciferase or luciferin, preferably a luciferase are provided. In certain embodiments, conjugates containing tumor-specific targeting agents are linked to luciferases or luciferins. In other embodiments, tumor-specific targeting agents are linked to microcarriers that are coupled with, preferably more than one of the bioluminescence generating components, preferably more than one luciferase molecule.

The second compostion contains the remaining components of a bioluminescence generating system, typically the luciferin or luciferase substrate. In some embodiments, these components, particularl the luciferin are linked to a protein, such as a serum albumin, or other protein carrier. The carrier and time release formulations, permit systemically administered components to travel to the targeted tissue without interaction with blood cell components, such as hemoglobin that deactive the luciferin or luciferase. Preferred bioluminescence generating systems include the Vargula luciferase/luciferin.

In certain, the bioluminescence generating compositions are packaged in a time release formulation, such as cyclodextran, a liposome or other such vehicle, for delivery through the bloodstream to the tumor.

The compositions are useful in methods for the detection and localization of neoplastic tissue or other tissue, such as endometriosic or an ectopic pregnancy, in a mammal, particularly a human.

The conjugates permit the specific targeting of a bioluminescent agent to neoplastic tissue or other targeted tissue. Upon binding to or interaction with the tissue, when treated with an appropriate substrate (when luciferase is linked) or luciferase (when a luciferin is linked) in the presence of activators, if necessary, light is produced, thereby permitting detection and localization of neoplastic tissue or other targeted tissue. This can, for example, permit or aid in identification of neoplastic tissue, which may then be removed using noninvasive or invasive surgical procedures. In some embodiments, the conjugate may also include a chemotheraputic agent that is delivered to the targeted tissue.

The conjugates contain one or more targeting agents [hereinafter TA] linked, either directly or via a linker, to one or more luciferases or luciferins are provided. For purposes herein, the targeting agent is any molecule that specifically interacts with a cell surface moiety that is present on a tumor cell or tissue or neoplastic cell or tissue or other targeted cell in a higher amount or concentration than on a non-tumor or non-neoplastic cell or non-targeted cell. The higher amount or concentration is any amount or concentration that permits tumor or neoplastic cells to be distinguished from non tumor or neoplastic cells or tissues using the methods and systems and compositions provided herein.

The conjugates provided herein contain the following components: $(TA)_n$, $(L)_q$, and (targeted agent)$_m$ in which: at least one TA moiety is linked with or without a linker (L) to at least one targeted agent, n is 1 or more, preferably 1–3, more preferably 1 or 2, but is any number whereby the resulting conjugate binds to the tumor or neoplastic cell or tissue, q is generally 1 to 4; m is 1 or more, generally 1 or 2; L refers to a linker, and the targeted agent is any agent that when treated with an activator, will produce light.

It is understood that the above description does not represent the order in which each component is linked or the manner in which each component is linked. The TA and targeted agent (or linker and targeted agent) may be linked in any order and through any appropriate linkage, as long as the resulting conjugate binds to a neoplastic cell or tissue receptor and can be visualized by the methods herein. The TA may be linked directly to the targeted agent, such as by a covalent bond, or may be linked through a linker. The TA may also be indirectly linked through a microcarrier that is coupled to the targeted agent.

The targeted agents for use herein are luciferases or photoproteins and substrates (luciferins) therefor.

The targeting agents [TAs] include any agent that will preferentially bind to a tumor or neoplastic cell or tissue compared to cell or tissue that is not a tumor or neoplastic or that target to specialty tissues such as ligaments, tendons, endometriotic tissue, ectopic pregnancies and other such tissues. Such agents include, but are not limited to tissue specific monoclonal antibodies, methotrexate and growth factors, such as FGF, EGF, HBEFG, that can be modified whereby internalization does not occur or is reduced and other such growth factors that bind to receptors that are present in greater amounts or concentrations on neoplastic or tumorous cells or tissues than non-tumorous or non-neoplastic tissues. Monoclonal antibodies specific for tumor cell surface proteins are presently preferred. Among the monoclonal antibodies, humanized monoclonal antibodies are preferred.

Methods for diagnosis and visualization of tissues in vivo or in situ are provided. Included are methods of identifying metastatic tumors or other targeted tissue during an operative procedure, typically an exploratory procedure, by the preoperative administration of a targeting agent conjugated to one of the bioluminescence-generating components and followed by the topical or local application of the final components during surgery to illuminate areas of neoplasia. In the methods provided herein, bioluminescence is used to visualize the targeted tissue in an animal during surgical procedures, such as for surgical removal.

Methods for the preparation of the conjugates and the resulting conjugates are provided. These methods include chemical conjugation methods and methods that rely on recombinant production of the conjugates. The chemical methods rely on derivatization of the targeted agent or TA with the desired linker and then reaction with a TA or targeted agent. Alternatively, the derivatized targeted agent is coupled to a microcarrier directly or through a linker and then coupled to a TA. The chemical methods of derivatization are particularly preferred. Direct linkage is presently preferred.

Presently the methods for preparation of antibody-luciferase conjugates, such as those described in U.S. Pat. No. 5,486,455 are among the preferred methods.

If a linker is used it is selected such that it does not interfere with the activity of the targeted agent upon interaction of the conjugate with a cell surface protein. Any appropriate linker known to those of skill in this art may be used. The linker may be selected to improve activity by permitting the targeted agent to react with the activating composition. In some instances the linker is selected to increase the specificity, toxicity, solubility, serum stability, and/or intracellular availability targeted moiety. In some embodiments, several linkers may be included in order to take advantage of desired properties of each linker.

Other linkers are suited for incorporation into chemically produced conjugates. Linkers that are suitable for chemically linking conjugates include disulfide bonds, thioether bonds, hindered disulfide bonds, esters, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups on the other. Other linkers include, acid cleavable linkers, such as bismaleimideothoxy propane, acid labile-transferrin conjugates and adipic acid diihydrazide, that would be cleaved in more acidic environments; photocleavable cross linkers that are cleaved by visible or UV light. Linkers particularly suitable for coupling microcarriers to TA and targeted agents are chemical linking conjugates as well as avidin/streptavidin-biotin conjugates.

Kits containing the compositions for use in the diagnostic systems are provided. In particular, the kits include a first composition that contains the conjugates, and a second that contains the activating composition, which contains any necessary activating agents, as well as the luciferase, if the targeted agent is a luciferin, or a luciferin, if the targeted agent is a luciferase.

Thus, the kits will typically include two compositions, a first composition containing the conjugate formulated for systemic administration (or in some embodiments local or topical application), and a second composition, formulated for systemic, topical or local administration depending upon the application. Instructions for administration will be included.

Methods of detecting bioluminescent neoplasia and specialty tissues for surgical removal using surgical viewing devices are also provided. Methods of detecting and surgically removing bioluminescent neoplasia and specialty tissues using these surgical viewing devices are also provided. These devices include night vision binoculars, CCD arrays, tomographs, endoscopic devices and other such devices.

Surgical instruments for detecting and surgically removing bioluminescent neoplastic and specialty tissue are provided. Methods of detecting and surgically removing bioluminescent neoplasia and specialty tissues using these surgical viewing devices are also provided. In particular, a surgical vision device, that includes: an optical detection system that is operatively associated with the image intensifier such that an image detected by the optical detection system is transmitted to the image intensifier for viewing; an image intensifier device highly sensitive to low intensity visible light; and an objective lens assembly.

Compositions and methods of using bioluminescence targeting agents, as described herein, in conjunction with photodynamic methodologies for the treatment of neoplasms are also provided. In practicing the methods, a photodynamic drug is administered prior to the administration of a targeting agent conjugated to a component of a bioluminescence generating system. Binding of the targeting agent to the targeted neoplaisa and initiation of the bioluminescent reaction results in in situ production of light at the surface of the cell thereby irradiating those neoplastic tissues that uptake the photodynamic drug. Photoactivation of the drug results in death of the targeted cell.

In practicing the methods, a conjugate containing a targeting agent linked to a luciferase or luciferin is administered to an animal prior to surgery or diagnosis. During surgery or the diagnostic procedure, when the tissues can be seen, they are contacted with a composition containing the remaining components of a bioluminescence generating system. Any tissues to which the targeting agent binds will glow, thereby permitting the surgeon to identify the tissues.

In other methods, a luciferase, such as red emitting luciferase, including those from Aristostomias, *A. niger*, Melanocostus and Pachystomias, that produces light that can be detected through tissue is conjugated to a targeting agent and administered prior to surgery or a diagnostic procedure. A composition containing the remaining components of the bioluminescence generating system is injected either locally or systemically prior to surgery or diagnosis. When systemically administered, the components, such as the luciferin can be provided in a time release formulation, or can include other components, such as an albumin that prevent it from getting into the blood cells or that prevent interaction with other blood components. Tissues to which the tumor-specific targeting agent binds are detected using a photomultiplier or other surgical viewing instrument directly through the skin without the need for invasive surgery.

In other methods, a luciferase that produces light that can be detected through tissue, e.g., Aristostomias, is conjugated to a targeting agent and administered prior to surgery. Light is detected from the targeted tissue using a surgical instrument, such as a laparoscope or tomogram, and the image of the targeted tissue is displayed and removed by one or more invasive or non-invasive surgical techniques.

DETAILED DESCRIPTION OF THE INVENTION

Table of Contents

A. Definitions
B. Preparation of the Conjugates
  1. Bioluminescence generating systems
    a. General description
      (1) Luciferases
      (2) Luciferins
      (3) Activators
      (4) Reactions
    b. Ctenophore and coelenterate systems
      (1) The aequorin system
        (a) Aequorin and related photoproteins
        (b) Luciferin
      (2) The Renilla system
    c. Crustacean, particularly Cyrpidina systems
      (1) Vargula luciferase
        (a) Purification from Cypridina
        (b) Preparation by Recombinant Methods
      (2) Vargula luciferin
      (3) Reaction
    d. Insect bioluminescent systems including fireflies, click beetles, and other insect system
      (1) Luciferase
      (2) Luciferin
      (3) Reaction
    e. Bacterial systems
      (1) Luciferases (2) Luciferins
   (3) Reactions
  f. Other systems
   (1) Dinoflagellate bioluminescence generating systems
   (2) Systems from molluscs, such as Latia and Pholas
   (3) Earthworms and other annelids
   (4) Glow worms
   (5) Marine polycheate worm systems
   (6) South American railway beetle
   (7) Fish
  g. Other fluorescent proteins
   (1) Green and blue fluorescent proteins
   (2) Phycobiliproteins
  2. Linkers
  3. Targeting Agents
C. Formulation and Administration of Pharmaceutical Compositions
D. Practice of the Reactions in Combination with Targeting Agents
E. Kits and Compositions
  1. Dispensing and Packaging Apparatus for Combination with the Bioluminescent System Components
  2. Capsules, pellets, liposomes, endosomes, vacuoles, micronized particles
   a. Encapsulating vehicles in general
   b. Encapsulating vehicles -liposomes
   c. Encapsulating vehicles -gelatin and polymeric vehicles
   d. Endosomes and vacuoles
   e. Micronized particles
  3. Immobilized systems
   a. Matrix materials
   b. Immobilization and activation
F. Surgical Devices and Instruments
   a. Surgical viewing device
   b. Surgical imaging instruments
G. Photodynamic Therapy
H. Practice of the Methods

A. Definitions

Unless defined otherwise, all technical and scientific terms used herein have the same meaning as is commonly understood by one of skill in the art to which this invention belongs. All patents and publications of referred to herein are incorporated by reference in their entirety.

As used herein, chemiluminescence refers to a chemical reaction in which energy is specifically channeled to a molecule causing it to become electronically excited and subsequently to release a photon thereby emitting visible light. Temperature does not contribute to this channeled energy. Thus, chemiluminescence involves the direct conversion of chemical energy to light energy.

As used herein, luminescence refers to the detectable EM radiation, generally, UV, IR or visible EM radiation that is produced when the excited product of an exergic chemical process reverts to its ground state with the emission of light. Chemiluminescence is luminescence that results from a chemical reaction. Bioluminescence is chemiluminescence that results from a chemical reaction using biological molecules [or synthetic versions or analogs thereof] as substrates and/or enzymes.

As used herein, bioluminescence, which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein [luciferase] that is an oxygenase that acts on a substrate luciferin [a bioluminescence substrate] in the presence of molecular oxygen and transforms the substrate to an excited state, which upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives, for example, bacterial luciferin or firefly luciferase.

As used herein, luciferase refers to oxygenases that catalyze a light emitting reaction. For instance, bacterial luciferases catalyze the oxidation of flavin mononucleotide [FMN] and aliphatic aldehydes, which reaction produces light. Another class of luciferases, found among marine arthropods, catalyzes the oxidation of Cypridina [Vargula] luciferin, and another class of luciferases catalyzes the oxidation of Coleoptera luciferin.

Thus, luciferase refers to an enzyme or photoprotein that catalyzes a bioluminescent reaction [a reaction that produces bioluminescence]. The luciferases, such as firefly and Renilla luciferases, that are enzymes which act catalytically and are unchanged during the bioluminescence generating reaction. The luciferase photoproteins, such as the aequorin photoprotein to which luciferin is non-covalently bound, are changed, such as by release of the luciferin, during bioluminescence generating reaction. The luciferase is a protein that occurs naturally in an organism or a variant or mutant thereof, such as a variant produced by mutagenesis that has one or more properties, such as thermal stability, that differ from the naturally-occurring protein. Luciferases and modified mutant or variant forms thereof are well known. For purposes herein, reference to luciferase refers to either the photoproteins or luciferases.

Thus, reference, for example, to "Renilla luciferase" means an enzyme isolated from member of the genus Renilla or an equivalent molecule obtained from any other source, such as from another Anthozoa, or that has been prepared synthetically.

The luciferases and luciferin and activators thereof are referred to as bioluminescence generating reagents or components. Typically, a subset of these reagents will be provided or combined with an article of manufacture. Bioluminescence will be produced upon contacting the combination with the remaining reagents. Thus, as used herein, the component luciferases, luciferins, and other factors, such as $O_2$, $Mg^{2+}$, $Ca^{2+}$ are also referred to as bioluminescence generating reagents [or agents or components].

As used herein, "not strictly catalytically" means that the photoprotein acts as a catalyst to promote the oxidation of the substrate, but it is changed in the reaction, since the bound substrate is oxidized and bound molecular oxygen is used in the reaction. Such photoproteins are regenerated by addition of the substrate and molecular oxygen under appropriate conditions known to those of skill in this art.

As used herein, bioluminescence substrate refers to the compound that is oxidized in the presence of a luciferase, and any necessary activators, and generates light. These substrates are referred to as luciferins herein, are substrates that undergo oxidation in a bioluminescence reaction. These bioluminescence substrates include any luciferin or analog thereof or any synthetic compound with which a luciferase interacts to generate light. Preferred substrates are those that are oxidized in the presence of a luciferase or protein in a light-generating reaction. Bioluminescence substrates, thus, include those compounds that those of skill in the art recognize as luciferins. Luciferins, for example, include firefly luciferin, Cypridina [also known as Vargula] luciferin [coelenterazine], bacterial luciferin, as well as synthetic analogs of these substrates or other compounds that are oxidized in the presence of a luciferase in a reaction the produces bioluminescence.

As used herein, capable of conversion into a bioluminescence substrate means susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide ($FMNH_2$) by a flavin reductase enzyme. The reduced flavin mononucleotide [substrate] then reacts with oxygen [an activator] and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, bioluminescence system [or bioluminescence generating system] refers to the set of reagents required to conduct a bioluminescent reaction. Thus, the specific luciferase, luciferin and other substrates, solvents and other reagents that may be required to complete a bioluminescent reaction form a bioluminescence system. Thus a bioluminescence system refers to any set of reagents that, under appropriate reaction conditions, yield bioluminescence. Appropriate reaction conditions refers to the conditions necessary for a bioluminescence reaction to occur, such as pH, salt concentrations and temperature. In general, bioluminescence systems include a bioluminescence substrate, luciferin, a luciferase, which includes enzymes luciferases and photoproteins, and one or more activators. A specific bioluminescence system may be identified by reference to the specific organism from which the luciferase derives; for example, the Vargula [also called Cypridina] bioluminescence system (or Vargula system) includes a Vargula luciferase, such as a luciferase isolated from the ostracod, Vargula or produced using recombinant means or modifications of these luciferases. This system would also include the particular activators necessary to complete the bioluminescence reaction, such as oxygen and a substrate with which the luciferase reacts in the presence of the oxygen to produce light.

The amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, to target a targeted agent, such as a luciferase, means to direct it to a cell that expresses a selected receptor or other cell surface protein by linking the agent to a such agent. Upon binding to or interaction with the receptor or cell surface protein the targeted agent, can be reacted with an appropriate substrate and activating agents, whereby bioluminescent light is produced and the tumorous tissue or cells distinguished from non-tumorous tissue.

As used herein, an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, an effective amount of a conjugate for diagnosing a disease is an amount that will result in a detectable tissue. The tissues are detected by visualization either without aid from a detector more sensitive than the human eye, or with the use of a light source to excite any fluorescent products.

As used herein, visualizable means detectable by eye, particularly during surgery under normal surgical conditions, or, if necessary, slightly dimmed light.

As used herein, pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects and that either are pharmaceutically active or are prodrugs.

As used herein, treatment means any manner in which the symptoms of a conditions, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers or isomers. In such instances, further purification might increase the specific activity of the compound.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach,* Oxford University Press, New York, pages 388–392).

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, $ED_{50}$ refers to the concentration at which 50% of the cells are killed following a 72-hour incubation with a cytotoxic conjugate, such as FGF-SAP.

As used herein, $ID_{50}$ refers to the concentration of a cytotoxic conjugate required to inhibit protein synthesis in treated cells by 50% compared to protein synthesis in the absence of the protein.

As used herein, targeting agent refers to an agent that specifically or preferentially targets a linked targeted agent, a luciferin or luciferase, to a neoplastic cell or tissue.

As used herein, tumor antigen refers to a cell surface protein expressed or located on the surface of tumor cells.

As used herein, neoplastic cells include any type of transformed or altered cell that exhibits characteristics typical of transformed cells, such as a lack of contact inhibition and the acquisition of tumor-specific antigens. Such cells include, but are not limited to leukemic cells and cells derived from a tumor.

As used herein, neoplastic disease is any disease in which neoplastic cells are present in the individual afflicted with the disease. Such diseases include, any disease characterized as cancer.

As used herein, metastatic tumors refers to tumors that are not localized in one site.

As used herein, specialty tissue refers to non-tumorous tissue for which information regarding location is desired. Such tissues include, for example, endometriotic tissue, ectopic pregnancies, tissues associated with certain disorders and myopathies or pathologies.

As used herein, an antibody conjugate refers to a conjugate in which the targeting agent is an antibody.

As used herein, antibody activation refers to the process whereby activated antibodies are produced. Antibodies are activated upon reaction with a linker, such as heterobifunctional reagent.

As used herein, a surgical viewing refers to any procedure in which an opening is made in the body of an animal. Such procedures include traditional surgeries and diagnostic procedures, such as laparoscopies and arthroscopic procedures.

As used herein, humanized antibodies refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, ATP, AMP, NAD+ and NADH refer to adenosine triphosphate, adenosine monophosphate, nicotinamide adenine dinucleotide (oxidized form) and nicotinamide adenine dinucleotide (reduced form), respectively.

As used herein, production by recombinant means by using recombinant DNA methods means the use of the well known methods of molecular biology for expressing proteins encoded by cloned DNA.

As used herein, substantially identical to a product means sufficiently similar so that the property of interest is sufficiently unchanged so that the substantially identical product can be used in place of the product.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein equivalent, when referring to two sequences of nucleic acids means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions [see, e.g., Table 2, below] that do not substantially alter the activity or function of the protein or peptide. When "equivalent" refers to a property, the property does not need to be present to the same extent [e.g., two peptides can exhibit different rates of the same type of enzymatic activity], but the activities are preferably substantially the same. "Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: stringency of hybridization in determining percentage mismatch is as follows:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

It is understood that equivalent stringencies may be achieved using alternative buffers, salts and temperatures.

The term "substantially" identical or homologous or similar varies with the context as understood by those skilled in the relevant art and generally means at least 70%, preferably means at least 80%, more preferably at least 90%, and most preferably at least 95% identity.

As used herein, biological activity refers to the in vivo activities of a compound or physiological responses that result upon administration of a compound, composition or other mixture. Biological activities may be observed in in vitro systems designed to test or use such activities. Thus, for purposes herein the biological activity of a luciferase is its oxygenase activity whereby, upon oxidation of a substrate, light is produced.

As used herein, a composition refers to a any mixture. It may be a solution, a suspension, liquid, powder, a paste, aqueous, non-aqueous or any combination thereof.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

B. Prepration of the Conjugates

The conjugates that are provided herein contain a targeting agent, such as a tissue specific or tumor specific monoclonal antibody or fragment thereof linked either directly or via a linker to a targeted agent, a luciferase (including photoproteins or luciferase enzymes) or a luciferin. The targeted agent may be coupled to a microcarrier. The linking is effected either chemically, by recombinant expression of a fusion protein in instances when the targeted agent is a protein, and by combinations of chemical and recombinant expression. The targeting agent is one that will preferentially bind to a selected tissue or cell type, such as a tumor cell surface antigen or other tissue specific antigen.

Methods for preparing conjugates are known to those of skill in the art. For example, aequorin that is designed for conjugation and conjugates containing such aequorin have been produced [see, e.g., International PCT application No. WO 94/18342; see, also Smith et al. (1995) in *American Biotechnology Laboratory*]. Aequorin has been conjugated to an antibody molecule by means of a sulfhydryl-reacting binding agent (Stultz et al. (1992) Use of Recombinant Biotinylated Apoaequorin from *Escherichia coli*. Biochemistry 31, 1433–1442). Such methods may be adapted for use herein to produce aequorin coupled to protein or other such molecules, which are useful as targeting agents. Vargula luciferase has also been linked to other molecules [see, e.g., Japanese application No. JP 5064583, Mar. 19, 1993]. Such methods may be adapted for use herein to produce aequorin coupled to protein or other such molecules, which are useful as targeting agents.

Aequorin-antibody conjugates have been employed to detect the presence of or quantitate a particular antigen in a biological sample by direct correlation to the light emitted from the bioluminescent reaction.

As an alternative, a component of the bioluminescence generating system may be modified for linkage, such as by addition of amino acid residues that are particularly suitable for linkage to the selected substrate. This can be readily effected by modifying the DNA and expressing such modified DNA to produce luciferase with additional residues at the N- or C-terminus.

Selection of the system depends upon factors such as the desired color and duration of the bioluminescence desired as well as the particular item. Selection of the targeting agent primarily depends upon the type and characteristics of neoplasia or tissue to be visualized and the setting in which visualization will be performed. For example, the luciferase isolated from Aristostomias emits red light, which is particularly beneficial for preoperative diagnosis because the red light is detectable through tissue using a photomultiplier.

1. Bioluminescence Generating Systems

A bioluminescence generating system refers to the components that are necessary and sufficient to generate bioluminescence. These include a luciferase, luciferin and any necessary co-factors or conditions. Virtually any bioluminescent system known to those of skill in the art will be amenable to use in the apparatus, systems, combinations and methods provided herein. Factors for consideration in selecting a bioluminescent-generating system, include, but are not limited to: the targeting agent used in combination with the bioluminescence; the medium in which the reaction is run; stability of the components, such as temperature or pH sensitivity; shelf life of the components; sustainability of the light emission, whether constant or intermittent; availability of components; desired light intensity; color of the light; and other such factors.

a. General Description

In general, bioluminescence refers to an energy-yielding chemical reaction in which a specific chemical substrate, a luciferin, undergoes oxidation, catalyzed by an enzyme, a luciferase. Bioluminescent reactions are easily maintained, requiring only replenishment of exhausted luciferin or other substrate or cofactor or other protein, in order to continue or revive the reaction. Bioluminescence generating reactions are well-known to those of skill in this art and any such reaction may be adapted for use in combination with articles of manufacture as described herein.

There are numerous organisms and sources of bioluminescence generating systems, and some representative genera and species that exhibit bioluminescence are set forth in the following table [reproduced in part from Hastings in (1995) *Cell Physiology:Source Book*, N. Sperelakis (ed.), Academic Press, pp 665–681]:

TABLE 1

Representative luminous organism

| Type of Organism | Representative genera |
|---|---|
| Bacteria | Photobacterium |
|  | Vibrio |
|  | Xenorhabdus |
| Mushrooms | Panus, Armillaria |
|  | Pleurotus |
| Dinoflagellates | Gonyaulax |
|  | Pyrocystis |
|  | Noctiluca |
| Cnidaria (coelenterates) | |
| Jellyfish | Aequorea |
| Hydroid | Obelia |
| Sea Pansy | Renilla |
| Ctenophores | Mnemiopsis |
|  | Beroe |
| Annelids | |
| Earthworms | Diplocardia |
| Marine polychaetes | Chaetopterus, Phyxotrix |
| Syllid fireworm | Odontosyllis |
| Molluscs | |
| Limpet | Latia |
| Clam | Pholas |
| Squid | Heteroteuthis |
|  | Heterocarpus |
| Crustacea | |
| Ostracod | Vargula (Cypridina) |
| Shrimp (euphausids) | Meganyctiphanes |
|  | Acanthophyra |
|  | Oplophorus |
|  | Gnathophausia |
| Decapod | Sergestes |
| Copepods | |
| Insects | |
| Coleopterids (beetles) | |
| Firefly | Photinus, Photuris |
| Click beetles | Pyrophorus |
| Railroad worm | Phengodes, Phrixothrix |
| Diptera (flies) | Arachnocampa |
| Echinoderms | |
| Brittle stars | Ophiopsila |
| Sea cucumbers | Laetmogone |
| Chordates | |
| Tunicates | Pyrosoma |
| Fish | |
| Cartilaginous | Squalus |
| Bony | |
| Ponyfish | Leiognathus |
| Flashlight fish | Photoblepharon |
| Angler fish | Cryptopsaras |

TABLE 1-continued

Representative luminous organism

| Type of Organism | Representative genera |
|---|---|
| Midshipman | Porichthys |
| Lantern fish | Benia |
| Shiny loosejaw | Aristostomias |
| Hatchet fish | Agyropelecus |
| and other fish | Pachystomias |
|  | Malacosteus |
| Midwater fish | Cyclothone |
|  | Neoscopelus |
|  | Tarletonbeania |

Other bioluminescent organisms contemplated for use herein are Gonadostomias, Gaussia, Watensia, Halisturia, Vampire squid, Glyphus, Mycotophids (fish), Vinciguerria, Howella, Florenciella, Chaudiodus, Melanocostus and Sea Pens.

It is understood that a bioluminescence generating system may be isolated from natural sources, such as those in the above Table, or may be produced synthetically. In addition, for uses herein, the components need only be sufficiently pure so that mixture thereof, under appropriate reaction conditions, produces a glow so that cells and tissues can be visualized during a surgical procedure.

Thus, in some embodiments, a crude extract or merely grinding up the organism may be adequate. Generally, however, substantially pure components are used. Also, components may be synthetic components that are not isolated from natural sources. DNA encoding luciferases is available [see, e.g., SEQ ID Nos. 1–13] and has been modified [see, e.g., SEQ ID Nos. 3 and 10–13] and synthetic and alternative substrates have been devised. The DNA listed herein is only representative of the DNA encoding luciferases that is available.

Any bioluminescence generating system, whether synthetic or isolated form natural sources, such as those set forth in Table 1, elsewhere herein or known to those of skill in the art, is intended for use in the combinations, systems and methods provided herein. Chemiluminescence systems per se, which do not rely on oxygenases [luciferases] are not encompassed herein.

(1) Luciferases

The targeted agents herein include luciferases or luciferins. Luciferases refer to any compound that, in the presence of any necessary activators, catalyze the oxidation of a bioluminescence substrate [luciferin] in the presence of molecular oxygen, whether free or bound, from a lower energy state to a higher energy state such that the substrate, upon return to the lower energy state, emits light. For purposes herein, luciferase is broadly used to encompass enzymes that act catalytically to generate light by oxidation of a substrate and also photoproteins, such as aequorin, that act, though not strictly catalytically [since such proteins are exhausted in the reaction], in conjunction with a substrate in the presence of oxygen to generate light. These luciferases, including photoproteins, such as aequorin, are herein also included among the luciferases. These reagents include the naturally-occurring luciferases [including photoproteins], proteins produced by recombinant DNA, and mutated or modified variants thereof that retain the ability to generate light in the presence of an appropriate substrate, co-factors and activators or any other such protein that acts as a catalyst to oxidize a substrate, whereby light is produced.

Generically, the protein that catalyzes or initiates the bioluminescent reaction is referred to as a luciferase, and the oxidizable substrate is referred to as a luciferin. The oxidized reaction product is termed oxyluciferin, and certain luciferin precursors are termed etioluciferin. Thus, for purposes herein bioluminescence encompasses light produced by reactions that are catalyzed by [in the case of luciferases that act enzymatically] or initiated by [in the case of the photoproteins, such as aequorin, that are not regenerated in the reaction] a biological protein or analog, derivative or mutant thereof.

For clarity herein, these catalytic proteins are referred to as luciferases and include enzymes such as the luciferases that catalyze the oxidation of luciferin, emitting light and releasing oxyluciferin. Also included among luciferases are photoproteins, which catalyze the oxidation of luciferin to emit light but are changed in the reaction and must be reconstituted to be used again. The luciferases may be naturally occurring or may be modified, such as by genetic engineering to improve or alter certain properties. As long as the resulting molecule retains the ability to catalyze the bioluminescent reaction, it is encompassed herein.

Any protein that has luciferase activity [a protein that catalyzes oxidation of a substrate in the presence of molecular oxygen to produce light as defined herein] may be used herein. The preferred luciferases are those that are described herein or that have minor sequence variations. Such minor sequence variations include, but are not limited to, minor allelic or species variations and insertions or deletions of residues, particularly cysteine residues. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p.224). Such substitutions are preferably made in accordance with those set forth in TABLE 2 as follows:

TABLE 2

| Original residue | Conservative substitution |
|---|---|
| Ala (A) | Gly; Ser |
| Arg (R) | Lys |
| Asn (N) | Gln; His |
| Cys (C) | Ser; neutral amino acid |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions. Any such modification of the polypeptide may be effected by any means known to those of skill in this art.

The luciferases may be obtained commercially, isolated from natural sources, expressed in host cells using DNA encoding the luciferase, or obtained in any manner known to those of skill in the art. For purposes herein, crude extracts obtained by grinding up selected source organisms may suffice. Since large quantities of the luciferase may be desired, isolation of the luciferase from host cells is preferred. DNA for such purposes is widely available as are modified forms thereof.

Examples of luciferases include, but are not limited to, those isolated from the ctenophores Mnemiopsis (mnemiopsin) and *Beroe ovata* (berovin), those isolated from the coelenterates Aequorea (aequorin), Obelia (obelin), Pelagia, the Renilla luciferase, the luciferases isolated from the mollusca Pholas (pholasin), the luciferases isolated from fish, such as Aristostomias, Pachystomias and Porichthys and from the ostracods, such as Cypridina (also referred to as Vargula). Preferred luciferases for use herein are the Aequorin protein, Renilla luciferase and Cypridina [also called Vargula] luciferase [see, e.g., SEQ ID Nos. 1, 2, and 4–13]. Also, preferred are luciferases which react to produce red and/or near infrared light. These include luciferases found in species of Aristostomias, such as *A. scintillans,* Pachystomias, Malacosteus, such as *M. niger.*

(2) Luciferins

The substrates for the reaction or for inclusion in the conjugates include any molecule(s) with which the luciferase reacts to produce light. Such molecules include the naturally-occurring substrates, modified forms thereof, and synthetic substrates [see, e.g., U.S. Pat. Nos. 5,374,534 and 5,098,828]. Exemplary luciferins include those described herein, as well as derivatives thereof, analogs thereof, synthetic substrates, such as dioxetanes [see, e.g., U.S. Pat. Nos. 5,004,565 and 5,455,357], and other compounds that are oxidized by a luciferase in a light-producing reaction [see, e.g., U.S. Pat. Nos. 5,374,534, 5,098,828 and 4,950,588]. Such substrates also may be identified empirically by selecting compounds that are oxidized in bioluminescent reactions.

(3) Activators

The bioluminescent generating systems also require additional components discussed herein and known to those of skill in the art. All bioluminescent reactions require molecular oxygen in the form of dissolved or bound oxygen. Thus, molecular oxygen, dissolved in water or in air or bound to a photoprotein, is the activator for bioluminescence reactions. Depending upon the form of the components, other activators include, but are not limited to, ATP [for firefly luciferase], flavin reductase [bacterial systems] for regenerating $FMNH_2$ from FMN, and $Ca^{2+}$ or other suitable metal ion [aequorin].

Most of the systems provided herein will generate light when the luciferase and luciferin are mixed and exposed to air or water. The systems that use photoproteins that have bound oxygen, such as aequorin, however, will require exposure to $Ca^{2+}$ [or other suitable metal ion], which can be provided in the form of an aqueous composition of a calcium salt. In these instances, addition of a $Ca^{2+}$ [or other suitable metal ion] to a mixture of luciferase [aequorin] and luciferin [such as coelenterazine] will result in generation of light. The Renilla system and other Anthozoa systems also require $Ca^{2+}$ [or other suitable metal ion].

If crude preparations are used, such as ground up Cypridina [shrimp] or ground fireflies, it may be necessary to add only water. In instances in which fireflies [or a firefly or beetle luciferase] are used the reaction may only require addition ATP. The precise components will be apparent, in light of the disclosure herein, to those of skill in this art or may be readily determined empirically.

It is also understood that these mixtures will also contain any additional salts or buffers or ions that are necessary for each reaction to proceed. Since these reactions are well-characterized, those of skill in the art will be able to determine precise proportions and requisite components. Selection of components will depend upon the apparatus, article of manufacture and luciferase. Various embodiments are described and exemplified herein; in view of such description, other embodiments will be apparent.

(4) Reactions

In all embodiments, all but one component, either the luciferase or luciferin, of a bioluminescence generating system will be mixed or packaged with or otherwise combined. The remaining component is conjugated to a targeting agent and is intended for administration to an animal.

Prior to a surgical procedure, the conjugate is administered via any suitable route, whereby the targeting agent binds to the targeted tissue by virtue of its specific interaction with a tissue-specific cell surface protein. During surgery the tissue is contacted, with the remaining component (s), typically by spraying the area or local injection, and any tissue to which conjugate is bound will glow. The glow should be sufficient to see under dim light or, if necessary, in the dark.

In general, since the result to be achieved is the production of light visible to the naked eye for qualitative, not quantitative, diagnostic purposes, the precise proportions and amounts of components of the bioluminescence reaction need not be stringently determined or met. They must be sufficient to produce light. Generally, an amount of luciferin and luciferase sufficient to generate a visible glow is used; this amount can be readily determined empirically and is dependent upon the selected system and selected application. Where quantitative measurements are required, more precision may be required.

For purposes herein, such amount is preferably at least the concentrations and proportions used for analytical purposes by those of skill in the such arts. Higher concentrations may be used if the glow is not sufficiently bright. Alternatively, a microcarrier coupled to more than one luciferase molecule linked to a targeting agent may be utilized to increase signal output. Also because the conditions in which the reactions are used are not laboratory conditions and the components are subject to storage, higher concentration may be used to overcome any loss of activity. Typically, the amounts are 1 mg, preferably 10 mg and more preferably 100 mg, of a luciferase per liter of reaction mixture or 1 mg, preferably 10 mg, more preferably 100 mg. Compositions may contain at least about 0.01 mg/l, and typically 0.1 mg/l, 1 mg/l, 10 mg/l or more of each component on the item. The amount of luciferin is also between about 0.01 and 100 mg/l, preferably between 0.1 and 10 mg/l, additional luciferin can be added to many of the reactions to continue the reaction. In embodiments in which the luciferase acts catalytically and does not need to be regenerated, lower amounts of luciferase can be used. In those in which it is changed during the reaction, it also can be replenished; typically higher concentrations will be selected. Ranges of concentration per liter [or the amount of coating on substrate the results from contacting with such composition] of each component on the order of 0.1 to 20 mg, preferably 0.1 to 10 mg, more preferably between about 1 and 10 mg of each component will be sufficient. When preparing coated substrates, as described herein, greater amounts of coating compositions containing higher concentrations of the luciferase or luciferin may be used.

Thus, for example, in presence of calcium, 5 mg of luciferin, such as coelenterazine, in one liter of water will glow brightly for at least about 10 to 20 minutes, depending on the temperature of the water, when about 10 mgs of luciferase, such as aequorin photoprotein luciferase or luciferase from Renilla, is added thereto. Increasing the concentration of luciferase, for example, to 100 mg/l, provides a particularly brilliant display of light.

It is understood, that concentrations and amounts to be used depend upon the selected bioluminescence generating system but these may be readily determined empirically. Proportions, particularly those used when commencing an empirical determination, are generally those used for analytical purposes, and amounts or concentrations are at least those used for analytical purposes, but the amounts can be increased, particularly if a sustained and brighter glow is desired.

b. Ctenophore and Coelenterate Systems

Ctenophores, such as Mnemiopsis (mnemiopsin) and *Beroe ovata* (berovin), and coelenterates, such as Aequorea (aequorin), Obelia (obelin) and Pelagia, produce bioluminescent light using similar chemistries [see, e.g., Stephenson et al. (1981) *Biochimica et Biophysica Acta 678*:65–75; Hart et al. (1979) *Biochemistry 18*:2204–2210; International PCT Application No. WO 94/18342, which is based on U.S. application Ser. No. 08/017,116, U.S. Pat. No. 5,486,455 and other references and patents cited herein]. The Aequorin and Renilla systems are representative and are described in detail herein as exemplary and as among the presently preferred systems. The Aequorin and Renilla systems can use the same luciferin and produce light using the same chemistry, but each luciferase is different. The Aequorin luciferase aequorin, as well as, for example, the luciferases mnemiopsin and berovin, is a photoprotein that includes bound oxygen and bound luciferin, requires $Ca^{2+}$ [or other suitable metal ion] to trigger the reaction, and must be regenerated for repeated use; whereas, the Renilla luciferase acts as a true enzyme because it is unchanged during the reaction and it requires dissolved molecular oxygen.

(1) The Aequorin System

The aequorin system is well known [see, e.g., Tsuji et al. (1986) "Site-specific mutagenesis of the calcium-binding photoprotein aequorin," *Proc. Natl. Acad. Sci. USA 83*:8107–8111; Prasher et al. (1985) "Cloning and Expression of the cDNA Coding for Aequorin, a Bioluminescent Calcium-Binding Protein," *Biochemical and Biophysical Research Communications 126*:1259–1268; Prasher et al. (1986) *Methods in Enzymology 133*:288–297; Prasher, et al. (1987) "Sequence Comparisons of cDNAs Encoding for Aequorin Isotypes," *Biochemistry 26*:1326–1332; Charbonneau et al. (1985) "Amino Acid Sequence of the Calcium-Dependent Photoprotein Aequorin," *Biochemistry 24*:6762–6771; Shimomura et al. (1981) "Resistivity to denaturation of the apoprotein of aequorin and reconstitution of the luminescent photoprotein from the partially denatured apoprotein," *Biochem. J. 199*:825–828; Inouye et al. (1989) *J. Biochem. 105*:473–477; Inouye et al. (1986) "Expression of Apoaequorin Complementary DNA in *Escherichia coli*," *Biochemistry 25*:8425–8429; Inouye et al. (1985) "Cloning and sequence analysis of cDNA for the luminescent protein aequorin," *Proc. Natl. Acad. Sci. USA 82*:3154–3158; Prendergast, et al. (1978) "Chemical and Physical Properties of Aequorin and the Green Fluorescent Protein Isolated from *Aequorea forskalea*" *J. Am. Chem. Soc. 17*:3448–3453; European Patent Application 0 540 064 A1; European Patent Application 0 226 979 A2, European Patent Application 0 245 093 A1 and European Patent Application 0 245 093 B1; U.S. Pat. No. 5,093,240; U.S. Pat. No. 5,360,728; U.S. Pat. No. 5,139,937; U.S. Pat. No. 5,422,266; U.S. Pat. No. 5,023,181; U.S. Pat. No. 5,162,227; and SEQ ID Nos. 5–13, which set forth DNA encoding the apoprotein; and a form, described in U.S. Pat. No. 5,162,227, European Patent Application 0 540 064 A1 and Sealite Sciences Technical Report No. 3 (1994), is commercially available from Sealite, Sciences, Bogart, Ga. as AQUALITE®].

This system is among the preferred systems for use herein. As will be evident, since the aequorin photoprotein includes noncovalently bound luciferin and molecular oxygen, it is suitable for storage in this form as a lyophilized powder or encapsulated into a selected delivery vehicle. The system can be encapsulated into pellets, such as liposomes or other delivery vehicles. When used, the vehicles are contacted with a composition, even tap water, that contains $Ca^{2+}$ [or other suitable metal ion], to produce a mixture that glows.

(a) Aequorin and Related Photoproteins

The photoprotein, aequorin, isolated from the jellyfish, Aequorea, emits light upon the addition of $Ca^{2+}$ [or other suitable metal ion]. The aequorin photoprotein, which includes bound luciferin and bound oxygen that is released by $Ca^{2+}$, does not require dissolved oxygen. Luminescence is triggered by calcium, which releases oxygen and the luciferin substrate producing apoaqueorin.

The bioluminescence photoprotein aequorin is isolated from a number of species of the jellyfish Aequorea. It is a 22 kilodalton [kD] molecular weight peptide complex [see, e.g., Shimomura et al. (1962) *J. Cellular and Comp. Physiol. 59*:233–238; Shimomura et al. (1969) *Biochemistry 8*:3991–3997; Kohama et al. (1971) *Biochemistry 10*:4149–4152; and Shimomura et al. (1972) *Biochemistry 11*:1602–1608]. The native protein contains oxygen and a heterocyclic compound coelenterazine, a luciferin, [see, below] noncovalently bound thereto. The protein contains three calcium binding sites. Upon addition of trace amounts $Ca^{2+}$ [or other suitable metal ion, such as strontium] to the photoprotein, it undergoes a conformational change the catalyzes the oxidation of the bound coelenterazine using the protein-bound oxygen. Energy from this oxidation is released as a flash of blue light, centered at 469 nm. Concentrations of calcium ions as low as $10^{-6}$ M are sufficient to trigger the oxidation reaction.

Naturally-occurring apoaequorin is not a single compound but rather is a mixture of microheterogeneous molecular species. Aequoria jellyfish extracts contain as many as twelve distinct variants of the protein [see, e.g., Prasher et al. (187) *Biochemistry 26*:1326–1332; Blinks et al. (1975) *Fed. Proc. 34*:474]. DNA encoding numerous forms has been isolated [see, e.g., SEQ ID Nos. 5–9 and 13].

The photoprotein can be reconstituted [see, e.g., U.S. Pat. No. 5,023,181] by combining the apoprotein, such as a protein recombinantly produced in *E. coli*, with a coelenterazine, such as a synthetic coelenterazine, in the presence of oxygen and a reducing agent [see, e.g., Shimomura et al. (1975) *Nature 256*:236–238; Shimomura et al. (1981) *Biochemistry J. 199*:825–828], such as 2-mercaptoethanol, and also EDTA or EGTA

[concentrations between about 5 to about 100 mM or higher for applications herein] tie up any $Ca^{2+}$ to prevent triggering the oxidation reaction until desired. DNA encoding a modified form of the apoprotein that does not require 2-mercaptoethanol for reconstitution is also available [see, e.g., U.S. Pat. No. U.S. Pat. No. 5,093,240]. The reconstituted photoprotein is also commercially available [sold, e.g., under the trademark AQUALITE®, which is described in U.S. Pat. No. 5,162,227].

The light reaction is triggered by adding $Ca^{2+}$ at a concentration sufficient to overcome the effects of the chelator and achieve the $10^{-6}$ M concentration. Because such low concentrations of $Ca^{2+}$ can trigger the reaction, for use in the methods herein, higher concentrations of chelator may be included in the compositions of photoprotein. Accordingly, higher concentrations of added $Ca^{2+}$ in the form of a calcium salt will be required. Precise amounts may be empirically determined. For use herein, it may be sufficient to merely add water to the photoprotein, which is provided in the form of a concentrated composition or in lyophilized or powdered form. Thus, for purposes herein, addition of small quantities of $Ca^{2+}$, such as those present in phosphate buffered saline (PBS) or other suitable buffers or the moisture on the tissue to which the compositions are contacted, should trigger the bioluminescence reaction.

Numerous isoforms of the aequorin apoprotein been identified isolated. DNA encoding these proteins has been cloned, and the proteins and modified forms thereof have been produced using suitable host cells [see, e.g., U.S. Pat. Nos. 5,162,227, 5,360,728, 5,093,240; see, also, Prasher et al. (1985) *Biophys. Biochem. Res. Commun.* 126:1259–1268; Inouye et al. (1986) *Biochemistry* 25:8425–84291. U.S. Pat. No. 5,093,240; U.S. Pat. No. 5,360,728; U.S. Pat. No. 5,139,937; U.S. Pat. No. 5,288,623; U.S. Pat. No. 5,422,266, U.S. Pat. No. 5,162,227 and SEQ ID Nos. 5–13, which set forth DNA encoding the apoprotein; and a form is commercially available form Sealite, Sciences, Bogart, Ga. as AQUALITE®]. DNA encoding apoaequorin or variants thereof is useful for recombinant production of high quantities of the apoprotein. The photoprotein is reconstituted upon addition of the luciferin, coelenterazine, preferably a sulfated derivative thereof, or an analog thereof, and molecular oxygen [see, e.g., U.S. Pat. No. 5,023,181]. The apoprotein and other constituents of the photoprotein and bioluminescence generating reaction can be mixed under appropriate conditions to regenerate the photoprotein and concomitantly have the photoprotein produce light. Reconstitution requires the presence of a reducing agent, such as mercaptoethanol, except for modified forms, discussed below, that are designed so that a reducing agent is not required [see, e.g., U.S. Pat. No. 5,093,240].

For use herein, it is preferred aequorin is produced using DNA, such as that set forth in SEQ ID Nos. 5–13 and known to those of skill in the art or modified forms thereof. The DNA encoding aequorin is expressed in a host cell, such as *E. coli*, isolated and reconstituted to produce the photoprotein [see, e.g., U.S. Pat. Nos. 5,418,155, 5,292,658, 5,360, 728, 5,422,266, 5,162,227].

Of interest herein, are forms of the apoprotein that have been modified so that the bioluminescent activity is greater than unmodified apoaequorin [see, e.g., U.S. Pat. No. 5,360, 728, SEQ ID Nos. 10–12]. Modified forms that exhibit greater bioluminescent activity than unmodified apoaequorin include proteins having sequences set forth in SEQ ID Nos. 10–12, in which aspartate 124 is changed to serine, glutamate 135 is changed to serine, and glycine 129 is changed to alanine, respectively. Other modified forms with increased bioluminescence are also available.

For use in certain embodiments herein, the apoprotein and other components of the aequorin bioluminescence generating system are packaged or provided as a mixture, which, when desired is subjected to conditions under which the photoprotein reconstitutes from the apoprotein, luciferin and oxygen [see, e.g., U.S. Pat. No. 5,023,181; and U.S. Pat. No. 5,093,240]. Particularly preferred are forms of the apoprotein that do not require a reducing agent, such as 2-mercaptoethanol, for reconstitution. These forms, described, for example in U.S. Pat. No. 5,093,240 [see, also Tsuji et al. (1986) *Proc. Natl. Acad. Sci. U.S.A.* 83:8107–8111], are modified by replacement of one or more, preferably all three cysteine residues with, for example serine. Replacement may be effected by modification of the DNA encoding the aequorin apoprotein, such as that set forth in SEQ ID No. 5, and replacing the cysteine codons with serine.

The photoproteins and luciferases from related species, such as Obelia are also contemplated for use herein. DNA encoding the $Ca^{2+}$-activated photoprotein obelin from the hydroid polyp *Obelia longissima* is known and available [see, e.g., Illarionov et al. (1995) *Gene* 153:273–274; and Bondar et al. (1995) *Biochim. Biophys. Acta 1231* :29–32]. This photoprotein can also be activated by $Mn^{2+}$ [see, e.g., Vysotski et al. (1995) *Arch. Bioch. Biophys.* 316:92–93, Vysotski et al. (1993) *J. Biolumin. Chemilumin.* 8:301–305].

In general for use herein, the components of the bioluminescence are packaged or provided so that there is insufficient metal ions to trigger the reaction. When used, the trace amounts of triggering metal ion, particularly $Ca^{2+}$ is contacted with the other components. For a more sustained glow, aequorin can be continuously reconstituted or can be added or can be provided in high excess.

(b) Luciferin

The aequorin luciferin is coelenterazine and analogs therein, which include molecules having the structure [formula (I)]:

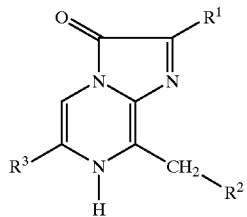

in which $R_1$ is $CH_2C_6H_5$ or $CH_3$; $R_2$ is $C_6H_5$, and $R_3$ is $p-C_6H_4OH$ or $CH_3$ or other such analogs that have activity. Preferred coelenterazine has the structure in which $R^1$ is $p-CH_2C_6H_4OH$, $R_2$ is $C_6H_5$, and $R_3$ is $p-C_6H_4OH$, which can be prepared by known methods [see, e.g., Inouye et al. (1975) *Jap. Chem. Soc., Chemistry Lttrs.* pp 141–144; and Halt et al. (1979) *Biochemistry* 18:2204–2210]. Among the preferred analogs, are those that are modified, whereby the spectral frequency of the resulting light is shifted to another frequency.

The preferred coelenterazine has the structure (formula (II)):

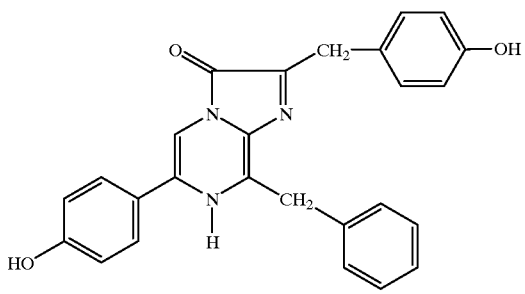

and sulfated derivatives thereof.

The reaction of coelenterazine when bound to the aequorin photoprotein with bound oxygen and in the presence of $Ca^{2+}$ can represented as follows:

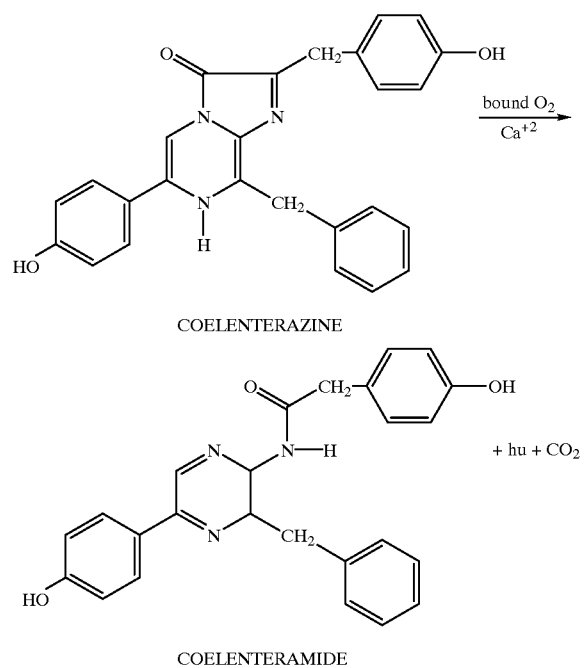

The photoprotein aequorin [which contains apoaequorin bound to a coelenterate luciferin molecule] and Renilla luciferase, discussed below, can use the same coelenterate luciferin. The aequorin photoprotein catalyses the oxidation of coelenterate luciferin [coelenterazine] to oxyluciferin [coelenteramide] with the concomitant production of blue light [$lambda_{max}$=469 nm].

Importantly, the sulfate derivative of the coelenterate luciferin [lauryl-luciferin] is particularly stable in water, and thus may be used in a coelenterate-like bioluminescent system. In this system, adenosine diphosphate (ADP) and a sulpha-kinase are used to convert the coelenterazine to the sulphated form. Sulfatase is then used to reconvert the lauryl-luciferin to the native coelenterazine. Thus, the more stable lauryl-luciferin is used in the item to be illuminated and the luciferase combined with the sulfatase are added to the luciferin mixture when illumination is desired.

Thus, the bioluminescent system of Aequorea is particularly suitable for use in the methods herein. The particular amounts and the manner in which the components are provided depends upon the type of neoplasia or specialty tissue to be visualized. This system can be provided in lyophilized form, that will glow upon addition of $Ca^{2+}$. It can be encapsulated, linked to microcarriers, such as microbeads, or in as a compositions, such as a solution or suspension, preferably in the presence of sufficient chelating agent to prevent triggering the reaction. The concentration of the aequorin photoprotein will vary and can be determined empirically. Typically concentrations of at least 0.1 mg/l, more preferably at least 1 mg/l and higher, will be selected. In certain embodiments, 1–10 mg luciferin/100 mg of luciferase will be used in selected volumes and at the desired concentrations will be used.

(2) The Renilla System

Representative of coelenterate systems is the Renilla system. Renilla, also known as sea pansies, are members of the class of coelenterates Anthozoa, which includes other bioluminescent genera, such as Cavarnularia, Ptilosarcus, Stylatula, Acanthoptilum, and Parazoanthus. Bioluminescent members of the Anthozoa genera contain luciferases and luciferins that are similar in structure [see, e.g., Cormier et al. (1973) *J. Cell. Physiol.* 81:291–298; see, also Ward et al. (1975) *Proc. Natl. Acad. Sci. U.S.A.* 72:2530–2534]. The luciferases and luciferins from each of these anthozoans crossreact with one another and produce a characteristic blue luminescence.

Renilla luciferase and the other coelenterate and ctenophore luciferases, such as the aequorin photoprotein, use imidazopyrazine substrates, particularly the substrates generically called coelenterazine [see, formulae (I) and (II), above]. Other genera that have luciferases that use a coelenterazine include: squid, such as Chiroteuthis, Eucleoteuthis, Onychoteuthis, Watasenia, cuttlefish, Sepiolina; shrimp, such as Oplophorus, Acanthophyra, Sergestes, and Gnathophausia; deep-sea fish, such as Argyropelecus, Yarella, Diaphus, Gonadostomias and Neoscopelus.

Renilla luciferase does not, however, have bound oxygen, and thus requires dissolved oxygen in order to produce light in the presence of a suitable luciferin substrate. Since Renilla luciferase acts as a true enzyme [i.e., it does not have to be reconstituted for further use] the resulting luminescence can be long-lasting in the presence of saturating levels of luciferin. Also, Renilla luciferase is relatively stable to heat.

Renilla luciferase, DNA encoding Renilla luciferase, and use of the DNA to produce recombinant luciferase, as well as DNA encoding luciferase from other coelenterates, are well known and available [see, e.g., SEQ ID No. 1, U.S. Pat. Nos. 5,418,155 and 5,292,658; see, also, Prasher et al. (1985) *Biochem. Biophys. Res. Commun.* 126:1259–1268; Cormier (1981) "Renilla and Aequorea bioluminescence" in *Bioluminescence and Chemiluminescence,* pp. 225–233; Charbonneau et al. (1979) *J. Biol. Chem.* 254:769–780; Ward et al. (1979) *J. Biol. Chem.* 254:781–788; Lorenz et al. (1981) *Proc. Natl. Acad. Sci. U.S.A.* 88:4438–4442; Hori et al. (1977) *Proc. Natl. Acad. Sci. U.S.A.* 74:4285–4287; Hori et al. (1975) *Biochemistry* 14:2371–2376; Hori et al. (1977) *Proc. Natl. Acad. Sci. U.S.A.* 74:4285–4287; Inouye et al. (1975) *Jap. Soc. Chem. Lett.* 141–144; and Matthews et al. (1979) *Biochemistry* 16:85–91]. The DNA encoding Renilla luciferase and host cells containing such DNA provide a convenient means for producing large quantities of the enzyme [see, e.g., U.S. Pat. Nos. 5,418,155 and 5,292,658, which describe recombinant production of Renilla luciferase and the use of the DNA to isolate DNA encoding other luciferases, particularly those from related organisms].

When used herein, the Renilla luciferase can be packaged in lyophilized form, encapsulated in a vehicle, either by itself or in combination with the luciferin substrate. Prior to use the mixture is contacted with an aqueous composition, preferably a phosphate buffered saline pH 7–8; dissolved $O_2$ will activate the reaction. Final concentrations of luciferase in the glowing mixture will be on the order of 0.01 to 1 mg/l or more. Concentrations of luciferin will be at least about $10^{-8}$ M, but 1 to 100 or more orders of magnitude higher to produce a long lasting bioluminescence.

In certain embodiments herein, about 1 to 10 mg, or preferably 2–5 mg, more preferably about 3 mg of coelenterazine will be used with about 100 mg of Renilla luciferase. The precise amounts, of course can be determined empirically, and, also will depend to some extent on the ultimate concentration and application. In particular, about addition of about 0.25 ml of a crude extract from the bacteria that express Renilla to 100 ml of a suitable assay buffer and about 0.005 μg was sufficient to produce a visible and lasting glow [see, U.S. Pat. Nos. 5,418,155 and 5,292,658, which describe recombinant production of Renilla luciferase].

Lyophilized mixtures, and compositions containing the Renilla luciferase are also provided. The luciferase or mixtures of the luciferase and luciferin may also be encapsulated into a suitable delivery vehicle, such as a liposome, glass particle, capillary tube, drug delivery vehicle, gelatin, time release coating or other such vehicle. The luciferase may also be linked to a substrate, such as biocompatible materials.

c. Crustacean, Particularly Cyrpidina Systems

The ostracods, such as *Vargula serratta, hilgendorfii* and *noctiluca* are small marine crustaceans, sometimes called sea fireflies. These sea fireflies are found in the waters off the coast of Japan and emit light by squirting luciferin and luciferase into the water, where the reaction, which produces a bright blue luminous cloud, occurs. The reaction involves only luciferin, luciferase and molecular oxygen, and, thus, is very suitable for application herein.

The systems, such as the Vargula bioluminescent systems, are particularly preferred herein because the components are stable at room temperature if dried and powdered and will continue to react even if contaminated. Further, the bioluminescent reaction requires only the luciferin/luciferase components in concentrations as low as 1:40 parts per billion to 1:100 parts per billion, water and molecular oxygen to proceed. An exhausted system can renewed by addition of luciferin.

(1) Vargula luciferase

The Vargula luciferase is water soluble and is among those preferred for use in the methods herein. Vargula luciferase is a 555-amino acid polypeptide that has been produced by isolation from Vargula and also using recombinant technology by expressing the DNA in suitable bacterial and mammalian host cells [see, e.g., Thompson et al. (1989) *Proc. Natl. Acad. Sci. U.S.A.* 86:6567–6571; Inouye et al. (1992) *Proc. Natl. Acad. Sci. U.S.A.* 89:9584–9587; Johnson et al. (1978) *Methods in Enzymology LVII*:331–349; Tsuji et al. (1978) *Methods Enzymol.* 57:364–72; Tsuji (19740 *Biochemistry* 13:5204–5209; Japanese Patent Application No. JP 3–30678 Osaka; and European Patent Application No. EP 0 387 355 A1].

(a) Purification from Cypridina

Methods for purification of Vargula [Cypridina] luciferase are well known. For example, crude extracts containing the active can be readily prepared by grinding up or crushing the Vargula shrimp. In other embodiments, a preparation of *Cypridina hilgendorfi* luciferase can be prepared by immersing stored frozen *C. hilgendorfi* in distilled water containing, 0.5–5.0 M salt, preferably 0.5–2.0 M sodium or potassium chloride, ammonium sulfate, at 0–30° C., preferably 0–10° C., for 1–48 hr, preferably 10–24 hr, for extraction followed by hydrophobic chromatography and then ion exchange or affinity chromatography [TORAY IND INC, Japanese patent application JP 4258288, published Sep. 14, 1993; see, also, Tsuji et al. (1978) *Methods Enzymol.* 57:364–72 for other methods].

The luciferin can be isolated from ground dried Vargula by heating the extract, which destroys the luciferase but leaves the luciferin intact [see, e.g., U.S. Pat. No. 4,853,327].

(b) Preparation by Recombinant Methods

The luciferase is preferably produced by expression of cloned DNA encoding the luciferase [European Patent Application No. 0 387 355 A1; International PCT Application No. WO 95/001542; see, also SEQ ID No. 5, which sets forth the sequence from Japanese Patent Application No. JP 3-30678 and Thompson et al. (1989) *Proc. Natl. Acad. Sci. U.S.A.* 86:6567–6571] DNA encoding the luciferase or variants thereof is introduced into *E. coli* using appropriate vectors and isolated using standard methods.

(2) Vargula luciferin

The natural luciferin in a substituted imidazopyrazine nucleus, such a compound of formula (III):

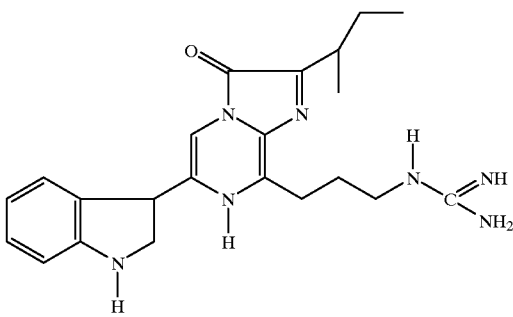

Analogs thereof and other compounds that react with the luciferase in a light producing reaction also may be used.

Other bioluminescent organisms that have luciferases that can react with the Vargula luciferin include, the genera Apogon, Parapriacanthus and Porichthys.

(3) Reaction

The luciferin upon reaction with oxygen forms a dioxetanone intermediate [which includes a cyclic peroxide similar to the firefly cyclic peroxide molecule intermediate]. In the final step of the bioluminescent reaction, the peroxide breaks down to form $CO_2$ and an excited carbonyl. The excited molecule then emits a blue to blue-green light.

The optimum pH for the reaction is about 7. For purposes herein, any pH at which the reaction occurs may be used. The concentrations of reagents are those normally used for analytical reactions or higher [see, e.g., Thompson et al. (1990) *Gene* 96:257–262]. Typically concentrations of the luciferase between 0.1 and 10 mg/l, preferably 0.5 to 2.5 mg/l will be used. Similar concentrations or higher concentrations of the luciferin may be used.

d. Insect Bioluminescent Systems Including Fireflies, Click beetles, and other Insect System The biochemistry of firefly bioluminescence was the first bioluminescent system to be characterized [see, e.g., Wienhausen et al. (1985) *Photochemistry and Photobiology* 42:609–611; McElroy et al. (1966) in *Molecular Architecture in cell Physiology,* Hayashi et al., eds. Prentice Hall, Inc., Englewood Cliffs, N.J., pp. 63–80] and it is commercially available [e.g., from Promega Corporation, Madison, Wis., see, e.g., Leach et al. (1986) *Methods in Enzymology* 133:51–70, esp. Table 1]. Luciferases from different species of fireflies are antigenically similar. These species include members of the genera Photinus, Photurins and Luciola. Further, the bioluminescent reaction produces more light at 30° C. than at 20° C., the luciferase is stabilized by small quantities of bovine albumin serum, and the reaction can be buffered by tricine.

(1) Luciferase

DNA clones encoding luciferases from various insects and the use to produce the encoded luciferase is well known. For example, DNA clones that encode luciferase from *Photinus pyralis, Luciola cruciata* [see, e.g., de Wet et al. (1985) *Proc. Natl. Acad. Sci. U.S.A.* 82:7870–7873; de We et al. (1986) *Methods in Enzymolog* 133:3; U.S. Pat. No. 4,968,613, see, also SEQ ID No. 3] are available. The DNA has also been expressed in Saccharomyces [see, e.g., Japanese Application No. JP 63317079, published Dec. 26, 1988, KIKKOMAN CORP] and in tobacco.

In addition to the wild-type luciferase modified insect luciferases have been prepared. For example, heat stable luciferase mutants, DNA-encoding the mutants, vectors and transformed cells for producing the luciferases are available. A protein with 60% amino acid sequence homology with luciferases from *Photinus pyralis, Luciola mingrelica, L. cruciata* or *L. lateralis* and having luciferase activity is available [see, e.g., International PCT Application No. WO 95/25798]. It is more stable above 30° C. than naturally-occurring insect luciferases and may also be produced at 37° C. or above, with higher yield.

Modified luciferases that generate light at different wavelengths [compared with native luciferase], and thus, may be selected for their color-producing characteristics. For example, synthetic mutant beetle luciferase(s) and DNA encoding such luciferases that produce bioluminescence at a wavelength different from wild-type luciferase are known [Promega Corp, International PCT Application No. WO 95/18853, which is based on U.S. application Ser. No. 08/177,081]. The mutant beetle luciferase has an amino acid sequence differing from that of the corresponding wild-type *Luciola cruciata* [see, e.g., U.S. Pat. Nos. 5,182,202, 5,219, 737, 5,352,598, see, also SEQ ID No.3] by a substitution(s) at one or two positions. The mutant luciferase produces a bioluminescence with a wavelength of peak intensity that differs by at least 1 nm from that produced by wild-type luciferases.

Other mutant luciferase have also been produced. Mutant luciferases with the amino acid sequence of wild-type luciferase, but with at least one mutation in which valine is replaced by isoleucine at the amino acid number 233, valine by isoleucine at 239, serine by asparagine at 286, glycine by serine at 326, histidine by tyrosine at 433 or proline by serine at 452 are known [see, e.g., U.S. Pat. Nos. 5,219,737, and 5,330,906]. The luciferases are produced by expressing DNA-encoding each mutant luciferase in *E. coli* and isolating the protein. These luciferases produce light with colors that differ from wild-type. The mutant luciferases catalyze luciferin to produce red [λ609 nm and 612 nm], orange [λ595 and 607 nm] or green [λ558 nm] light. The other physical and chemical properties of mutant luciferase are substantially identical to native wild type-luciferase. The mutant luciferase has the amino acid sequence of *Luciola cruciata* luciferase with an alteration selected from Ser 286 replaced by Asn, Gly 326 replaced by Ser, His 433 replaced by Tyr or Pro 452 replaced by Ser. Thermostable luciferases are also available [see, e.g., U.S. Pat. No. 5,229,285; see, also International PCT Application No. WO 95/25798, which provides Photinus luciferase in which the glutamate at position 354 is replaced lysine and Luciola luciferase in which the glutamate at 356 is replaced with lysine].

These mutant luciferases as well as the wild type luciferases are among those preferred herein, particularly in instances when a variety of colors are desired or when stability at higher temperatures is desired.

(2) Luciferin

The firefly luciferin is a benzothiazole:

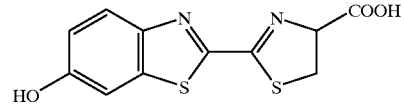

Analogs of this luciferin and synthetic firefly luciferins are also known to those of skill in art [see, e.g., U.S. Pat. No. 5,374,534 and 5,098,828]. These include compounds of formula (IV) [see, U.S. Pat. No. 5,098,828]:

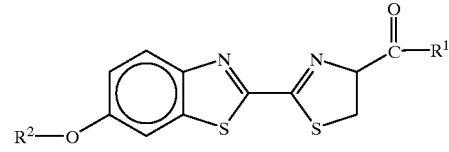

in which:

$R^1$ is hydroxy, amino, linear or branched $C_1$–$C_{20}$ alkoxy, $C_2$–$C_{20}$ alkyenyloxy, an L-amino acid radical bond via the α-amino group, an oligopeptide radical with up to ten L-amino acid units linked via the α-amino group of the terminal unit;

$R^2$ is hydrogen, $H_2PO_3$, $HSO_3$, unsubstituted or phenyl substituted linear or branched $C_1$–$C_{20}$ alkyl or $C_2$–$C_{20}$alkenyl, aryl containing 6 to 18 carbon atoms, or $R^3$—C(O)—; and $R^3$ is an unsubstituted or phenyl substituted linear or branched $C_1$–$C_{20}$ alkyl or $C_2$–$C_{20}$alkenyl, aryl containing 6 to 18 carbon atoms, a nucleotide radical with 1 to 3 phosphate groups, or a glycosidically attached mono- or disaccharide, except when formula (IV) is a D-luciferin or D-luciferin methyl ester.

Modified luciferins that have been modified to produce light of shifted frequencies are known to those of skill in the art.

(3) Reaction

The reaction catalyzed by firefly luciferases and related insect luciferases requires ATP, $Mg^{2+}$ as well as molecular oxygen. Luciferin must be added exogenously. Firefly luciferase catalyzes the firefly luciferin activation and the subsequent steps leading to the excited product. The luciferin reacts with ATP to form a luciferyl adenylate intermediate. This intermediate then reacts with oxygen to form a cyclic luciferyl peroxy species, similar to that of the coelenterate intermediate cyclic peroxide, which breaks down to yield $CO_2$ and an excited state of the carbonyl product. The excited molecule then emits a yellow light; the color, however, is a function of pH. As the pH is lowered the color of the bioluminescence changes from yellow-green to red.

Different species of fireflies emit different colors of bioluminescence so that the color of the reaction will be dependent upon the species from which the luciferase is obtained. Additionally, the reaction is optimized at pH 7.8.

Addition of ATP and luciferin to a reaction that is exhausted produces additional light emission. Thus, the system, once established, is relatively easily maintained. Therefore, it is highly suitable for use herein in embodiments in which a sustained glow is desired.

e. Bacterial Systems

Luminous bacteria typically emit a continuous light, usually blue-green. When strongly expressed, a single bacterium may emit $10^4$ to $10^5$ photons per second. Bacterial bioluminescence systems include, among others, those systems found in the bioluminescent species of the genera Photobacterium, Vibrio and Xenorhabdus. These systems are well known and well characterized [see, e.g., Baldwin et al. (1984) *Biochemistry* 23:3663–3667; Nicoli et al. (1974) *J. Biol. Chem.* 249:2393–2396; Welches et al. (1981) *Biochemistry* 20:512–517; Engebrecht et al. (1986) *Methods in Enzymology* 133:83–99; Frackman et al. (1990) *J. of Bacteriology* 172:5767–5773; Miyamoto et al. (1986) *Methods in Enzymology* 133:70; U.S. Pat. No. 4,581,335].

(1) Luciferases

Bacterial luciferase, as exemplified by luciferase derived from *Vibrio harveyi* [EC 1.14.14.3, alkanol reduced-FMN-oxygen oxidoreductase 1-hydroxylating, luminescing], is a mixed function oxidase, formed by the association of two different protein subunits α and β. The α-subunit has an apparent molecular weight of approximately 42,000 kD and the β-subunit has an apparent molecular weight of approximately 37,000 kD [see, e.g., Cohn et al. (1989) *Proc. Natl. Acad. Sci. U.S.A.* 90:102–123]. These subunits associate to form a 2-chain complex luciferase enzyme, which catalyzes the light emitting reaction of bioluminescent bacteria, such as *Vibrio harveyi* [U.S. Pat. No. 4,581,335; Belas et al. (1982) *Science* 218:791–793], *Vibrio fischeri* [Engebrecht et al. (1983) *Cell* 32:773–781; Engebrecht et al. (1984) *Proc. Natl. Acad. Sci. U.S.A.* 81:4154–4158] and other marine bacteria.

Bacterial luciferase genes have been cloned [see, e.g., U.S. Pat. No. 5,221,623; U.S. Pat. No. 4,581,335; European Patent Application No. EP 386 691 A]. Plasmids for expression of bacterial luciferase, such as *Vibrio harveyi*, include pFIT001 (NRRL B-18080), pPALE001 (NRRL B-18082) and pMR19 (NRRL B-18081)] are known. For example the sequence of the entire lux regulon from *Vibiro fisheri* has been determined [Baldwin et al. (1984), *Biochemistry* 23:3663–3667; Baldwin et al. (1981) *Biochem.* 20:512–517; Baldwin et al. (1984) *Biochem.* 233663–3667; see, also, e.g., U.S. Pat. Nos. 5,196,318, 5,221,623, and 4,581,335]. This regulon includes luxI gene, which encodes a protein required for autoinducer synthesis [see, e.g., Engebrecht et al. (1984) *Proc. Natl. Acad. Sci. U.S.A.* 81:4154–4158], the luxC, luxD, and luxE genes, which encode enzymes that provide the luciferase with an aldehyde substrate, and the luxA and luxB genes, which encode the alpha and beta subunits of the luciferase.

Lux genes from other bacteria have also been cloned and are available [see, e.g., Cohn et al. (1985) *J. Biol. Chem.* 260:6139–6146; U.S. Pat. No. 5,196,524, which provides a fusion of the luxA and luxB genes from *Vibrio harveyi*]. Thus, luciferase alpha and beta subunit-encoding DNA is provided and can be used to produce the luciferase. DNA encoding the α [1065 bp] and β [984 bp] subunits, DNA-encoding a luciferase gene of 2124 bp, encoding the alpha and beta subunits, a recombinant vector containing DNA encoding both subunits and a transformed *E. coli* and other bacterial hosts for expression and production of the encoded luciferase are available. In addition, bacterial luciferases are commercially available.

(2) Luciferins

Bacterial luciferins include:

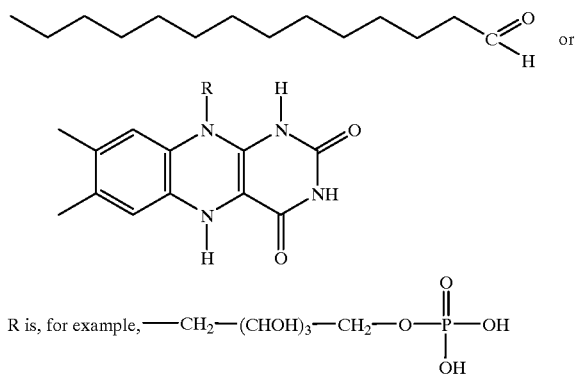

R is, for example, $-CH_2-(CHOH)_3-CH_2-O-\overset{\overset{\displaystyle O}{\|}}{\underset{\underset{\displaystyle OH}{|}}{P}}-OH$ in which the tetradecanal with reduced flavin mononucleotide are considered luciferin since both are oxidized during the light emitting reaction.

(3) Reactions

The bacterial systems require, in addition to reduced flavin, five polypeptides to complete the bioluminescent reaction: two subunits, α and β, of bacterial luciferin and three units of a fatty acid reductase system complex, which supplies the tetradecanal aldehyde. Examples of bacterial bioluminescent systems useful in the apparatus and methods provided herein include those derived from *Vibrio fisheri* and *Vibrio harveyi*. One advantage to this system is its ability to operate at cold temperatures; certain surgical procedures are performed by cooling the body to lower temperatures.

Bacterial luciferase catalyzes the flavin-mediated hydroxylation of a long-chain aldehyde to yield carboxylic acid and an excited flavin; the flavin decays to ground state with the concomitant emission of blue green light [$\lambda_{max}$=490 nm; see, e.g., Legocki et al. (1986) *Proc. Natl. Acad. Sci. USA* 81:9080; see U.S. Pat. No. 5,196,524]:

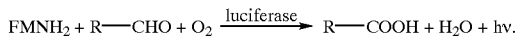

The reaction can be initiated by contacting reduced flavin mononucleotide [$FMNH_2$] with a mixture of the bacterial luciferase, oxygen, and a long-chain aldehyde, usually n-decyl aldehyde.

DNA encoding luciferase from the fluorescent bacterium Alteromonas hanedai is known [CHISSO CORP; see, also, Japanese application JP 7222590, published Aug. 22, 1995]. The reduced flavin mononucleotide [$FMNH_2$; luciferin] reacts with oxygen in the presence of bacterial luciferase to produce an intermediate peroxy flavin. This intermediate reacts with a long-chain aldehyde [tetradecanal] to form the acid and the luciferase-bound hydroxy flavin in its excited state. The excited luciferase-bound hydroxy flavin then emits light and dissociates from the luciferase as the oxidized flavin mononucleotide [FMN] and water. In vivo FMN is reduced again and recycled, and the aldehyde is regenerated from the acid.

Flavin reductases have been cloned [see, e.g., U.S. Pat. No. 5,484,723; see, SEQ ID No. 14 for a representative sequence from this patent]. These as well as NAD(P)H can be included in the reaction to regenerate $FMNH_2$ for reaction with the bacterial luciferase and long chain aldehyde. The flavin reductase catalyzes the reaction of FMN, which is the luciferase reaction, into $FMNH_2$; thus, if luciferase and the reductase are included in the reaction system, it is possible to maintain the bioluminescent reaction. Namely, since the bacterial luciferase turns over many times, bioluminescence continues as long as a long chain aldehyde is present in the reaction system.

The color of light produced by bioluminescent bacteria also results from the participation of a protein blue-florescent protein [BFP] in the bioluminescence reaction. This protein, which is well known [see, e.g., Lee et al. (1978) Methods in Enzymology LVII:226–234], may also be added to bacterial bioluminescence reactions in order to cause a shift in the color.

f. Other Systems (1) Dinoflagellate Bioluminescence Generating Systems

In dinoflagellates, bioluminescence occurs in organelles termed scintillons. These organelles are outpocketings of the cytoplasm into the cell vacuole. The scintillons contain only dinoflagellate luciferase and luciferin [with its binding protein], other cytoplasmic components being somehow excluded. The dinoflagellate luciferin is a tetrapyrrole related to chlorophyll:

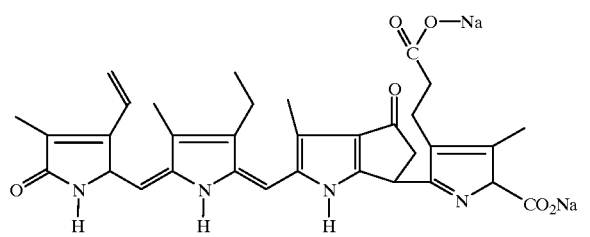

or an analog thereof.

The luciferase is a 135 kD single chain protein that is active at pH 6.5, but inactive at pH 8 [see, e.g., Hastings (1981) Bioluminescence and Chemiluminescence, DeLuca et al., eds. Academic Press, NY, pp.343–360]. Luminescent activity can be obtained in extracts made at pH 8 by simply shifting the pH from 8 to 6. This occurs in soluble and particulate fractions. Within the intact scintillon, the luminescent flash occurs for ~100 msec, which is the duration of the flash in vivo. In solution, the kinetics are dependent on dilution, as in any enzymatic reaction. At pH 8, the luciferin is bound to a protein [luciferin binding protein] that prevents reaction of the luciferin with the luciferase. At pH 6, however, the luciferin is released and free to react with the enzyme.

(2) Systems from Molluscs, such as Latia and Pholas

Molluscs Latia neritoides and species of Pholas are bioluminescent animals. The luciferin has the structure:

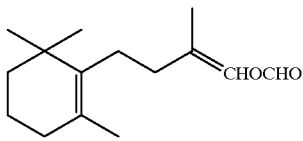

and has been synthesized [see, e.g., Shimomura et al. (1968) Biochemistry 7:1734–1738; Shimomura et al. (1972) Proc. Natl. Acad. Sci. U.S.A. 69:2086–2089]. In addition to a luciferase and luciferin the reaction has a third component, a "purple protein". The reaction, which can be initiated by an exogenous reducing agent is represented by the following scheme:

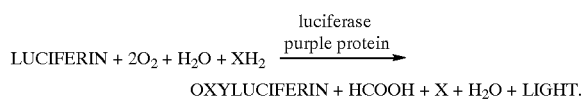

$XH_2$ is a reducing agent.

Thus for practice herein, the reaction will require the purple protein as well as a reducing agent.

(3) Earthworms and Other Annelids

Earthworm species, such as Diplocardia longa, Chaetopterus and Harmothoe, exhibit bioluminescence. The luciferin has the structure:

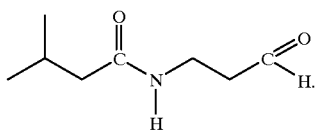

The reaction requires hydrogen peroxide in addition to luciferin and luciferase. The luciferase is a photoprotein.

(4) Glow Worms

The luciferase/luciferin system from the glow worms that are found in Great Britain, and in Australian and New Zealand caves are also intended for use herein.

(5) Marine Polycheate Worm Systems

Marine polycheate worm bioluminescence generating systems, such as Phyxotrix and Chaetopterus, are also contemplated for use herein.

(6) South American Railway Beetle

The bioluminescence generating system from the South American railway beetle is also intended for use herein.

(7) Fish

Of interest herein, are luciferases and bioluminescence generating systems that generate red light. These include luciferases found in species of Aristostomias, such as A. scintillans [see, e.g., O'Day et al. (1974) Vision Res. 14:545–550], Pachystomias, Malacosteus, such as M. niger.

Blue/green emmitters include cycithone, myctophids, hatchet fish (agyropelecus), vinciguerria, howella, florenciella, and Chauliodus.

g. Other Fluorescent Proteins

(1) Green and Blue Fluorescent Proteins

As described herein, blue light is produced using the Renilla luciferase or the Aequorea photoprotein in the presence of $Ca^{2+}$ and the coelenterazine luciferin or analog thereof. This light can be converted into a green light if a green fluorescent protein (GFP) is added to the reaction. Green fluorescent proteins, which have been purified [see, e.g., Prasher et al. (1992) *Gene* 111:229–233] and also cloned [see, e.g., International PCT Application No. WO 95/07463, which is based on U.S. application Ser. No. 08/119,678 and U.S. application Ser. No. 08/192,274, which are herein incorporated by reference], are used by cnidarians as energy-transfer acceptors. GFPs fluoresce in vivo upon receiving energy from a luciferase-oxyluciferin excited-state complex or a $Ca^{2+}$-activated photoprotein. The chromophore is modified amino acid residues within the polypeptide. The best characterized GFPs are those of Aequorea and Renilla [see, e.g., Prasher et al. (1992) *Gene* 111:229–233; Hart, et al. (1979)*Biochemistry* 18:2204–2210]. For example, a green fluorescent protein [GFP] from *Aequorea Victoria* contains 238 amino acids, absorbs blue light and emits green light. Thus, inclusion of this protein in a composition containing the aequorin photoprotein charged with coelenterazine and oxygen, can, in the presence of calcium, result in the production of green light. Thus, it is contemplated that GFPs may be included in the bioluminescence generating reactions that employ the aequorin or Renilla luciferases or other suitable luciferase in order to enhance or alter color of the resulting bioluminescence.

GFPs are activated by blue light to emit green light and thus may be used in the absence of luciferase and in conjunction with an external light source to illuminate neoplaisa and specialty tissues, as described herein. Similarly, blue fluorescent proteins (BFPs), such as from *Vibrio fischeri, Vibrio harveyi* or *Photobacterium phosphoreum,* may be used in conjunction with an external light source of appropriate wavelength to generate blue light. (See for example, Karatani, et al., "A blue fluorescent protein from a yellow-emitting luminous bacterium," *Photochem. Photobiol.* 55(2):293–299 (1992); Lee, et al., "Purification of a blue-fluorescent protein from the bioluminescent bacterium *Photobacterium phosphoreum*" *Methods Enzymol.* (Biolumin. Chemilumin.) 57: 226–234 (1978); and Gast, et al. "Separation of a blue fluorescence protein from bacterial luciferase" *Biochem. Biophys. Res. Commun.* 80(1):14–21 (1978), each incorporated in its entirety by reference herein.) In particular, GFPs, and/or BFPs or other such fluorescent proteins may be used in the methods described herein using a targeting agent conjugate by illuminating the conjugate with light of an appropriate wavelength to cause the fluorescent proteins to fluoresce.

Such systems are particularly of interest because no luciferase is needed to activate the photoprotein. These fluorescent proteins may also be used in addition to bioluminescence generating systems to enhance or create an array of different colors.

(2) Phycobiliproteins

Phycobiliproteins are water soluble fluorescent proteins derived from cyanobacteria and eukaryotic algae [see, e.g., Apt et al. (1995) *J. Mol. Biol.* 238:79–96; Glazer (1982) *Ann. Rev. Microbiol.* 36:173–198; and Fairchild et al. (1994) *J. of Biol. Chem.* 269:8686–8694]. These proteins have been used as fluorescent labels in immmunoassay [see, Kronick (1986) *J. of Immunolog. Meth.* 92:1–13], the proteins have been isolated and DNA encoding them is also available [see, e.g., Pilot et al. (1984) *Proc. Natl. Acad. Sci. U.S.A.* 81:6983–6987; Lui et al. (1993) *Plant Physiol* 103:293–294; and Houmard et al. (1988) *J. Bacteriol.* 170:5512–5521; the proteins are commercially available from, for example, ProZyme, Inc., San Leandro, Calif.].

In these organisms, the phycobiliproteins are arranged in subcellular structures termed phycobilisomes, and function as accessory pigments that participate in photosynthetic reactions by absorbing visible light and transferring the derived energy to chlorophyll via a direct fluorescence energy transfer mechanism.

Two classes of phycobiliproteins are known based on their color: phycoerythrins (red) and phycocyanins (blue), which have reported absorbtion maxima between 490 and 570 nm and between 610 and 665 nm, respectively. Phycoerythrins and phycocyanins are heterogenous complexes composed of different ratios of alpha and beta monomers to which one or more class of linear tetrapyrrole chromophores are covalently bound. Particular phycobiliproteins may also contain a third γ-subunit which often associated with $(\alpha\beta)_6$ aggregate proteins.

All phycobiliproteins contain either phycothrombilin or phycoerythobilin chromophores, and may also contain other bilins phycourobilin, cryptoviolin or the 697 nm bilin. The γ-subunit is covalently bound with phycourobilin which results in the 495–500 nm absorbtion peak of B- and R-phycoerythrins. Thus, the spectral characteristics of phycobiliproetins may be influenced by the combination of the different chromophores, the subunit composition of the apophycobiliproteins and/or the local environment effecting the tertiary and quaternary structure of the phycobiliproteins.

As described above for GFPs and BFPs, phycobiliproteins are also activated by visible light of the appropriate wavelength and, thus, may be used in the absence of luciferase and in conjunction with an external light source to illuminate neoplaisa and specialty tissues, as described herein. Furthermore, the attachment of phycobiliproteins to solid support matrices is known (e.g., see U.S. Pat. Nos. 4,714,682; 4,767,206; 4,774,189 and 4,867,908). As noted above, these proteins may be used in combination with other fluorescent proteins and/or bioluminescence generating systems to produce an array of colors or to provide different colors over time.

As described above, attachment of phycobiliproteins to solid support matrices is known (e.g., see U.S. Pat. Nos. 4,714,682; 4,767,206; 4,774,189 and 4,867,908). Therefore, phycobiliproteins may be coupled to microcarriers coupled to one or more components of the bioluminescent reaction, preferably a luciferase, to convert the wavelength of the light generated from the bioluminescent reaction. Microcarriers coupled to one or more phycobiliproteins may be used in any of the methods provided herein.

The conversion of blue or green light to light of a longer wavelength, i.e., red or near infra-red, is particularly preferred for the visualization of deep neoplasias or specialty tissues using a laparoscope or computer tomogram imaging system, as described herein.

Thus, when a change in the frequency of emitted light is desired, the phycobiliprotein, or other spectral shifter, such as synthetic fluorochrome, green fluorescent proteins, red fluorescent proteins, and substrates altered chemically or enzymatically to cause shifts in frequency of emission can be included with the bioluminescent generating components.

2. Linkers

Any linker known to those of skill in the art may be used herein. Other linkers are suitable for incorporation into chemically produced conjugates. Linkers that are suitable for chemically linked conjugates include disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid diihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. (1993) *Molecular Immunol. 30*:379–386). In some embodiments, several linkers may be included in order to take advantage of desired properties of each linker.

Chemical linkers and peptide linkers may be inserted by covalently coupling the linker to the TA and the targeted agent. The heterobifunctional agents, described below, may be used to effect such covalent coupling. Peptide linkers may also be linked by expressing DNA encoding the linker and TA, linker and targeted agent, or linker, targeted agent and TA as a fusion protein.

Flexible linkers and linkers that increase solubility of the conjugates are contemplated for use, either alone or with other linkers are contemplated herein.

Numerous heterobifunctional cross-linking reagents that are used to form covalent bonds between amino groups and thiol groups and to introduce thiol groups into proteins, are known to those of skill in this art (see, e.g., the PIERCE CATALOG, ImmunoTechnology Catalog & Handbook, 1992–1993, which describes the preparation of and use of such reagents and provides a commercial source for such reagents; see, also, e.g., Cumber et al. (1992) *Bioconjugate Chem. 3*:397–401; Thorpe et al. (1987) *Cancer Res. 47*:5924–5931; Gordon et al. (1987) *Proc. Natl. Acad Sci. 84*:308–312; Walden et al. (1986) *J. Mol. Cell Immunol. 2*:191–197; Carlsson et al. (1978) *Biochem. J. 173*:723–737; Mahan et al. (1987) *Anal. Biochem. 162*:163–170; Wawryznaczak et al. (1992) *Br. J. Cancer 66*:361–366; Fattom et al. (1992) *Infection & Immun. 60*:584–589). These reagents may be used to form covalent bonds between the TA and targeted agent. These reagents include, but are not limited to: N-succinimidyl-3-(2-pyridyldithio)propionate (SPDP; disulfide linker); sulfosuccinimidyl 6-[3-(2-pyridyldithio)propionamido]-hexanoate (sulfo-LC-SPDP); succinimidyloxycarbonyl-α-methyl benzyl thiosulfate (SMBT, hindered disulfate linker); succinimidyl 6-[3-(2-pyridyidithio) propionamido]hexanoate (LC-SPDP); sulfo-succinimidyl 4-(N-maleimidomethyl)cyclohexane-1-carboxylate (sulfo-SMCC); succinimidyl 3-(2-pyridyldithio)-butyrate (SPDB; hindered disulfide bond linker); sulfosuccinimidyl 2-(7-azido-4-methylcoumarin-3-acetamide) ethyl-1,3'-dithiopropionate (SAED); sulfo-succinimidyl 7-azido-4-methylcoumarin-3-acetate (SAMCA); sulfosuccinimidyl 6-[alpha-methyl-alpha-(2-pyridyidithio)toluamido]-hexanoate (sulfo-LC-SMPT); 1,4-di-[3'-(2'-pyridyidithio)propionamido]butane (DPDPB); 4-succinimidyloxycarbonyl-α-methyl-α-(2-pyridylthio)toluene (SMPT, hindered disulfate linker); sulfosuccinimidyl6[α-methyl-α-(2-pyridyidithio)toluamido]hexanoate (sulfo-LC-SMPT); m-maleimidobenzoyl-N-hydroxysuccinimide ester (MBS); m-maleimidoben-zoyl-N-hydroxysulfosuccinimide ester (sulfo-MBS); N-succinimidyl(4-iodoacetyl)aminobenzoate (SIAB; thioether linker); sulfosuccinimidyl(4-iodoacetyl) amino benzoate (sulfo-SIAB); succinimidyl4(p-maleimidophenyl)butyrate (SMPB); sulfosuccinimidyl4-(p-maleimidophenyl)butyrate (sulfo-SMPB); azidobenzoyl hydrazide (ABH).

Acid cleavable linkers, photocleavable and heat sensitive linkers may also be used, particularly where it may be necessary to cleave the targeted agent to permit it to be more readily accessible to reaction. Acid cleavable linkers include, but are not limited to, bismaleimideothoxy propane; and adipic acid dihydrazide linkers (see, eg., Fattom et al. (1992) *Infection & Immun. 60*:584–589) and acid labile transferrin conjugates that contain a sufficient portion of transferrin to permit entry into the intracellular transferrin cycling pathway (see, e.g., Welhöner et al. (1991) *J. Biol. Chem. 266:*4309–4314).

Photocleavable linkers are linkers that are cleaved upon exposure to light (see, e.g., Goldmacher et al. (1992) *Bioconi. Chem. 3:*104–107, which linkers are herein incorporated by reference), thereby releasing the targeted agent upon exposure to light. Photocleavable linkers that are cleaved upon exposure to light are known (see, e.g., Hazum et al. (1981) in *Pept., Proc. Eur. Pept. Symp., 16th,* Brunfeldt, K (Ed), pp. 105–110, which describes the use of a nitrobenzyl group as a photocleavable protective group for cysteine; Yen et al. (1989) *Makromol. Chem 190:*69–82, which describes water soluble photocleavable copolymers, including hydroxypropylmethacrylamide copolymer, glycine copolymer, fluorescein copolymer and methylrhodamine copolymer; Goldmacher et al. (1992) *Bioconi. Chem. 3:*104–107, which describes a cross-linker and reagent that undergoes photolytic degradation upon exposure to near UV light (350 nm); and Senter et al. (1985) *Photochem. Photobiol 42:*231–237, which describes nitrobenzyloxycarbonyl chloride cross linking reagents that produce photocleavable linkages), thereby releasing the targeted agent upon exposure to light. Such linkers would have particular use in treating dermatological or ophthalmic conditions that can be exposed to light using fiber optics. After administration of the conjugate, the eye or skin or other body part can be exposed to light, resulting in release of the targeted moiety from the conjugate. Such photocleavable linkers are usefule in connection with diagnostic protocols in which it is desirable to remove the targeting agent to permit rapid clearance from the body of the animal.

3. Targeting Agents

Targeting agents include any agent that will interact with and localize the targeted agent cells in a tumor or specialized tissue [targeted tissue]. Such agents include any agent that specifically interacts with a cell surface protein or receptor that is present at sufficiently higher concentrations or amounts on the targeted tissue, whereby, when contacted with an appropriate bioluminescence generating reagent and activators. These agents include, but are not limited to, growth factors, preferentially modified to not internalize, methotrexate, and antibodies, particularly, antibodies raised against tumor specific antigens. A plethora of tumor-specific antigens have been identified from a number of human neoplasias. Among the antigens suitable for use in raising antibodies are those set forth in Table 3. below.

Anti-tumor Antigen Antibodies

Polyclonal and monoclonal antibodies may be produced against selected antigens. Alternatively, many such antibodies are presently available. An exemplary list of antibodies and the tumor antigen for which each has been directed against is provided in Table 3. It is contemplated that any of the antibodies listed may be conjugated with a bioluminescence generating component following the methods provided herein.

TABLE 3

| Antigen | Immunizing Tissue | Antibody | Reference |
|---|---|---|---|
| Oncofetal | | | |
| OPA | Fetal pancreas | Rabbit, polyclonal | Knapp, (1981)[1] |
| CEA | Colon, Rectal, Stomach, Lung, Pancreas, Kidney, Bladder, Head & Neck, Cervical, endometrial, ovarian, Breast | Rabbit sheep monkey (polyclonal) monoclonal FO23C5 A10 MN14 F(ab)2 11.285.14 14.95.55 | Burtin and Gold, (1978)[2] Prall et al., (1996)[116] Ballesta et al. (1995)[129] Rowland et al., (1985)[115] |
| POA | Fetal pancreas | Rabbit, polyclonal | Gelder, et al. (1978)[3] |
| FAP | Fetal pancreas | Mouse, MAb J28 | Escribano and Albers, (1986)[4] |
| PA8-15 | Pancreatic cancer cell line SUIT-2 | Mouse, MAb PA8-15 | Arai, et al. (1991)[5] |
| Adult | | | |
| CA 50 | Colorectal carcinoma cell line | Mouse MAb C 50 | Lindholm, et al. (1983)[6] |
| CA 19-9 | Colon carcinoma cell line SW1116 | Mouse MAb 19-9 | Koprowski et al (1979)[7] |
| CA 242 | Colorectal carcinoma cell line COLO 205 | Mouse MAb C 242 | Haglund, et al. (1989)[8] |
| CAR-3 | Epidermoid carcinoma cell line A 431 | Mouse MAb AR-3 | Prat, et al. (1989)[9] |
| DU-PAN-2 | Pancreatic carcinoma cell line HPAF | Mouse MAb DU-PAN-2 | Lan, et al. (1987)[10] |
| Ypan-1 | Pancreatic carcinoma cell line SW1990 | Mouse MAb Ypan-1 | Yvan, et al. (1985)[11] |
| Span-1 | Pancreatic carcinoma cell line SW1990 | Mouse MAb Span-1 | Yvan, et al. (1985)[11] |
| BW494 | Pancreatic tumor tissue | Mouse MAb BW494 | Bosslet, et al. (1986)[12] |
| MUSE 11 | Gastric cancer ascites fluid | Mouse MAb MUSE 11 | Ban, et al.(1989)[13] |
| $L_{A1}$ | Embryonal carcinoma cells | Rettig et al. (1985)[14] Fukuda et al. (1986)[15] | Fukuda et al. (1986)[15] |
| $Le^a$ FUC-$L_{A1}$ | Colon adenocarcinoma Pancreatic adenocarcinoma | Blaszcyk et al. (1985)[16] Martensson et al. (1988)[17] | Hakomori and Andrews (1970)[18] Blaszcyk et al. (1985)[16] Tempero et al. (1987)[19] |
| $Le^b$ | Colon adenocarcinoma Pancreatic adenocarcinoma | Brockhaus et al. (1981)[31] Blaszcyk et al. (1985)[16] | Hakomori and Andrews (1970)[18] Blaszcyk et al. (1985)[16] Tempero et al. (1987)[19] |

TABLE 3-continued

| Antigen | Immunizing Tissue | Antibody | Reference |
|---|---|---|---|
| 3-iso$L_{M1}$ | Small cell lung carcinoma<br>Glioma<br>MedulJoblastoma<br>Teratocarcinoma cells | Nilsson et al. (1985a)[20]<br>Rettig et al. (1985)[14]<br>Fredman et al. (1990a)[21]<br>Wikstrand et al. (1991)[22] | Nilsson et al. (1985a)[20]<br>Fredman et al. (1990a)[23]<br>Gottfries et al. (1990)[24]<br>Fukuda et al. (1986)[14] |
| 3',6'-iso$L_{D1}$ | Liver metastasis of colon cancer<br>Embryonal carcinoma cells | Fukushi et al. (1986)[25]<br>Wikstrand et al. (1991)[22] | Fukushi et al. (1986)[25]<br>Fukuda et al. (1986)[14] |
| Fuc-3'-iso$L_{M1}$<br>Sialylated Le$^a$ | Gastrointestinal cancer | Koprowski et al. (1979)[26]<br>Magnani et al. (1982)[27]<br>Chia et al. (1985)[28] | Koprowski et al. (1979)[28]<br>Magnani et al. (1982)[27]<br>Chia et al. (1985)[28]<br>Mansson et al. (1985)[29] |
| Fuc-3',6'-iso$L_{D1}$<br>Disialylated Le$^a$ | Human colon adenocarcinoma | Nudelman et al. (1986)[30] | Nudelman et al. (1986)[30] |
| n$L_{A1}$<br>i-Antigen | Colon cancer<br>Lung cancer | Myoga et al. (1988)[32]<br>Hirohashi et al. (1986)[33] | Myoga et al. (1988)[32]<br>Hirohashi et al. (1986)[33] |
| SSEA-1<br>Le$^x$<br>Fuc-n$L_{A1}$ | Teratocarcinoma<br>Colon cancer | Brockhaus et al. (1982)[34]<br>Magnani et al. (1982)[27]<br>Fukushi et al. (1984a)[35]<br>Urdal et al.(1983)[36] | Solter and Knowles (1978)[38] |
| Dimeric Le$^x$ | Adenocarcinoma<br>Colon cancer<br>Liver cancer | Fukushi et al. (1984a,b)[35&37]<br>Hakomori et al. (1984)[39] | Fukushi et al. (1984b)[37] |
| Le$^7$ | Gastric cancer<br>Breast cancer<br>Colon cancer | Abe et al. (1983)[40] | Abe et al. (1983)[40]<br>Brown et al. (1983)[41]<br>Lloyd et al. (1983)[42] |
| 6'-$L_{M1}$ | Colorectal carcinoma<br>Lung carcinomas<br>Primary hepatoma | Nilsson et al. (1985b)[43]<br>Taki et al. (1990)[44] | Nilsson et al. (1985b)[43]<br>Taki et al. (1990)[44] |
| Sialylated Le$^x$ or Fuc-3'-$L_{M1}$ | Gastrointestinal cancer<br>Lung carcinoma | Fukushima et al. (1984)[45] | Fukushima et al. (1984)[45] |
| | Gastric<br>colon<br>lung<br>breast<br>renal cancers | Fukushi et al. (1985)[46] | Fukushi et al. (1984b)[37] |
| GB3<br>Globo-H | Burkitt's lymphoma<br>breast cancer | Weils et al. (1981)[47]<br>Menard et al. (1983)[48] Bremer et al. (1984)[49] | Wiels et al. (1981)[47]<br>Menard et al. (1983)[48] |
| Sulfatide | Mucinous cystadenocarcinoma, | Fredman et al. (1988a)[50] | Kiguchi et al. (1992)[51] |
| Disulfated $G_{A1}$ | Hepatocellular carcinoma | Hiraiwa et al. (1985)[53] | Hiraiwa et al. (1985)[53] |
| N-Glycolylneura | Colon cancer | Higashi et al. (1985)[53] | Higashi et al. (1985)[53] |

TABLE 3-continued

| Antigen | Immunizing Tissue | Antibody | Reference |
|---|---|---|---|
| minic acid | | | Kawai et al.55 |
| N-Glycolyl-$G_{M2}$ | N-Glycolyl-$G_{M2}$ | Miyake et al. (1990)[54] | Miyake et al. (1990)[54] |
| $G_{M2}$ | Melanoma | Tai et al.(1983)[56] Natoli et al. (1986)[57] | Irie et al. (1982)[60] Tai et al. (1983)[56] Tsuchida et al. |
| | Fredman et al. | (1987 a,b)[61&62] (1989)[58] | |
| OFA-I-1 OFA-I-2 | | | Cahan et al., 1982[64] |
| | Glioma | Vrionis et al. (1989)[59] | Fredman et al. (1986b)[63] |
| | Germ cell tumors | | Miyake et al. (1990)[54] |
| $G_{D2}$ | Melanoma | Cahan et al. (1982)[64] | Cahan et al. (1982)[64] |
| | Neuroblastoma | Cheung et al., (1985)[65] Bosslet et al. (1989)[66] | Schulz et al. (1984)[67] Wu et al. (1986)[68] |
| | Small cell lung carninoma | Longee et al. (1991)[69] | Cheung et al. (1985)[65] Cheresh et al. (1986a)[70] |
| | Glioma | | Fredman et al. (1986b)[63] |
| $G_{M3}$ | Melanoma | Wakabayashi et al. (1984)[71] Hirabayashi et al. (1986)[72] | Tsuchida et al. (1987a,b)[61&62] Yamamato et al. (1990)[74] Furukawa |
| Ag FCM1 2–39 1F43 | | Yamaguchi et al. (1987)[73] | et al. (1989)[75] Usuba et al., 1988[117] |
| $G_{D3}$ | Melanoma | Pukel et al. (1982)[76] | Pukel et al. (1982)[76] |
| HJM1 | Melanoma | Nudelman et al. (1982)[77] | Nudelman et al. (1982)[77] |
| | Medulloblastoma | He et al. (1989)[78] | Gottfries et al. (1990)[80] |
| | Glioma | Brodin et al. (1985)[78] Yamaguchi et al. (1987)[72] | Fredman et al. (1986a, 1988b)[63&85] |
| | Leukemia | Furukawa et al. (1989)[75] | Siddique et al. (1984)[81] |
| | Meninglioma | | Davidson et al. (1989)[82] |
| 9-O-Acetyl-$G_{D3}$ | Melanoma | Cheresh et al. (1984b)[84] | Cheresh et al. (1984b,c)[83] |
| Fuc-$G_{M1}$ | Small cell lung carcinoma | Fredman et al. (1986a)[86] | Nilsson et al. (1986)[87] |
| COTA | Colon, ovarian | Mouse SP21 | Pant et al. (1986)[88] |
| SW1038 CTS | Colon prostate | Mouse Mab 17-1A | Shaw et al. (1987)[89] Tempero et al. (1990)[90] |
| MAGE-1 MAGE-2 MAGE-3 (MZ2-EMZ2-Bb) | Lung melanocyte breast | | Toso et at. (1996)[91] Russo et al. (1995)[92] |
| MUC-1 | Breast pancreas | | Domenech et al. (1995)[93] |
| Lewis-Ag (GICA) | Ovarian myelin | | Stroussan et al. (1992)[94] |
| TAG-12 | Breast ovarian | | Schmitt (1994)[95] |
| TAG-72 | colon ovarian pancrease | | Paterson et al. (1986)[96] |
| Orfan-specific cancer neoantigen (OSN) | Lung | | Dubois et al. (1985)[97] |
| GP100 | Melanocyte | | Bakker et al. (1993)[95] |
| MART-1 | Melanocyte | | Kawakaui et al. (1994)[99] |

TABLE 3-continued

| Antigen | Immunizing Tissue | Antibody | Reference |
|---|---|---|---|
| p95/p97 | Melanocyte | | Furukawa et al. (1989)[100] |
| EGF receptor | Squamous tumors | | Masui et al., (1986) Ozanne et al. (1986)[101&102] |
| CA125 | Ovary | OC125 | Bast et al. (1983)[104] |
| | Breast | DF3 | Metzgar (1984)[105] |
| p97 (melanotransferrin) | Melanocyte | | Rose et al. (1986)[106] |
| 22-1-1 | uterus cervix ovary | | Sonoda et al. (1986)[107] |
| GA733 | gastrointestinal carcinoma | GA733MoAb | Linnebach et al. (1989)[109] |
| YH206 | adenocarcinomas | YH206MoAb | Hinoda et al. (1985)[110] |
| MART-2 | melanocytes | | Sensi et al. (1995)[111] |
| BAGE-1 | melanocytes | | Boel et al.(1995)[112] |
| GAGE1-6 | melaocyte | | Vand en Eynde et al. (1995)[113] |
| | osteocarcoma | Mab 791T/36 | Embleton et al. (1984)[118] |
| DF3 | Breast | | Hayes et al. (1985)[119] |
| | lymphocytes | IDEC-Y2B8 IDEC-C-C2B8 | Bioworld Today[120] |
| L3p40-50 | Lung | L3 | Brezicka and Olling (1994)[121] |
| L3p90 Thomsen-Friedenrich Pan Tumor Antigen | pancarcinoma | A78-G/A7 | Tinari et al. Karsten et al. (1995)[114] |
| | pancreas | TURP-27 TURP-73 | Starling et al.[122] |
| | ovarian | OV-TL 3 139H2 | Molthoff et al.[123] |
| EPB-2 | B cell lymphoma | LL2 | Siegel et al.[124] |
| | melanoma | ZME-018 | Koizumi et al.[125] |
| | lymphoma | N9-127 | Kondo et al.[126] |
| | medullary thyroid carcinoma | MIBG | Hilditch et al.[127] |
| | gastrointestinal carcinoma | MU-9 | Sharkey et al.[129] |
| NS-ESO-1 | melanoma, breast, bladder, prostate, heptocellular carcinoma | NY-ESO-1 | Tinari et al.[130] |
| NY-ESO-1 | melanoma, breast, bladder, prostate, heptocellular carcinoma | (HOM-MEL-40) SS X2 | Tinari et al.[130] |

[1] Knapp ML. (1981) Ann Clin Biochem 18:131.
[2] Butin B. et al. (1978) Scand J Immunol 8, Suppl.8:27.
[3] Gelder FB. et al. (1978) Cancer Res 38:313.
[4] Escribano MJ. et al. (1986) Int J Cancer 38:155.
[5] Arai M. et al. (1990) Jpn J Clin Oncol 20:145.
[6] Lindholm L. et al. (1983) Int Arch Allergy Appl Immunol 71:178.
[7] Koprowski H. et al. (1979) Somat Cell Genet 5:957.
[8] Haglund C. et al. (1989) Br J Cancer 60:845.
[9] Prat M. etaA (1989) Cancer Res 49:1415.
[10] Lan MS. et al. (1987) J Biol Chem 262:12863.
[11] Yvan S. et al. (1985) Cancer Res 45:6179.
[12] Bosslet K. et al. (1986) Cancer Immunol Immunother 23:185.
[13] Ban T. et al. (1989) Cancer Res 49:7141.
[14] Rettig G. et al. (1985) Cancer Res 45:815–821.
[15] Fukuda, M. et al. (1986) J Biol Chem 261:5145–5153.
[16] Blaszczyk M. et al. (1985) Proc. Natl. Acad. Sci. U.S.A. 82:3552–3556
[17] Martensson S. et al. (1988) Cancer Res 48:2125–2131.
[18] Hakomori S. and Andrews H. (1970) Biochim Biophys Acta 202:225–228.

TABLE 3-continued

| Antigen | Immunizing Tissue | Antibody | Reference |
|---------|-------------------|----------|-----------|

[19] Jempero M. et al. (1987) Cancer Res 47:5501–5503.
[20] Nilsson O. et al. (1985a) FEBS Lett 182:398–402.
[21] Fredman P. et al. (1990a) Biochim Biophys Acta 1045:239–244.
[22] Wikstrand CJ. etal (1991) J Neurophathol Exp Neurol 50:756–769.
[23] Fredman P. et al. (1988b) J Neurochem 50:912–919.
[24] Gottfries J. et al. (1990) J Neurochem 55:1322–1326.
[25] Fukushi Y. et al. (1986) Biochemistry 25:2859–2866.
[26] Koprowski H. et al. (1979) Somatic Cell Genet 5:957–972.
[27] Magnani J. et al. (1982) J Biol Chem 257:14365–14369.
[28] Chia et al. (1985) Cancer Res. 45:435–437.
[29] Mansson et al. (1985) Biochim. Biophys. Acta 834:110–117.
[30] Nudelman et al. (1986) J Biol Chem 261:5487–5495
[31] Brockhaus M. et al. (1981) J Biol Chem 256:13223–13225.
[32] Myoga et al. (1988) Cancer Res 48:1512–1516.
[33] Hirohashi et al. (1986) J. Immunol. 136:4163–4168.
[34] Brockhau et al. (1982) Arch. Biochem. Biophys. 127:647–651.
[35] Fukushi, et al. (1984a) J. Biol. Chem. 259:4681:4685.
[36] Urdal, et al. (1983) Blood 62:1022–1026.
[37] Fukushi, et al. (1984b) J. Biol. Chem. 259:10511–10517.
[38] Solter and Knowles (1978) Proc. Natl. Acad. Sci. U.S.A. 75:5565–5569
[39] Hakomori, et al. (1984) J. Biol. Chem. 252:4672–4680.
[40] Abe et al. (1983) J. Biol. Chem. 258:11793–11797.
[41] Brown et al. (1983) Biosci. Rep. 3:163–170.
[42] Lloyd et al. (1983) Immunogenetics (N.Y.) 17:537–541.
[43] Nilsson et al. (1985b) Biochim. Biophys. Acta 835:577–583.
[44] Taki et al. (1990) Cancer Res. 50:1284–1290.
[45] Fukushima et al. (1984) Cancer Res. 44:5279–5285.
[46] Fukushi et al. (1985) Cancer Res. 45:3711–3717.
[47] Wiels et al. (1981) Proc. Natl. Acad. Sci. U.S.A. 78:6485–6488.
[48] Menard et al. (1983) Cancer Res. 43:1295–1300.
[49] Bremer et al. (1984) J. Biol. Chem. 259:14773–14777.
[50] Fredman et al. (1988a) Biochem. J. 251:17–22.
[51] Kiguchi et al. (1992) Cancer Res. 52:416–421.
[52] Hiraiwa et al. (1990) Cancer Res. 50:2917–2928.
[53] Higashi et al. (1985) Cancer Res. 45:3796–3802.
[54] Miyake et al. (1990) Cancer (Philadelphia) 65:499–505.
[55] Kawai et al. (1991) Cancer Res. 51:1242–1246.
[56] Tai et al. (1983) Proc. Natl. Acad. Sci. U.S.A. 80:5392–5396.
[57] Nataoli et al. (1986) Cancer Res. 46:41 1 6–41 20.
[58] Fredman et al. (1989) J. Biol. Chem. 264:12122–12125.
[59] Vrionis et al. (1989) Cancer Res. 49:6641–6649.
[60] Irie et al. (1982) Proc. Natl. Acad. Sci. U.S.A. 79:5666–5670.
[61] Tsuchida etaA (1987a) JNCI J. Natl. Cancer Inst. 78:45–54.
[62] Tsuchida et al. (1987b) Cancer Res. 47:1278–1281.
[63] Fredman et al. (1986b) Neurol. Res. 8:123–126.
[64] Cahan et a/. (1982) Proc. Natl. Acad. Sci. U.S.A. 79:7629–7633.
[65] Cheung eta/ (1985) Cancer Res. 45:2642–2649.
[66] Bossiet al. (1989) Cancer Res. 29:171–178.
[67] Schultz et al. (1984) Cancer Res. 44:5914–5920
[68] Wu et al. (1986) Cancer Res. 46:440–443.
[69] Longee et al. (1991) Acta Neuropathol. 82:45–54.
[70] Cheresh et al. (1986a) Cancer Res. 46:5112–5118.
[71] Wakabayashi et al. (1984) J. Invest. Dermatol. 83:128–133.
[72] Hirabayashi et al. (1986) Bichim. Biophys. Acta 875:126–128.
[73] Yamaguchi et al. (1987) Proc. Natl. Sci. U.S.A. 84:2416–2420.
[74] Yamamoto et al. (1990) J. Natl. Cancer Inst. 82:1757–1760.
[75] Furukawa et al. (1989) Cancer Res. 49:191–196.
[76] Pukel et al. (1982) J. Exp. Med. 155:1133–1147.
[77] Nudelman et al. (1982) J. Biol. Chem 257:12752–12756.
[78] He et al. (1989) Acta Neuropathol. 79:317–325.
[79] Brodin et al. (1985) Biochim. Biophys. Acta. 837:349–353.
[80] Gottfries et al. (1990) J. Neurochem. 55:1322–1326.
[81] Siddique et al. (1984) Cancer Res. 44:5262–5265.
[82] Davidsson et al. (1989) J. Neurochem. 53:705–709.
[83] Cheresh et al. (1984c) Science 225:844–846
[84] Cheresh et al. (1984b) J. Biol. Chem. 259:7453–7459.
[85] Fredman et al. (1988b) J. Neurochem. 50:912–919.
[86] Fredman et al. (1986a) Biochim. Biophys. Acta. 875:316–323.
[87] Nilsson et al. (1986) Cancer Res. 46:1403–1407.
[88] Paul et al. (1986) Hybridoma 5:129–135.
[89] Shaw et aA (1987) J. Immunol. 138:4534–4538.
[90] Tempero et al. (1990) J. Clin. Oncol. 8:2019–2026.
[91] Toso et al. (1996) Cancer Es. 56:16–20.
[92] Russo et al. (1995) Int. J. Cancer P. Oncol. 64:216–221.
[93] Domenech et al. (1995) J. Immunol. 155:4766.
[94] Stroussand et al. (1992) Crit. Rev. Biochem. Mol. Biol. 27:57
[95] Schmitt et al. (1994) Hybridoma 13:389–396.

TABLE 3-continued

| Antigen | Immunizing Tissue | Antibody | Reference |
|---|---|---|---|

[96]Paterson et al. (1986) Int. J. Cancer 37:659
[97]Dubois et al. (1985) Cancer Res. 45:2661.
[98]Bakkeret al. (1993) J. Exp. Med. 179:1005
[99]Kawakaii et al. (1994) J. Exp. Med. 180:347.
[100]Furukawa et al. (1989) J. Exp. Med. 169:585.
[101]Masui et al. (1986) Cancer Res. 46:5592.
[103]Primus et al. (1983) Cancer Res. 43:686.
[104]Bast et al. (1983) Eng. J. Med. 309:883.
[105]Metzgan et al. (1984) PNAS 81:5242
[106]Rose et al. (1986) PNAS 83:1261.
[107]Sonoda et al. (1996) Cancer 77:1501–1509.
[108]Saga et al. (1980) Jpn. J. Cancer Res. 81:1141–1148.
[109]Linnebach et al. (1989) PNAS 86:27–31.
[110]Hinoda et al. (1985) Jpn. J. Cancer Res. 76:1203–1211.
[111]Sensi et al. (1995) PNAS 92:5674–5678.
[112]Boel et al. (1995) Immunity 2:167–175.
[113]Vand en Eynde et al. (1995) J. Exp. Med. 182:689–698.
[114]juweid et al. (1996) Cancer 78:157–168.
[115]Rowland et al. (1985) Cancer Immunol. Immunother. 19:1–17.
[116]Pra11 et al. (1996) J. Histochem. Cytochem. 44:35–41.
[117]Usuba et al. (1988) J. Cancer Res. 79:1340–48.
[118]Embleton et al. (1984) Br. J. Cancer 49:559–565.
[119]Hayes et al. (1985)
[120]Bioworld Today
[121]Brezicka and Olling (1994) Int. J. Cancer Suppl. 8:121–124.
[122]Starling et al. (1986) Cancer Res. 46:367–374.
[123]Molthoff et al (1992) Br. J. Cancer 65:677–683.
[124]Siegel et al. (1991) Antib. Immunoconj. Radiopharm 4:649–654.
[125]Koizumi et al. (1988) Jpn. J. Cancer Res. 79:973–981.
[126]Kondo et al. (1995) J. VioI. 69:6735–6741.
[127]Hilditch et al. (1986) J. Nucl. Med. 27:1150–1153.
[128]Sharkey et al. (1994) Cancer 73:863–877.
[129]Ballesta et al. (1995) Tumor Biol. 16:332–41.
[130]Tinari et al. (1997) Biochem. Biophys. Res. Commun. 232:367–372.

Among the preferred antibodies for use in the methods herein are those of human origin or, more preferably, are humanized monoclonal antibodies. These are preferred for diagnosis of humans.

Preparation of the Conjugates

Any method for linking protiens may be used. For example, methods for linking a luciferase to an antibody is described in U.S. Pat. No. 5,486,455. As noted above, the targeting agent and luciferin or luciferase may be linked directly, such as through covalent bonds, i.e., sulfhyryl bonds or other suitable bonds, or they may be linked through a linker. There may be more than one luciferase or luciferin per targeting agent, or more than one targeting agent per luciferase or luciferin.

Alternatively, an antibody, or $F(Ab)_2$ antigen-binding fragment thereof or other protien targeting agent may be fused (directly or via a linking peptide) to the luciferase using recombinant DNA technology. For example, the DNA encoding any of the anti-tumor antibodies of Table 3 may be ligated in the same translational reading frame to DNA encoding any of the above-described luciferases, e.g., SEQ ID NOs. 1–14 and inserted into an expression vector. The DNA encoding the recombinant antibody-luciferase fusion may be introduced into an appropriate host, such as bacteria or yeast, for expression.

C. Formulation and Administration of the Compositions for Use in the Diagnostic Systems In most embodiments, the components of the diagnostic systems provided herein are formulated into two compositions: a first composition containing the conjugate; and a second composition containing the remaining components of the bioluminescence generating system. The compositions are formulated in any manner suitable for administration to an animal, particularly a mammal, and more particularly a human. Such formulations include those suitable for topical, local, enteric, parenteral, intracystal, intracutaneous, intravitreal, subcutaneous, intramuscular, or intraveneous administration.

For example, the conjugates, which in preferred embodiments, are a targeting agent linked to a luciferase (or photoprotein) are formulated for systemic or local administration. The remaining components are formulated in a separate second composition for topical or local application. The second composition will typically contain any other agents, such as spectral shifters that will be included in the reaction. It is preferred that the components of the second composition are formulated in a time release manner or in some other mantter that prevents degradation and/or interaction with blood components.

The First Composition: Formulation of the Conjugates

As noted above, the conjugates either contain a luciferase or lucifern and a targetting agents. The preferred conjugates are formed between a targetting agent and a luciferase or photoprotein. The conjugates may be formulated into pharmaceutical compositions suitable for topical, local, intravenous and systemic application. Effective concentrations of one or more of the conjugates are mixed with a suitable pharmaceutical carrier or vehicle. The concentrations or amounts of the conjugates that are effective requires delivery of an amount, upon administration, that results in a sufficient amount of targeted moiety linked to the targeted cells or tissue whereby the cells or tissue can be visualized during the surgical procedure. Typically, the compositions are formulated for single dosage administration. Effective concentrations and amounts may be determined empirically by testing the conjugates in known in vitro and in vivo systems, such as those described here; dosages for humans or other animals may then be extrapolated therefrom.

Upon mixing or addition of the conjugate(s) with the vehicle, the resulting mixture may be a solution, suspension, emulsion or the like. The form of the resulting mixture depends upon a number of factors, including the intended mode of administration and the solubility of the conjugate in the selected carrier or vehicle. The effective concentration is sufficient for targeting a sufficient amount of targeted agent to the site of interest, whereby when combined with the remaining reagents during a surgical procedure the site will glow. Such concentration or amount may be determined based upon in vitro and/or in vivo data, such as the data from the mouse xenograft model for tumors or rabbit ophthalmic model. If necessary, pharmaceutically acceptable salts or other derivatives of the conjugates may be prepared.

Pharmaceutical carriers or vehicles suitable for administration of the conjugates provided herein include any such carriers known to those skilled in the art to be suitable for the particular mode of administration. In addition, the conjugates may be formulated as the sole pharmaceutically ingredient in the composition or may be combined with other active ingredients.

The conjugates can be administered by any appropriate route, for example, orally, parenterally, intravenously, intradermally, subcutaneously, or topically, in liquid, semi-liquid or solid form and are formulated in a manner suitable for each route of administration. Intravenous or local administration is presently preferred. Tumors and vascular proliferative disorders, will typically be visualized by systemic, intradermal or intramuscular, modes of administration.

The conjugate is included in the pharmaceutically acceptable carrier in an amount sufficient to produce detectable tissue and to not result in undesirable side effects on the patient or animal. It is understood that number and degree of side effects depends upon the condition for which the conjugates are administered. For example, certain toxic and undesirable side effects are tolerated when trying to diagnose life-threatening illnesses, such as tumors, that would not be tolerated when diagnosing disorders of lesser consequence.

The concentration of conjugate in the composition will depend on absorption, inactivation and excretion rates thereof, the dosage schedule, and amount administered as well as other factors known to those of skill in the art. Typically an effective dosage should produce a serum concentration of active ingredient of from about 0.1 ng/ml to about 50–1000 $\mu$g/ml, preferably 50–100 $\mu$g/ml. The pharmaceutical compositions typically should provide a dosage of from about 0.01 mg to about 100–2000 mg of conjugate, depending upon the conjugate selected, per kilogram of body weight per day. Typically, for intravenous administration a dosage of about between 0.05 and 1 mg/kg should be sufficient. Local application for, such as visualization of ophthalmic tissues or local injection into joints, should provide about 1 ng up to 1000 $\mu$g, preferably about 1 $\mu$g to about 100 $\mu$g, per single dosage administration. It is understood that the amount to administer will be a function of the conjugate selected, the indication, and possibly the side effects that will be tolerated. Dosages can be empirically determined using recognized models.

The active ingredient may be administered at once, or may be divided into a number of smaller doses to be administered at intervals of time. It is understood that the precise dosage and duration of administration is a function of the disease condition being diagnosed and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

The conjugates may be prepared with carriers that protect them against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylacetic acid and others. These are particularly useful for application to the eye for ophthalmic indications following or during surgery in which only a single administration is possible. Methods for preparation of such formulations are known to those skilled in the art.

The conjugates may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The ophthalmic compositions may also include additional components, such as hyaluronic acid. The conjugates may be formulated as aerosols for topical application (see, e.g., U.S. Pat. Nos. 4,044,126, 4,414,209, and 4,364,923).

Also, the compositions for activation of the conjugate in vivo during surgical procedures may be formulated as an aerosol. These compositions contain the activators and also the remaining bioluminescence generating agent, such as luciferin, where the conjugate targets a luciferase, or a luciferase, where the conjugate targets a luciferin, such as coelenterazine.

If oral administration is desired, the conjugate should be provided in a composition that protects it from the acidic environment of the stomach. For example, the composition can be formulated in an enteric coating that maintains its integrity in the stomach and releases the active compound in the intestine. Oral compositions will generally include an inert diluent or an edible carrier and may be compressed into tablets or enclosed in gelatin capsules. For the purpose of oral administration, the active compound or compounds can be incorporated with excipients and used in the form of tablets, capsules or troches. Pharmaceutically compatible binding agents and adjuvant materials can be included as part of the composition.

Tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The conjugates can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials that do not impair the desired action, or with materials that supplement the desired action, such as cisplatin for treatment of tumors.

Finally, the compounds may be packaged as articles of manufacture containing packaging material, one or more conjugates or compositions as provided herein within the packaging material, and a label that indicates the indication for which the conjugate is provided.

The Second Composition

The second composition will include the remaining components of the bioluminescence generating reaction. In preferred embodiments in which these components are administered systemically, the remaining components include the luciferin or substrate, and optionally additional agents, such as spectral shifters. These components, such as the luciferin, can be formulated as described above for the conjugates. In some embodiments, the luciferin or luciferase in this composition will be linked to a protein carrier or other carrier to prevent degradation or dissolution into blood cells or other cellular components.

For embodiments, in which the second composition is applied locally or topically, they can be formulated in a spray or aerosol or other suitable means for local or topical application.

In certain embodiments described herein, all components, except an activator are formulated together, such as by encapsulation in a time release formulation that is targetted to the tissue. Upon release the composition will have been localized to the desired site, and will begin to glow.

In practice, the two compositions can be administered simultaneously or sequentially. Typically, the first composition, which contains the conjugate is administered first, generally an hour or two before the surgery, and the second composition is then administered, either preoperatively or during surgery.

D. Practice of the Reactions in Combination with Targeting Agents

The particular manner in which each bioluminescence system will be combined with a selected targeting agent will be a function of the agent and the neoplasia or tissue to be visualized. In general, however, a luciferin or luciferase, of the reaction will be conjugated to the targeting agent, administered to an animal prior to surgery. During the surgery, the tissues of interest are contacted with the remaining component(s) of a bioluminescence generating system. Any tissue to which or with which the targeting agent reacts will glow.

Any color of visible light produced by a bioluminescence generating system is contemplated for use in the methods herein. Preferably the visible light is a combination of blue, green and/or red light of varying intensities and wavelengths. For visualizing neoplasia or specialty tissues through mammalian tissues or tumors deeply embedded in tissue, longer wavelengths of visible light, i.e., red and near infrared light, is preferred because wavelengths of near infrared light of about 700–1300 nm are known to penetrate soft tissue and bone [e.g., see U.S. Pat. No. 4,281,645].

In the simplest embodiments, the targeting agent conjugate may be visualized by adding one or more of the bioluminescence generating components in crude mixture. For example, the organisms can be ground up and dried and administered topically. Light will be emitted by ground up fireflies when mixed with water and ATP. Light will also be emitted by combining ground up Vargula shrimp and adding water, preferably cool water [room temperature or lower]. The only caveat is that the water must not be too hot; high temperatures destroy activity of the luciferases.

Generally, the remaining bioluminescence generating components will be formulated in a vehicle suitable for topical administration to tissues during surgery and will be applied as an aerosol. Alternatively, they can be injected into the tissue or administered intravenously.

In other embodiments, the conjugate can be applied to the tissues during surgery, such as by spraying a sterile solution over the tissues, followed by application of the remaining components. Tissues that express the targeted antigen will glow.

The reagents may be provided in compositions, such as suspensions, as powders, as pastes or any in other suitable sterile form. They may be provided as sprays, aerosols, or in any suitable form. The reagents may be linked to a matrix, particularly microbeads suitable for in vivo use and of size that they pass through capillaries. Typically all but one or more, though preferably all but one, of the components necessary for the reaction will be mixed and provided together; reaction will be triggered contacting the mixed component(s) with the remaining component(s), such as by adding $Ca^{2+}$, FMN with reductase, $FMNH_2$, ATP, air or oxygen.

In preferred embodiments the luciferase or luciferase/luciferin, such as the aequorin photoprotein, will be provided in combination with the targeting agent before administration to the patient. The targeting agent conjugate will then be contacted in vivo with the remaining components. As will become apparent herein, there are a multitude of ways in which each system may be combined with a selected targeting agent.

E. Kits and Compositions

Kits containing the diagnostic systems are provided. The kits comprise compositions containing the conjugates and remaining bioluminescence generating system components. The first composition in the kit typically contains the targeting agent conjugated to a luciferase (i.e., a luciferase or photoprotein). The second composition, contains at least the luciferin (substrate). Both compositions are formulated for systemic, local or topical application to a mammal. In alternative embodiments, the first composition contains the luciferin linked to a targeting agent, and the second composition contains the luciferase.

In general, the packaging is non-reactive with the compositions contained therein and where needed should exclude water and or air to the degree those substances are required for the luminescent reaction to proceed.

Diagnostic applications may require specific packaging. The bioluminescence generating reagents may be provided in pellets, encapsulated as micro or macro-capsules, linked to matrices, preferably biocompatible, more preferably biodegradable matrices, and included in or on articles of manufacture, or as mixtures in chambers within an article of manufacture or in some other configuration. For example, a composition containing luciferase conjugate will be provided separately from, and for use with, a separate composition containing a bioluminescence substrate and bioluminescence activator.

Similarly, the luciferase or luciferin may be provided in a composition that is a mixture, suspension, solution, powder, paste or other suitable composition separately from or in combination with the remaining components, but in the absence of an activating component. Upon contacting the conjugate, which has been targeted to a selected tissue, with this composition the reaction commences and the tissue glows. The luciferase and bioluminescence substrate, for example, are packaged to exclude water and/or air, the bioluminescence activator. Upon administration and release at the targeted site, the reaction with salts or other components at the site, including air in the case of surgical procedures, will activate the components.

1. Dispensing and Packaging Apparatus for Combination with the Bioluminescent System Components The kits may include a bioluminescent apparatus systems provided herein are bioluminescence [or bioluminescent] systems in combination with dispensing or packaging apparatus. The bioluminescence systems, described in detail elsewhere herein, include three components: a bioluminescence substrate [e.g., a luciferin], a luciferase [e.g., a luciferase or photoprotein], and a bioluminescence activator or activators [e.g., molecular oxygen or $Ca^{2+}$]. The dispensing and packaging apparatus are configured to keep at least one of the three components separate from the other two components, until generation of bioluminescence is desired. Detailed descriptions of such apparatus are described in copending, commonly owned U.S. application Ser. Nos. 08/757,046 and 08/597,274, which are incorporated by reference herein.

Two of the components will be mixed to form a suitable composition for targeting to tissues, and the third, will be administered when visualization or detection is desired.

In general, the dispensing and packaging apparatus are non-reactive with the bioluminescent system components contained therein and can exclude moisture, air or other activators, such as $O_2$ or $Ca^{2+}$, or in some manner keep all necessary components that are required for the bioluminescent reaction to come into contact until desired.

2. Capsules, Pellets, Liposomes, Endosomes, Vacuoles, Micronized Particles

In certain embodiments sequestering of the components of one of the compositions from the environment prior to use or provision of the components in particulate form, such as microparticles, may be necessary. Examples of suitable means for such use include encapsulating bioluminescent generating system components in one or micro- [up to about 100 μm in size] or macroparticles [larger than 100 μM] of material that permits release of the contents, such as by diffusion or by dissolution of the encapsulating material. Microparticles to which a plurality of conjugates can be linked are among the preferred embodiments. The microparticles are biocompatible and preferably of a size that can pass through capillary walls.

Liposomes and other encapsulating vehicles [see, e.g., U.S. Pat. No. 4,525,306, which describes encapsulation of compounds in gelatin; U.S. Pat. Nos. 4,021,364, 4,225,581, 4,269,821, 4,322,311, 4,324,683, 4,329,332, 4,525,306, 4,963,368 describe encapsulation of biologically active materials in various polymers] known to those of skill in the art, including those discussed herein and known to those of skill in the art [such as soluble paper, see U.S. Pat. No. 3,859,125].

a. Encapsulating Vehicles in General

All components of the bioluminescence generating system, except for the oxygen or water or $Ca^{2+}$, depending upon the selected system can be incorporated into encapsulating material, such as liposomes, that protect the contents from the environment until placed into conditions that cause release of the contents into the environment. Encapsulating material contemplated for use herein includes liposomes and other such materials used for encapsulating chemicals, such as drug delivery vehicles.

b. Encapsulating Vehicles—Liposomes

For example, liposomes that dissolve and slowly release the components into the medium, such as the blood, which contains dissolved oxygen or $Ca^{2+}$ or even ATP for the luciferase system are contemplated herein. They can be formulated in compositions, such as solutions, suspensions, gels, lotions, creams, and ointments, for topical application, such as procedures for diagnosing or visualizing melanomas. Liposomes and other slow release encapsulating compositions are well known and can be adapted for use in for slow release delivery of bioluminescence generating components. Typically the luciferin and luciferase will be encapsulated in the absence of oxygen or $Ca^{2+}$ or ATP or other activating component. Upon release into the environment or medium containing this component at a suitable concentration, the reaction will proceed and a glow will be produced. Generally the concentrations of encapsulated components should be relatively high, perhaps 0.1–1 mg/ml or more, to ensure high enough local concentrations upon release to be visible.

Liposomes or other sustained release delivery system that are formulated in an ointment or sustained release topical vehicle, for example, would be suitable for use in a body paint, lotion. Those formulated as a suspension would be useful as a spray. Numerous ointments and suitable liposome formulations are known [see, e.g., Liposome Technology, Targeted Drug Delivery and Biological Interaction, vol. III, G. Gregoriadis ed., CRC Press, Inc., 1984; U.S. Pat. Nos. 5,470,881; 5,366,881; 5,296,231; 5,272,079; 5,225,212; 5,190,762; 5,188,837; 5,188,837; 4,921,757; 4,522,811]. For example, an appropriate ointment vehicle would contain petrolatum, mineral oil and/or anhydrous liquid lanolin. Sustained release vehicles such as liposomes, membrane or contact lens delivery systems, or gel-forming plastic polymers would also be suitable delivery vehicles. Liposomes for topical delivery are well known [see, e.g., U.S. Pat. No. 5,296,231; Mezei et al. (1980) "Liposomes—A selective drug delivery system for the topical route of administration, I. lotion dosage form" *Life Sciences 26:*1473–1477; Mezei et al. (1981) "Liposomes—A selective drug delivery system for the topical route of administration: gel dosage form" *Journal of Pharmacy and Pharmacology 34:*473–474; Gesztes et al. (1988) "Topical anaesthesia of the skin by liposome—encapsulated tetracaine" *Anesthesia and Analgesia 67:*1079–1081; Patel (1985) "Liposomes as a controlled-release system",*Biochemical Soc. Trans. 13:*513–516; Wohlrab et al. (1987) "Penetration kinetics of liposomal hydrocortisone in human skin" *Dermatologica 174:*18–22].

Liposomes are microcapsules [diameters typically on the order of less than 0.1 to 20 µm] that contain selected mixtures and can slowly release their contents in a sustained release fashion. Targeted liposomes or other capsule, particularly a time release coating, that dissolve upon exposure to oxygen, air, moisture, visible or ultraviolet [UV] light or a particular pH or temperature [see, e.g., U.S. Pat. No. 4,882,165; Kusumi et al. (1989) *Chem. Lett.* no.*3* 433–436; Koch Troels et al. (1990) *Bioconjupate Chem. 4:*296–304; U.S. Pat. No. 5,482,719; U.S. Pat. No. 5,411,730; U.S. Pat. No. 4,891,043; Straubinger et al. (1983) *Cell 32:*1069–1079; and Straubinger et al. (1985) *FEBS Lttrs. 179:*148–154; and Duzgunes et al. in Chapter 11 of the book CELL FUSION, edited by A. E. Sowers; Ellens et al. (1984) *Biochemistry 23:*1532–1538; Yatvin et al. (1987) *Methods in Enzymology 149:*77–87] may be used. Liposome formulations for use in baking [see, e.g., U.S. Pat. No. 4,999,208] are available. They release their contents when eaten or heated. Such liposomes may be suitable for intravenous or local administration.

Liposomes be prepared by methods known to those of skill in the art [see, e.g., Kimm et al. (1983) *Bioch. Bioph. Acta 728:*339–398; Assil et al. (1987) *Arch Ophthalmol. 105:*400; and U.S. Pat. No. 4,522,811, and other citations herein and known to those of skill in the art].

Liposomes that are sensitive to low pH [see, e.g., U.S. Pat. No. 5,352,448, 5,296,231; 5,283,122; 5,277,913, 4,789,633] are particularly suitable for use with alkaline agents. Upon contact with the low pH detergent or soap composition or a high pH composition, the contents of the liposome will be released. Other components, particularly $Ca^+$ or the presence of dissolved $O_2$ in the water will cause the components to glow as they are released. Temperature sensitive liposomes are also suitable for use in bath powders for release into the warm bath water.

c. Encapsulating Vehicles—Gelatin and Polymeric Vehicles

Macro or microcapsules made of gelatin or other such polymer that dissolve or release their contents on contact with air or light or changes in temperature may also be used to encapsulate components of the bioluminescence generating systems.

Such microcapsules or macrocapsules may also be conjugated to a targeting agent, e.g., an antibody, such that the bioluminescence generating components are delivered to the target by the antibody and then the components are released to produce a glow.

The aequorin system is particularly suitable for this application. It can be encapsulated in suspension or solution or as a paste, or other suitable form, of buffer with sufficient chelating agent, such as EDTA, to prevent discharge of the bioluminescence. Upon exposure of the capsule [microcapsule or macrocapsule] to moisture that contains $Ca^{2+}$, such as in a buffer or blood, the released components will glow.

Thus, encapsulated bioluminescence generating components can be used in combination with a variety of targeting agents and thereby release the luciferase/luciferin, such as the Renilla system, which will light upon exposure to air], and other such items.

Other encapsulating containers or vehicles for use with the bioluminescence systems are those that dissolve sufficiently in water to release their contents, or that are readily opened when squeezed in the hand or from which the contents diffuse when mixed with a aqueous mixture. These containers can be made to exclude water, so that the bioluminescent system components may be desiccated and placed therein. Upon exposure to water, such as in an aqueous composition solution or in the atmosphere, the vehicle dissolves or otherwise releases the contents, and the components react and glow. Similarly, some portion less than all of the bioluminescence generating components may themselves be prepared in pellet form. For example, the component(s) may be mixed with gelatin or similar hardening agent, poured into a mold, if necessary and dried to a hard, water soluble pellet. The encapsulating containers or vehicles may be formed from gelatin or similar water soluble material that is biocompatible.

d. Endosomes and Vacuoles

Vehicles may be produced using endosomes or vacuoles from recombinant host cells in which the luciferase is expressed using method known to those of skill in the art [see, e.g., U.S. Pat. Nos. 5,284,646, 5,342,607, 5,352,432, 5,484,589, 5,192,679, 5,206,161, and 5,360,726]. For example, aequorin that is produced by expression in a host, such as *E. coli*, can be isolated within vesicles, such as endosomes or vacuoles, after protein synthesis. Using routine methods the cells are lysed and the vesicles are released with their contents intact. The vesicles will serve as delivery vehicles. When used they will be charged with a luciferin, such as a coelenterazine, and dissolved oxygen, such as by diffusion, under pressure, or other appropriate means.

e. Micronized Particles

The bioluminescence generating system components that are suitable for lyophilization, such as the aequorin photoprotein, the Renilla system, and the Vargula systems, can be micronized to form fine powder and stored under desiccating conditions, such as with a desiccant. Contact with dissolved oxygen or $Ca^{2+}$ in the air or in a mist that can be supplied or in added solution will cause the particles to dissolve and glow.

3. Immobilized Systems a. Matrix Materials

In some embodiments, it will be desirable to provide at least one component of the bioluminescence generating system linked to a matrix substrate, which can then be locally or systemically administered. The matrix substrate will be biocompatible. When desired, a mixture or mixtures (s) containing the remaining components, typically a liquid mixture is applied, as by pouring or spraying onto the matrix substrate, to produce a glow. For example, the aequorin photoprotein, including coelenterazine and oxygen, is linked to the substrate. When desired a liquid containing $Ca^{2+}$, such as tap water or, preferably, a liquid mixture containing the $Ca^{2+}$ in an appropriate buffer, is contacted, such as by spraying, with the matrix with linked luciferase. Upon contacting the material glows.

In other embodiments, the luciferase, such as a Vargula luciferase, is linked to the substrate material, and contacted with a liquid mixture containing the luciferin in an appropriate buffer. Contacting can be effected by spraying or pouring or other suitable manner. The matrix material is incorporated into, onto or is formed into an article of manufacture, such as surgical sponge or as part of a microbead.

The kits may also include containers containing compositions of the linked components which can be provided in a form, such as sprayed on as a liquid and air dried, that can be applied to the substrate so that the item can be made to glow again. Thus, kits containing a first composition containing the targeting agent and a luciferase or a luciferin or both and luciferin, and a second composition containing the remaining components. The item as provided in the kit can be charged with the first composition, such as having the composition applied and dried, or may require charging prior to the first use. Alternatively, the item may be sprayed with both compositions when desired to produce a glow.

It is understood that the precise components and optimal means for application or storage are a function of the selected bioluminescence system. The concentrations of the components, which can be determined empirically, are not critical, but must be sufficient to produce a visible glow when combined. Typical concentrations are as low as nanomoles/l, preferably on the order of mg/l or higher. The concentration on the substrate is that produced when a composition containing such typical concentration is applied to the material. Again, such ideal concentrations can be readily determined empirically by applying the first composition, letting it dry, spraying the second composition, and observing the result.

The matrix material substrates contemplated herein are generally insoluble materials used to immobilize ligands and other molecules, and are those that used in many chemical syntheses and separations. Such matrices are fabricated preferably from biocompatible, more preferably from biodegradable materials. Such substrates, also called matrices, are used, for example, in affinity chromatography, in the immobilization of biologically active materials, and during chemical syntheses of biomolecules, including proteins, amino acids and other organic molecules and polymers. The preparation and use of matrices is well known to those of skill in this art; there are many such materials and preparations thereof known. For example, naturally-occurring matrix materials, such as agarose and cellulose, may be isolated from their respective sources, and processed according to known protocols, and synthetic materials may be prepared in accord with known protocols. Other matrices for use herein may comprise proteins, for example carrier molecules, such as albumin.

The substrate matrices are typically insoluble materials that are solid, porous, deformable, or hard, and have any required structure and geometry, including, but not limited to: beads, pellets, disks, capillaries, hollow fibers, needles, solid fibers, random shapes, thin films and membranes. Thus, the item may be fabricated from the matrix material or combined with it, such by coating all or part of the surface or impregnating particles.

Typically, when the matrix is particulate, the particles are at least about 10–2000 $\mu$M, but may be smaller or larger, depending upon the selected application. Selection of the matrices will be governed, at least in part, by their physical and chemical properties, such as solubility, functional groups, mechanical stability, surface area swelling propensity, hydrophobic or hydrophilic properties and intended use. For use herein, the matrices are preferably biocompatible, more preferably biodegradable matrices.

If necessary the support matrix material can be treated to contain an appropriate reactive moiety or in some cases the may be obtained commercially already containing the reactive moiety, and may thereby serve as the matrix support upon which molecules are linked. Materials containing reactive surface moieties such as amino silane linkages, hydroxyl linkages or carboxysilane linkages may be produced by well established surface chemistry techniques involving silanization reactions, or the like. Examples of these materials are those having surface silicon oxide moieties, covalently linked to gamma-aminopropylsilane, and other organic moieties; N-[3-(triethyoxysilyl)propyl] phthelamic acid; and bis-(2-hydroxyethyl) aminopropyltriethoxysilane. Exemplary of readily available materials containing amino group reactive functionalities, include, but are not limited to, para-aminophenyltriethyoxysilane. Also derivatized polystyrenes and other such polymers are well known and readily available to those of skill in this art [e.g., the Tentagel® Resins are available with a multitude of functional groups, and are sold by Rapp Polymere, Tubingen, Germany; see, U.S. Pat. No. 4,908,405 and U.S. Pat. No. 5,292,814; see, also Butz et al. (1994) *Peptide Res. 7*:20–23; Kleine et al. (1994) *Immunobiol. 190*:53–66].

These matrix materials include any material that can act as a support matrix for attachment of the molecules of interest. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like [see, Merrifield (1964) Biochemistry 3: 1385–1390], polyacrylamides, latex gels, polystyrene, dextran, polyacrylamides, rubber, silicon, plastics, nitrocellulose, celluloses, natural sponges. Of particular interest herein, are highly porous glasses [see, e.g., U.S. Pat. No. 4,244,721] and others prepared by mixing a borosilicate, alcohol and water.

Synthetic matrices include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers [see, e.g., Merrifield (1964) Biochemistry 3: 1385–1390; Berg et al. (1990) in *Innovation Perspect. Solid Phase Synth. Collect. Pap.*, Int. Symp., 1st, Epton, Roger (Ed), pp. 453–459; Berg et al. (1989) in *Pept., Proc. Eur. Pept. Symp.*, 20th, Jung, G. et al. (Eds), pp. 196–198; Berg et al. (1989) *J. Am. Chem. Soc. 111*:8024–8026; Kent et al.

(1979) *Isr. J. Chem.* 17:243–247; Kent et al. (1978) *J. Org. Chem.* 43:2845–2852; Mitchell et al. (1976) *Tetrahedron Lett.* 42:3795–3798; U.S. Pat. No. 4,507,230; U.S. Pat. No. 4,006,117; and U.S. Pat. No. 5,389,449]. Methods for preparation of such matrices are well-known to those of skill in this art.

Synthetic matrices include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethylacrylate, polypropylene-co-methyl acrylate, polyethylene-co-vinyl acetate, polypropylene-co-vinyl acetate, and those containing acid anhydride groups such as polyethylene-co-maleic anhydride, polypropylene-co-maleic anhydride and the like. Liposomes have also been used as solid supports for affinity purifications [Powell et al. (1989) *Biotechnol. Bioeng.* 33:173].

For example, U.S. Pat. No. 5,403,750, describes the preparation of polyurethane-based polymers. U.S. Pat. No. 4,241,537 describes a plant growth medium containing a hydrophilic polyurethane gel composition prepared from chain-extended polyols; random copolymerization is preferred with up to 50% propylene oxide units so that the prepolymer will be a liquid at room temperature. U.S. Pat. No. 3,939,123 describes lightly crosslinked polyurethane polymers of isocyanate terminated prepolymers containing poly(ethyleneoxy) glycols with up to 35% of a poly (propyleneoxy) glycol or a poly(butyleneoxy) glycol. In producing these polymers, an organic polyamine is used as a crosslinking agent. Other matrices and preparation thereof are described in U.S. Pat. Nos. 4,177,038, 4,175,183, 4,439, 585, 4,485,227, 4,569,981, 5,092,992, 5,334,640, 5,328,603.

U.S. Pat. No. 4,162,355 describes a polymer suitable for use in affinity chromatography, which is a polymer of an aminimide and a vinyl compound having at least one pendant halo-methyl group. An amine ligand, which affords sites for binding in affinity chromatography is coupled to the polymer by reaction with a portion of the pendant halo-methyl groups and the remainder of the pendant halo-methyl groups are reacted with an amine containing a pendant hydrophilic group. A method of coating a substrate with this polymer is also described. An exemplary aminimide is 1,1-dimethyl-1-(2-hydroxyoctyl)amine methacrylimide and vinyl compound is a chloromethyl styrene.

U.S. Pat. No. 4,171,412 describes specific matrices based on hydrophilic polymeric gels, preferably of a macroporous character, which carry covalently bonded D-amino acids or peptides that contain D-amino acid units. The basic support is prepared by copolymerization of hydroxyalkyl esters or hydroxyalkylamides of acrylic and methacrylic acid with crosslinking acrylate or methacrylate comonomers being modified by the reaction with diamines, aminoacids or dicarboxylic acids and the resulting carboxyterminal or aminoterminal groups are condensed with D-analogs of aminoacids or peptides. The peptide containing D-aminoacids also can be synthesized stepwise on the surface of the carrier.

U.S. Pat. No. 4,178,439 describes a cationic ion exchanger and a method for preparation thereof. U.S. Pat. No. 4,180,524 describes chemical syntheses on a silica support.

Immobilized Artificial Membranes [IAMs; see, e.g., U.S. Pat. Nos. 4,931,498 and 4,927,879] may also be used. IAMs mimic cell membrane environments and may be used to bind molecules that preferentially associate with cell membranes [see, e.g., Pidgeon et al. (1990) *Enzyme Microb. Technol.* 12:149].

These materials are also used for preparing articles of manufacture, surgical sponges soaps, and other items, and thus are amenable to linkage of molecules, either the luciferase, luciferin, mixtures of both. For example, matrix particles may be impregnated into items that will then be contacted with an activator.

Kits containing the item including the matrix material with or without the coating of the bioluminescence generating components, and compositions containing the remaining components are provided.

Immobilization and Activation

Numerous methods have been developed for the immobilization of proteins and other biomolecules onto insoluble or liquid supports [see, e.g., Mosbach (1976) *Methods in Enzymology 44;* Weetall (1975) *Immobilized Enzymes, Antigens, Antibodies, and Peptides;* and Kennedy et al. (1983) *Solid Phase Biochemistry, Analytical and Synthetic Aspects,* Scouten, ed., pp. 253–391; see, generally, *Affinity Techniques. Enzyme Purification: Part B. Methods in Enzymology,* Vol. 34, ed. W. B. Jakoby, M. Wilchek, Acad. Press, N.Y. (1974); *Immobilized Biochemicals and Affinity Chromatography, Advances in Experimental Medicine and Biology,* vol. 42, ed. R. Dunlap, Plenum Press, N.Y. (1974)].

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art [see, e.g., the PIERCE CATALOG, ImmunoTechnology Catalog & Handbook, 1992–1993, which describes the preparation of and use of such reagents and provides a commercial source for such reagents; and Wong (1993) *Chemistry of Protein Conjugation and Cross Linking,* CRC Press; see, also DeWitt et al. (1993) *Proc. Natl. Acad. Sci. U.S.A.* 90:6909; Zuckermann et al. (1992) *J. Am. Chem. Soc.* 114:10646; Kurth et al. (1994) *J. Am. Chem. Soc.* 116:2661; Ellman et al. (1994) *Proc. Natl. Acad. Sci. U.S.A.* 91:4708; Sucholeiki (1994) *Tetrahedron Lttrs.* 35:7307; and Su-Sun Wang (1976) *J. Org. Chem.* 41:3258; Padwa et al. (1971) *J. Org. Chem.* 41:3550 and Vedejs et al. (1984) *J. Org. Chem.* 49:575, which describe photosensitive linkers]

To effect immobilization, a solution of the protein or other biomolecule is contacted with a support material such as alumina, carbon, an ion-exchange resin, cellulose, glass or a ceramic. Fluorocarbon polymers have been used as supports to which biomolecules have been attached by adsorption [see, U.S. Pat. No. 3,843,443; Published International PCT Application WO/86 03840]. For purposes herein, the support material will be biocompatible (i.e., suitable for use in the body).

A large variety of methods are known for attaching biological molecules, including proteins and nucleic acids, molecules to solid supports [see. e.g., U.S. Pat. No. 5451683]. For example, U.S. Pat. No. 4,681,870 describes a method for introducing free amino or carboxyl groups onto a silica matrix. These groups may subsequently be covalently linked to other groups, such as a protein or other anti-ligand, in the presence of a carbodiimide. Alternatively, a silica matrix may be activated by treatment with a cyanogen halide under alkaline conditions. The anti-ligand is covalently attached to the surface upon addition to the activated surface. Another method involves modification of a polymer surface through the successive application of multiple layers of biotin, avidin and extenders [see, e.g., U.S. Pat. No. 4,282,287]; other methods involve photoactivation in which a polypeptide chain is attached to a solid substrate by incorporating a light-sensitive unnatural amino acid group into the polypeptide chain and exposing the product to low-energy ultraviolet light [see, e.g., U.S. Pat. No. 4,762,881]. Oligonucleotides have also been attached using a photochemically active reagents, such as a psoralen compound, and a coupling agent, which attaches the photoreagent to the substrate [see, e.g., U.S. Pat. No. 4,542,102 and U.S. Pat. No. 4,562,157]. Photoactivation of the photoreagent binds a nucleic acid molecule to the substrate to give a surface-bound probe.

Covalent binding of the protein or other biomolecule or organic molecule or biological particle to chemically activated solid matrix supports such as glass, synthetic polymers, and cross-linked polysaccharides is a more frequently used immobilization technique. The molecule or biological particle may be directly linked to the matrix support or linked via linker, such as a metal [see, e.g., U.S. Pat. No. 4,179,402; and Smith et al. (1992) *Methods: A Companion to Methods in Enz. 4*:73–78]. An example of this method is the cyanogen bromide activation of polysaccharide supports, such as agarose. The use of perfluorocarbon polymer-based supports for enzyme immobilization and affinity chromatography is described in U.S. Pat. No. 4,885,250]. In this method the biomolecule is first modified by reaction with a perfluoroalkylating agent such as perfluorooctylpropylisocyanate described in U.S. Pat. No. 4,954,444. Then, the modified protein is adsorbed onto the fluorocarbon support to effect immobilization.

The activation and use of matrices are well known and may be effected by any such known methods [see, e.g., Hermanson et al. (1992) *Immobilized Affinity Ligand Techniques,* Academic Press, Inc., San Diego]. For example, the coupling of the amino acids may be accomplished by techniques familiar to those in the art and provided, for example, in Stewart and Young, 1984, *Solid Phase Synthesis,* Second Edition, Pierce Chemical Co., Rockford.

Other suitable methods for linking molecules to solid supports are well known to those of skill in this art [see, e.g., U.S. Pat. No. 5,416,193]. These include linkers that are suitable for chemically linking molecules, such as proteins, to supports and include, but are not limited to, disulfide bonds, thioether bonds, hindered disulfide bonds, and covalent bonds between free reactive groups, such as amine and thiol groups. These bonds can be produced using heterobifunctional reagents to produce reactive thiol groups on one or both of the moieties and then reacting the thiol groups on one moiety with reactive thiol groups or amine groups to which reactive maleimido groups or thiol groups can be attached on the other. Other linkers include, acid cleavable linkers, such as bismaleimideothoxy propane, acid labile-transferrin conjugates and adipic acid diihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. (1993) *Molecular Immunol. 30*:379–386). Presently preferred linkages are direct linkages effected by adsorbing the molecule to the surface of the matrix. Other linkages are photocleavable linkages that can be activated by exposure to light [see, e.g., Goldmacher et al. (1992) *Bioconj. Chem. 3*:104–107, which linkers are herein incorporated by reference]. The photocleavable linker is selected such that the cleaving wavelength that does not damage linked moieties. Photocleavable linkers are linkers that are cleaved upon exposure to light [see, e.g., Hazum et al. (1981) in *Pept., Proc. Eur. Pept. Symp., 16th,* Brunfeldt, K (Ed), pp. 105–110, which describes the use of a nitrobenzyl group as a photocleavable protective group for cysteine; Yen et al. (1989) *Makromol. Chem 190*:69–82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem. 3*:104–107, which describes a cross-linker and reagent that undergoes photolytic degradation upon exposure to near UV light (350 nm); and Senter et al. (1985) *Photochem. Photobiol 42*:231–237, which describes nitrobenzyloxycarbonyl chloride cross linking reagents that produce photocleavable linkages]. The selected linker will depend upon the particular application and, if needed, may be empirically selected.

These methods for linking molecules to supports may be adapted for use to link the targeting agents to the targeted agents.

F. Surgical Devices and Instruments a. A Surgical Viewing Device for Visualizing Bioluminescent Neoplasia and Specialty Tissues (1) Background Monocular and binocular night vision devices have been developed to enable a viewer to observe objects at night and under low light conditions. These night vision devices may be battery powered, modular or solid-state, hand-held, such a telescope or night viewer, or mounted on a gun or helmet, such as a weapon sight or binoculars/goggles or other head gear (e.g., see U.S. Pat. Nos. 3,509,344; 4,449,783; 4,629,295; 4,642,452; 4,734,939; 4,822,994; 4,948,210; 4,953,963; 5,029,963; 5,084,780; 5,117,553; 5,146,077 5,396,069; and, 5,535,053).

Several night vision devices are commercially available that detect low intensity visible and infrared light [e.g., monocular and binocular goggles, pocketscopes and viewers; Stano Components, Carson City, Nev.; Star-Tron Technology Corp., Pittsburgh, Pa., Excalibur Enterprises; RET-RON night vision devices, Surveillance Technology Group, Mamaroneck, N.Y.; Princeton Instruments, MA]. These night vision devices may be passive, relying only on ambient light, or active, where an external light source provides illumination for enhanced viewing.

In general, active night vision devices are contain of a power source and an infrared illuminator, e.g., a laser, that projects a beam of near infrared light [U.S. Pat. No. 4,948, 210 describes an infrared zoom illuminator means]. Infrared and low intensity visible light is received from the surrounding environment through an objective camera lens that focuses and transmits images in the viewing area onto an image intensifier tube [e.g., GEN II & III image intensifiers are described in U.S. Pat. No. 5,146,077]. The GEN II & III intensifier tubes are commercially available (ITT Electro-Optical Products Division, Roanoke, Va). The GEN III intensifier tube, preferred of the existing intensifier tubes, results in greater than a 50,000-fold amplification in light intensity (with ~30–50% quantum efficiency between 600–700 nm) and a lifetime use of about 10,000 hours.

An image intensifier may contain a S-20 or S-25 photocathode, a photoemissive wafer that is extremely sensitive to low radiation levels of light in the 580–900 nm spectral range. The photocathode may be optionally coated with gallium arsenide, which increases the light amplification 4-fold (e.g., as available in the GEN III intensifier tube). The intensified image may be projected, for example, onto a phosphor screen of a photosensor, which converts the electronic emissions into visible light for viewing. The intensified images are viewed on the phosphor screen through an ocular lens assembly.

In addition, a microchannel plate (MCP) may be placed between the photocathode and the phosphor screen to enhance the brightness of the image. For example, 18 mm and 25 mm MCP second generation imager intensifiers are commercially available (Stano Components, Carson City, Nev.).

Alternatively, a charged coupled device (CCD) detector array may be used in association with the video camera/image intensifier system. In this instance, the intensified image may be transmitted through the CCD imager of a video camera which is connected to a display apparatus via a control unit [e.g., see U.S. Pat. No. 4,642,452].

(2) Surgical Vision Device

A surgical vision device useful for detecting low intensity visible light from bioluminescent neoplaisa and specialty tissue is provided. The surgical vision device is analogous to the above-described night vision devices in that the image intensifier preferably receives or detects low intensity visible light, particularly wavelengths between 500–900 nm. Preferred for the in vivo detection of neoplaisa and specialty tissue are wavelengths of visible light, preferably those wavelengths between 500– 900 nm, more preferably green, red and near infrared wavelengths. In particularly preferred embodiments, the surgical night vision device is highly sensitive to low intensity visible red light.

Any night vision device that detects low intensity visible light is contemplated for use in the methods described herein. In addition, an existing vision device may be modified for use herein, such as by replacing the infrared-sensitive CCD imager or photocathode of the image intensifier, with a corresponding component that has an exceptionally high sensitivity to low intensity visible light. The GEN III image intensifier adequately detects light in the desired wavelengths, especially red and near infrared light (e.g., light wavelengths greater than λ650 nm). The selection of the appropriate image intensifier or requisite modifications will depend on the wavelength and intensity of the light generated by the bioluminescent reaction which may be determined empirically by one of skill in the art using the teachings herein.

To minimize undesired wavelengths of light, an optical interference filter may also be employed in conjunction with these devices to allow only the desired wavelengths of light to pass through to the image intensifier or other equivalent imager. Such a filter may be included between the optical detector and the image intensifier to minimize the level of background light, i.e., wavelengths less than 500 nm or greater than 1000 nm.

The monocular and binocular night vision devices described in U.S. Pat. Nos. 5,396,069 or 5,535,053 are particularly suited for use in the methods described herein, particularly the modular apparatus described in U.S. Pat. No. 5,535,053. As described therein, a GEN III image intensifier (i.e., item 40 in FIG. 2) is contained in a tubular housing flanked on one end by an adjustable objective lens assembly and an adjustable ocular lens assembly attached to the opposite end of the housing. The intensified image produced by the GEN III intensifier tube is viewed on the phosphor screen through the adjustable ocular lens assembly. The GEN III image intensifier may be used or replaced with a modified image intensifier that has a higher sensitivity low intensity visible light.

(3) Methods of Use

The surgical vision device provides the surgeon a means for visualizing the image of a tumor or specialty tissue from the low intensity visible light produced at the target site from a selected bioluminescence generating system. For example, a targeting agent conjugated to a component of the bioluminescence generating system, preferably a luciferase, may be administered to a patient followed by the remaining components of the bioluminescence generating system. After exposure of the target area for surgical viewing, the image of the glowing tumor or specialty tissue is captured by the objective lens and focused onto the photocathode tube of a GEN III or equivalent image intensifier. In a dark, sterile room, the glowing image is readily detected against the dark background of the body cavity and the image projected on the phosphor screen is viewed through the ocular lens assembly. Metastatic tumors may also be rapidly identified by visual inspection of the exposed surrounding tissues and organs. Surgical removal of the target may occur in the absence or presence of the assistance of the surgical vision device.

In particularly preferred embodiments, the surgical vision device is used for the detection of deep tumors and metastases using a bioluminescence generating system that produces red light at the target site. Presently preferred are the bioluminescence generating systems isolated from Aristostomias, such as *A. scintillans,* Pachystomias and Malacosteus, such as *M. niger,* all of which produce red light [i.e., light of a wavelength between 650 and 750 nm, peaking at 705 nm; Widder et al. (19??) Science News 150(14):214].

In alternative embodiments, blue or green light may produced at the target site using a bioluminescence generating system, e.g., using Renilla bioluminescence generating system, and converted to red light by further including a fluorescent protein, such as a phycobiliprotein, which converts green light to red light. The concentration of the bioluminescence generating components necessary to generate red light of sufficient intensity to be detected by the surgical vision device will vary but may be determined empirically by one of skill in the art using methods described herein and those known to those of skill in the art.

b. Miniature Surgical Imaging Instruments

(1) Background

Optical images of the interior of a living body may also be generated by a surgeon using a surgical imaging instrument. Examples of instruments used for surgically viewing the internal organs of a patient include, but are not limited to, laparoscopes, endoscopes, cytoscopes, arthoscopes and thorascopes [e.g., see U.S. Pat. Nos. 5,511,564; 5,311,859; 5,313,306 and 5,331,950].

The application of these instruments requires only a minimally invasive surgical procedure. In general, the surgeon makes a small incision in the patient nearby the targeted viewing area into which the elongated tube of the instrument is inserted. The instruments are guided through the body to the viewing area by the surgeon or by remote controlled means [e.g., see U.S. Pat. No. 5,540,649 describing a device for remotely controlling surgical instruments].

Light is transmitted from a light source through the insertion tube using a fiber optic bundle to illuminate internal objects of the body cavity. The illuminated images are focused by a lens housed at the distal end of the insertion tube onto an image forming surface of a CCD imager or other equivalent imager. The optical image is then converted to an electric output signal that is displayed on a video monitor, LED monitor or phosphor screen.

In addition, a wide angled lens may be used to increase the available viewing area, and any image distortion from such lenses may be optically corrected using an omniview transformation system, which allows for multiple simultaneous images to be outputed from a single location [e.g., see U.S. Pat. No. 5,313,306].

(2) Surgical Viewing Instruments for Detecting Bioluminescent Neoplaisa and Specialty Tissue Surgical instruments for detecting bioluminescent neoplaisa and specialty tissue are provided herein. More particularly, surgical instruments containing miniaturized imagers that are specifically designed to detect bioluminescence inside the body cavity of a patient are provided herein.

Any surgical imaging device capable of detecting emissions generated from a bioluminescent generating system is contemplated for use in the methods and EXAMPLES provided herein. For example, surgical instruments that any detect emissions generated throughout the human scotopic and photopic range, e.g., ultraviolet through infrared wavelengths, are contemplated for use herein. In preferred embodiments the instruments are highly sensitive to broad spectrum visible light, and in more preferred embodiments, the instruments are highly sensitive to narrow ranges visible light, particularly blue, green or red wavelengths.

In especially preferred embodiments, surgical viewing instruments contain a modified CCD imager or other equivalent imager that is useful for the detection of bioluminescence. Particularly preferred instruments are those described in U.S. Pat. Nos. 5,313,306 (endoscope), 5,311,859 and 5,331,950 (laparoscopes). For example, U.S. Pat. No. 5,331, 950 describes a video laparoscope assembly in which a miniature camera, containing a lens assembly, focuses an image of a target onto an image forming surface of CCD video camera imager. The intensified image is converted to an output signal which is sent to a video processing unit. The reproduced image is displayed on an accompanying video monitor.

Existing CCD imagers and other equivalent image intensifiers may be used in the methods that are sensitive to low intensity visible and infrared light. These CCD imagers are commercially available and well known to those of skill in the art (e.g., Tektronics TEK Nos. 25, 27 & 32 CCD imager intensifiers; Generation II and III image intensifier tubes, ITT Electro Optics Division, Roanoke, Va.; cooled CCD arrays and image intensifiers, Princeton Instruments, Inc., Fremont, Calif.; SenSys 1400 and 1600 digital cameras, Photometrics, Ltd; Model 221, Javelin Electronics and, 18 and 25 mm MCP second generation image intensifier tubes, Stano Components, Inc, Carson City, Nev.). Any of these imager intensifiers may be used in the apparatus described herein.

The selection of the appropriate CCD imager for use in the methods herein will depend on means of visualizing the tumor and the wavelength and intensity of the light generated by the bioluminescent reaction. These parameters may be determined empirically by one of skill in the art using the teachings provided herein. For the detection of extremely low levels of light emission, the surgical instrument may optionally contain an image intensifier tube, e.g., a GEN III image intensifier tube or red-sensitive Model 221 image intensifier, and the intensified image visualized on a phosphor screen or other equivalent display means.

Using these surgical instruments, an external light source is not required for viewing the bioluminescent target because the tumor or specialty tissue targeted for surgical removal glows in the absence of excitation by an external illumination source. When necessary, a light source may be used that generates broad spectrum light or monochromatic light of narrow spectral bands. In addition, the color of the broad spectrum light may be filtered to reduce background and light scattering. Color wheel filters adaptable for use in these instruments are known [e.g., see U.S. Pat. No. 4,523, 224]. Alternatively, in order to minimize undesired wavelengths of light from reaching the CCD imager or intensifier tube, an appropriate optical interference filter may be placed between the video camera and the imager.

In a preferred embodiment, the CCD imager of the surgical instrument is highly sensitive to visible light, preferably blue or green light [$\lambda_{400-600\ nm}$]. A tumor-specific targeting agent, e.g., an antibody directed against a colon cancer specific-antigen, is coupled to a component of the Aequorin or Renilla bioluminescence generating system, preferably the photoprotein or luciferase, respectively. In the presence of the remaining components, bluish-green light is produced at the site of the tumor. The remaining components, i.e. an appropriate substrate and/or any necessary activators, may be added intravenously or using a laparoscope or trocar that allows for local administration of fluid to the target site through the insertion tube [e.g., see International Patent Application No. WO 95/32012]. A laparoscope that contains a CCD imager that is highly sensitive to low intensity visible light in these wavelengths, is used by the surgeon to detect and visualize the image of the glowing tumor. The target tissue may be removed surgically or removed using a medical ablation device [e.g., see U.S. Pat. Nos. 5,486,161 and 5,511,564 describing laparoscopic medical ablation devices].

In another preferred embodiment, the CCD imager of the surgical imaging instrument is replaced with an imager containing a CCD array that is highly sensitive to low intensity red light [e.g., $\lambda_{650-750\ nm}$]. Wavelengths of red and near infrared light of about 700–1300 nm are known to easily penetrate through the skull, soft tissue and into bone [e.g., see U.S. Pat. No. 4,281,645]. In this embodiment, a tumor-specific targeting agent is coupled to a component of a red emitting bioluminescent generating system, e.g., Aristostomias, and the remaining components of the reaction are added as described above. Red light emitted from the tumor is detected using the modified laparoscope or endoscope. The glowing image of the tumor may be visualized through surrounding and nearby tissues, even in deep tissue tumors such as breast cancer, eliminating the need to surgically view the targeted tissue.

c. Computer Tomographs (1) Background

A computer tomograph is a non-invasive, medical imaging device capable of generating prescribed sectional pictures of the interior of a living body. These sectional images, i.e., computer tomograms, are arranged in different planes from which a three dimensional computer image of the internal organs and tissues of the body may be constructed.

In general, a computer assisted tomograph, e.g., an X-ray CT scanner, is composed of a patient support, an X-ray radiator and detector array capable of being rotated 360 degrees around the patient axis and a computer processing unit for image re-construction. In preparing computer tomograms, a subject is placed horizontally on the patient support and irradiated with a narrow beam of X-rays. The X-ray radiator and detector array, fixed in space relative to one another, are rotated 360 degrees around the patient. The circumferential output signals from the detector array are relayed to a computer processing unit which reconstructs an image of the target. The reproduced image is viewed on a video monitor or other suitable display means [e.g., see U.S. Pat. Nos. 5,113,077; 5,315,628; 5,533,082].

In addition to images generated using X-rays, apparatus for optically inspecting the human body using light are also known. For example, spectrophotometric methods and apparatus for optically monitoring biological processes, such as blood metabolism, are known [e.g., see U.S. Pat. Nos. 4,281,645; 5,148,022; 5,337,745; 5,413,098; International Patent Application Publication No. WO 93/13395; Amato (1992) Science 258:892–893]. Furthermore, optical tomography using laser-emitting apparatus that pulse wavelengths of near infrared light has been employed to visualize images of phantom objects placed in tissue and also the internal organs of animals [Benaron et al. (1994) in Oxygen Transport to Tissue, Ed. Hogan et al., pp. 207–222 Plenum Press, NY].

Conventional tomographic and spectrophotometric apparatus require an external source of radiation for image detection and construction. For example, traditional computer tomography requires an irradiation source for generating X-rays. Optical tomographs require one or more lasers to generate a narrow beam of light in the near infrared region of the spectrum to minimize scattering and absorbtion of photons by tissues. Computer software containing algorithms for forward and inverse problems of image re-construction in optical tomography has been developed, such as time-of-flight absorbance [TOFA; e.g., see Benaron et al. (1993) Science 259:1463–1466; Benaron etal. (1994) in Oxyyen Transport to Tissue, Ed. Hogan et al., pp. 207–222 Plenum Press, NY] or time-resolved optical absorbtion and scattering tomography [TOAST; e.g., Arridge et al. (1991) Proc. SPIE 1431:204–215; Arridge et al (1993) Proc. SPIE 2035:218–229].

(2) Computer Apparatus for the Non-invasive Detection of Bioluminescent Neoplaisa and Specialty Tissue A computerized apparatus and non-invasive methods for optically inspecting the interior of a living body are provided herein. More particularly, a computerized optical imaging apparatus and non-invasive methods for optically imaging bioluminescent neoplasia and specialty tissues are provided herein.

It is to be appreciated that any apparatus that is capable of detecting electromagnetic radiation generated from a bioluminescent reaction and calculating an image of the bioluminescent target is contemplated for use in the methods described herein. For example, the computerized optical imaging apparatus may be analogous to a computer tomograph except that bioluminescence is used as the radiation source and an optical detector as the image detector. Image reconstruction may be performed using a computer processing unit containing software that uses algorithms and principles employed in X-ray CT scanners and optical computer tomography, such as time-of flight optical imaging, convolution integration and Fourier analysis [e.g., see Benaron et al. (1993) Science 259:1463–1466; U.S. Pat. Nos. 5,113, 077; 5,315,628; 5,533,082].

Alternatively, the apparatus may contain any optical detector known to those of skill in the art capable of detecting electromagnetic radiation through tissue or other biological medium. Visible light may be detected directly through animal tissue using a photon detector or digital camera.[e.g., see Travis (1996) Science News 150:220–221]. Thus, the instant apparatus may contain an array of digital cameras may be used to detect light emission from the bioluminescent neoplaisa or specialty tissue. In this exemplary embodiment, digital cameras may be placed at any angle or any position nearby a targeted viewing area or, alternatively, a complete scan of the entire patient may be performed. The electromagnetic radiation detected by the digital camera may be relayed to a computer processing unit and computer image of the bioluminescent neoplaisa or specialty tissue is re-constructed based from the intensity of the detected light emissions using one or more of the above-described computer algorithms.

By moving one or more digital camera, several computer images may be produced and overlayed upon one another to generate a three dimensional image of the bioluminescent neoplaisa or specialty tissue. The imaging of the bioluminescent tumors or specialty tissues may be also be performed by overlaying against images obtained using other non-invasive diagnostic imaging methods. Particularly preferred is the projection of bioluminescent neoplasms on images obtained using standard ultrasound techniques, such as sonograms [e.g., see U.S. Pat. Nos. 5,575,288; 5,619,995; 5,619,999; 5,622,172; 5,630,426].

In preferred embodiments, the optical imaging apparatus is capable of detecting low intensity visible light emissions from the interior of a patient. One or more digital camera is used to detect light output from the bioluminescent target, and the detected images are relayed to a computer processing unit that generates an image of the bioluminescent neoplaisa or specialty tissue. In especially preferred embodiments, the optical detector of the apparatus is highly sensitive to wavelengths of low intensity red and near infrared light, which wavelengths are known to undergo the least amount of scattering through tissue or other biological medium.

G. Photodynamic Therapy

1. Background

The bioluminescent targeting agent conjugates may also be used the detection and treatment of neoplasia in conjunction with photodynamic therapy techniques. These techniques involve the administration of a photosensitizing drug to a patient. The drugs or chemicals subsequently localize in neoplastic cells which are then illuminated from an external source with light of an appropriate wavelength to activate the drug or chemicals. This photoactivation results in photochemical reactions in the neoplastic tissue that ultimately cause cytotoxic injury and/or death of the targeted tissue.

A wide variety of compounds suitable for use as photosensitizing drugs are commercially available or may be prepared using methods known to those of skill in the art. For example, the compounds may be derived from natural sources (e.g., porphyrins, chlorins and purpurins) or from known chemicals originating in the dyestuffs industries (e.g., cyanine dyes). Specific examples of photosensitizing drugs include, but are not limited to, phyhalocyanines (merocyanine 540), substituted purpurines, xanthenes (Rhodamine 123 6G&B), cationic cyanine dyes, chlorine polymers, chalcogenapyrylium dyes containing selenium or tellurium atoms in the chromophore, phenothiazolium derivatives, benzophenoxoniums (Nile Blue A) and triarylmethanes (Victoria Blue BO) [e.g., see U.S. Pat. Nos. 4,861,876; 4,961,920; 5,132,101; 5,179,120; 5,189,029; 5,344,928; 5,409,900; 5,433,896; 5,446,157; 5,532,171 and International Patent Application Publication Nos. WO 95/24930 and WO 96/31451].

The photosensitizing drugs may be formulated, for example, for topical, local, parenteral or systemic intravenous administration. In addition, the specificity of the photosensitizing drug for neoplastic cells can also be increased by conjugation to a known anti-tumor targeting agent. For example, the photosensitizing drug may be conjugated to an antibody or other peptide. The method of conjugating a porphyrin dye to an anti-cancer antigen antibody is known [e.g., see European Patent Application No. EP 252683].

The exact mechanism used by the above-mentioned chemicals to destroy neoplastic cells upon exposure to an external excitatory light source is currently unknown. There are two generally proposed mechanisms by which photosensitizing drugs are chemically altered upon illumination. The first mechanism typically involves hydrogen atom abstraction from the drugs, thereby producing free radicals that react with organic products or oxygen, which results in biochemical destruction of the neoplastic cells. The other reaction mechanism normally involves energy transfer from the electronically excited drugs to oxygen producing a singlet oxygen. The singlet oxygen reacts with a variety of substrates to produce oxygenated products in combination with superoxide ions that results in disruption of the target cell wall or mitochondria and destruction of the neoplastic cell.

External light sources, such as white light sources and lasers, are typically used as the radiation source. The time and duration and repetition of irradiation varies depending on the particular photosensitizing compound selected, the means of administration and the neoplasia to be treated. For example, irradiation takes place not less than one hour nor more than four days after parenteral administration of a porphyrin derivative; whereas radiation may commence as soon as 10 minutes after topical application of the same or similar compound [e.g., see U.S. Pat. No. 5,409,900]. Photodynamic therapy is usually initiated about 3 to 48 hours after administration of the photosensitizing drug and may be performed using invasive as well as non-invasive surgical procedures. Apparatus for irradiating living cells are well known to those of skill in the art [e.g., see International Patent Application Publication No. WO 96/24406].

Not all neoplasia are suitable candidates for photodynamic therapy. Nevertheless, photodynamic therapy has been used to treat bladder, bronchial, bone marrow and skin tumors as well as severe psoriasis [e.g., see U.S. Pat. No. 5,179,120]. Specific examples of skin malignancies include basal and squamous cell cancers, malignant melanoma, Kaposi's sarcoma, mycosis, fungoides, metastatic epidermoid, and recurrent breast cancer. Head and neck cancers, such as nasopharyngeal, tongue and other oropharyngeal tumors may also be treated. Other examples of neoplastic tissue that may be treated are endobronchial cancer (such as adenocarcinoma or small cell carcinoma), esophageal cancers, gynecologic tumors (such as cervical carcinoma, vaginal cancer and vulvar malignancies) as well as brain tumors (such as glioblastoma and astrocytoma) and metastatic malignancies [e.g., see U.S. Pat. No. 5,446,157].

2. Methods of Using Photodynamic Therapy in Conjunction with Bioluminescent Targeting Agents The photosensitizing drugs used in photodynamic therapy may also be used in methods with the bioluminescent targeting agent conjugates, as described herein, in the detection and treatment of neoplasia and specialty tissue. These methods differ from traditional photodynamic therapy in that light required to activate the photosensitizing drug is generated in situ by a bioluminescent reaction. Thus, irradiation of the drug occurs directly at the surface of the neoplastic cell by light emitted by the targeting agent-luciferase conjugate, which has been localized on the surface of the targeted cell through the specific interaction of the targeting agent and the target Therefore, the present method may be used with a wide variety of compounds and photodynamic therapies, and provides non-invasive surgical procedures for treating a diverse array of neoplasia.

For practice in the methods, an effective amount of a photosensitizing drug may be administered to a patient successively or simultaneously with an anti-tumor antigen antibody conjugated to one or more component of a bioluminescence generating system, preferably a luciferase. After allowing an amount of time sufficient for binding of the antibody conjugate to the neoplastic tissue and subsequent sequestration of the photosensitizing drug by the neoplastic tissue, e.g., 10 min to 24 hr, the remaining components of the bioluminescent reaction, e.g., luciferin and any necessary activators, are administered to initiate the bioluminescent reaction. Light production activates the photosensitizing drug resulting the death of the targeted neoplastic cell.

The bioluminescence generating system used to activate the photosensitizing drug will vary depending on the biochemical properties of the drug [e.g., the absorbtion maxima] and the type of neoplaisa to be detected or treated. The selection of the drug and bioluminescence system may be determined empirically based on the teachings herein. In addition, the targeting agent may also include the use of a fluorophore or fluorescent protein, e.g., GFP, to alter the wavelength of the emitted light to provide a wider range of wavelengths for treatment.

This method is particularly advantageous for detecting and treating metastatic tumors using photodynamic methodologies. For example, metastases may be located quite distant from the primary site of irradiation used in traditional photodynamic techniques and, thus, metastatic regions may not receive a sufficient dose of irradiation for photoactivation of the drug. In the instant method, light may be continuously produced at any location in which the targeting agent binds. Therefore, sufficient quantities of light may be generated throughout the body to eliminate those neoplastic cells that have metastasized from the location of the primary tumor.

Presently preferred compounds for use in the methods herein are those that have absorption maxima between 400 and 900 nm wavelengths and particularly preferred bioluminescence generating systems are those that emit wavelengths of light greater than 500 nm, Aristostomias and Malecostus. In addition, methods using photodynamic therapy with one or more fluorescent protein and the bioluminescent generating systems of Renilla and the photoprotein aequorin are also preferred.

H. Practice of the Methods

Among the embodiments herein, are those in which a bioluminescence generating component, preferably a luciferase, is conjugated to an antibody directed against a human tumor antigen. A patient is administered a pre-operative dose of the antibody-luciferase conjugate, which binds to the tumor antigen. During the surgical procedure, the final components, i.e., a luciferin and any activators, are applied topically to the suspected area of the neoplasia, causing the tumor-antigen expressing cells to be illuminated. The illuminated area may be detected visually or using one of the above-described surgical instruments.

In the case of melanoma, for example, the antibody-luciferase conjugate may be applied topically in a lotion, ointment, cream or other such formulation, and the unbound and non-specifically bound antibody conjugate removed by washing or administered i.c.v or i.p. The remaining bioluminescence-generating components are topically applied to visualize the location and margins of the neoplastic melanoma cells for surgical removal.

Use of Microcarriers

The light intensity of the bioluminescent reaction may be amplified by coupling more than a single luciferase molecule to a microcarrier (e.g., microparticles or microbeads). The luciferase-coupled microcarrier may be covalently or non-covalently linked to a target agent and injected into an animal or human patient. Upon binding to the target, the remaining components of the bioluminescent reaction are added and the light production from the tumor or specialty tissue will be greatly enhanced compared to a targeting agent-luciferase protein conjugate (e.g., an aequorin-Mab conjugate, see U.S. Pat. No. 5,486,455).

Using the coupling methods described herein, a set of microcarriers may be designed containing one or more type of luciferase for the rapid production of a single targeting agent linked to one or more luciferase each having different biochemical properties (i.e., emit light of a different wavelength). In addition, more than one of the bioluminescence generating components may be coupled to the microcarrier. For example, aequorin or Renilla luciferase may be coupled, concurrently or successively, with a GFP, which absorbs light of one wavelength ($\lambda_{max}$=480 nm) and emits light of a different wavelength ($\lambda_{max}$=509 nm). Thus, Renilla luciferase bound to a microcarrier would emit blue light whereas a microcarrier containing Renilla luciferase and GFP would emit green light. Alternatively, the coupling a component of the Aristostomias, Pachystomias or Malacosteus bioluminescence generating system to a microcariier would result in the production of red light.

The targeting agent may be conjugated to one or more components of the bioluminescence generating system contained on the microcarrier through a biotin-streptavidin complex. The interaction between avidin/streptavidin and biotin is well documented and has been exploited as a research tool across several scientific disciplines (e.g., see Bayer and Wichek (1980) *The Use of Avidin/Biotin Complex as a Tool in Molecular Biology. Meth. Biochem. Anal.* 26, 1–45).

The coupling of proteins and small molecules to biotin is well known and bioluminescence generating components are amendable to biotinylation. For example, biotinylated aequorin has been reported (Stultz et al. (1992) *Use of Recombinant Biotinylated Apoaequorin from Escherichia coli. Biochemistry* 31, 1433–1442; Smith et al. (1991) *A Microplate Assay for Analysis of Solution Phase Glycosyltransferase Reactions: Determination of Kinetics Constants. Anal. Biochem.* 199, 286–292). In addition, reagents are commercially available for coupling biotin to primary amines, sulfhydryl groups, carboxyl groups and the side chains of the amino acids tyrosine and histidine (see Pierce Catalog, pp. T123–T154, 1994). Kits designed for biotinylating compounds are also commercially available (e.g., Boehringer Mannheim Corp., Indianapolis, Ind.).

In addition, streptavidin matricies useful as microcarriers may be purchased or synthesized starting with the matricies described in Section 3(C)(3)(a) herein. Thus, the streptavidin-biotin coupling method is amendable to any targeting agent that may be coupled to biotin and any streptavidin matrix suitable as a microcarrier that may be coupled to at least one or more luciferase molecule.

The following examples are included for illustrative purposes only and are not intended to limit the scope of the invention.

EXAMPLE 1

I. TOXICOLOGY

1. Solubility of Coelenterazine

Coelenterazine is not terribly soluble in non-irritant vehicles. Coelenterazine is soluble to at least to a concentration of 200 micrograms/mL in a solution of 2% (w/v) PEG 400 containing about 0.8% (w/v) NaCl. Although this solution is slightly hypertonic, it is not an irritant for vehicle purposes.

2. Toxicology of Coelenterazine

A. Topical Administration

To examine the toxicology of the above-described coelenterazine solution, the solution was administered in the eyes of anesthetized rabbits following standard procedures and conjunctival irritation was measured. Animals were sedated with diazepam (about 2 mg/kg) and 100 $\mu$L of the coelenterazine in the PEG solution was instilled in one eye and to the other eye only the PEG vehicle was instilled. Animals were observed for a 30-min period and then the animals were carefully examined for any conjunctival irritation as well as any corneal ulceration. The examination was performed using a slit-lamp to visualize the eye well. Only minimal conjunctival irritation from the vehicle was observed in either eye (n=3). Thus, the direct administration to the eye of about 20 $\mu$g of coelenterazine in this solution produced no irritation, ulceration, or other signs of toxicity in this topical assay.

B. Intravenous Administration

In a second experiment, mice are administered coelenterazine (n=6) at a concentration 1 mg/kg, i.p. or vehicle (n=6) for a seven-day period. Mice are examined over the course of the study for any gross signs of toxicity as evidenced in their behavior.

At the end of the one-week period, blood which is collected by cardiac puncture immediately prior to sacrifice. Animals are sacrificed and ten different tissue samples are removed post mortem from each animal. Isolated tissues are fixed, stained, blocked and sectioned. The pathology of the tissue samples will be analyzed and the toxicology data are compiled. Daily administration of coelenterazine for three days resulted in no gross behavior changes in the test animals.

C. Stability of Coelenterazine

The stability of coelenterazine may be determined by analyzing biological samples for the presence of coelentrazine and metabolic products derived therefrom. In this experiment, blood will be collected and serum prepared, and this serum can be assayed for coelenterazine and its metabolites. Little interference was observed from the serum (mouse) at the emission wavelength requisite for coelenterazine.

Alternatively, a lobe of liver may be resected from each animal and separately pooled, fixed, homogenized in cold acid acetone, and assayed for coelenterazine and its metabolites by standard biochemical analyses.

D. Coelenterazine Assays

The concentration of coelenterazine may be determined using its inherent fluorescence properties. For example, coelenterazine may be measured in an alcohol solution by measuring the fluorescence at a specified wavelength. To date, the detectable limit is less than 10 ng/mL. Given the dosages contemplated herein, this level of sensitivity should be sufficient for accurate measurement.

The concentration of coelenterazine may also be determined by use of HPLC in combination with fluorescence detection. In addition to an HPLC-based detection system, coelenterazine and its metabolites may be identified by Gas Chromatography (GC) or by Mass Spectrophotometry analysis. Final confirmation of the identity of coelenterazine and its metabolites may be performed by nuclear magnetic resonance (NMR). Method of Preparing Photoprotein Conjugates A method for the preparation of photoprotein conjugates that retain bioluminescent activity has been described (see U.S. Pat. No. 5,486,455). In general, additional sulfhydryl groups are introduced into the photoprotein by treatment of the photoprotein with Trauts Reagent (2-iminothiolane) to generate a sulfhydryl-activated photoprotein. The sulfhydryl-activated photoprotein is conjugated to a sulfhydryl-reactive binding reagent (e.g., a macromolecule that has been chemically modified with a heterobifunctional linker that is capable of sulfhydryl crosslinking, such as maleimido- or sulfo-SMCC, sulfosuccinimidyl-4-(N-maleimidomethyl) cyclohexane-1-carboxylate). The conjugated photoprotein may be used in crude form or may be further purified by methods known to those of skill in the art, such as ion exchange or affinity chromatography.

EXAMPLE 2

Rodent Model

A monoclonal antibody directed against a human tumor antigen (e.g., Lewis antigen or carcinoembryonic antigen [CEA]) or a humanized derivative thereof is conjugated to a photoprotein, preferably aequorin, or to the vargula luciferase, via the sulfhydryl-binding method (see U.S. Pat. No. 5,486,455) and the conjugate is purified. Approximately, 10–100 micrograms of the antibody-photoprotein conjugate is injected i.v. in the tail vein of a transgenic mouse which expresses a human tumor antigen. The injection should be tolerated well by the animal.

After sufficient time is allowed for antibody binding (2–48 hours), approximately 1 $\mu$g of the coelenterazine or 10 $\mu$L of crude lysate containing the remaining bioluminescence generating components is injected i.p. directly in the region of the proposed neoplasm. Alternatively, 10 $\mu$L of the lysate or 1 $\mu$g of coelenterazine is i.p. injected and time allowed for the coelenterazine to circulate to the target region (25 minutes to 2 days).

The mouse is then anesthetized and the region containing the neoplasm is exposed in a dark room. Regions that emit light as determined by a photometer or by the human eye are targeted for surgical removal. Alternatively, the region of interest may be visualized by the insertion of a laparoscope near the site of the neoplasm and subsequent placement of the imaging camera in a position to observe light.

EXAMPLE 3

Recombinant Production *Renilla reniformis* Luciferase

The phagemid pTZ18R (Pharmacia) is a multi-purpose DNA vector designed for in vitro transcriptions and useful for expression of recombinant proteins in bacterial hosts. The vector contains the bia gene, which allows for the selection of transformants by resistance to ampicillin, and a polylinker site adjacent to the lacZ' gene. The heterologous gene of interest is inserted in the polylinker and transcribed from the lac promoter by induction, for example, with isopropyl-$\beta$-D-thiogalactopyranoside (IPTG).

The DNA encoding the *Renilla reniformis* luciferase has been cloned (e.g., see U.S. Pat. Nos. 5,292,658 and 5,418,155). The plasmid pTZRLuc-1 encodes the Renilla luciferase on a 2.2 Kbp EcoRI to Sstl DNA fragment inserted in EcoRI and Sstl sites of pTZ18R (plasmid construction is described U.S. Pat. Nos. 5,292,658 and 5,418,155; see also Lorenz et al. (1991) *Isolation and Expression of a cDNA encoding Renilla reniformis Luciferase,* Proc. Natl. Acad. Sci. U.S.A. 88, 4438–4442). The initiation of transcription of the Renilla luciferase cDNA is under the control of the lacZ' promoter. *E. coli* strains harboring plasmid pTZRLuc-1 express Renilla luciferase that is functional in bioluminescence assays and retains the properties of the native enzyme (see e.g., U.S. Pat. Nos. 5,292,658 and 5,418,155).

A derivative of pTZRLuc-1, pTZRLuc-3.6, produces approximately 7-fold higher levels of recombinant Renilla luciferase than pTZRLuc-1 when transformed into the same *E. coli* host. Competent *E. coli* strain XL-1 was transformed using purified pTZRLuc-3.6 according to the instructions provided by the manufacturer (XL-1 Supercompetent cells and protocol; Stratagene, Inc., La Jolla, Calif.). Transfectants were selected by plating on Luria Broth (LB) plates supplemented with 100 $\mu$/ml ampicillin.

Single ampicillin resistant colonies were grown in LB medium supplemented with 100 $\mu$g/ml ampicillin at ambient temperature using continuous shaking until cell growth reached mid-log phase (i.e., cell culture reaches an $O.D._{600nm}$=0.6–8 units). Transcription from the lac promoter was induced by addition of 1 mM IPTG and cell culture was shaken at ambient temperature for an additional 8 hours.

Cells were harvested by centrifugation at 10,000×g and frozen at −20° C. The cell pellet was thawed and resuspended at a 1:5 ratio (w/w) in a solution of 10 mM EDTA, pH 8.0, containing 4 mg/ml lysozyme (Sigma Chemical Corp.). The cells were placed in a 25° C. water bath for 30 minutes and then transferred to ice for 1 hour. The cells were lysed by sonication at 0° C. using a 1 minute pulse from an Ultrasonics, Inc. cell disrupter.

The lysed cellular debris was removed by centrifugation at 30,000×g for 3 hours and the supernatant was decanted and retained. The pellet was resuspended at a 1:5 ratio in the above-described solutions, and the subsequent incubations, lysis and centrifugation steps were repeated. The two supernatants were combined and stored at −70° C.

The resulting "clarified lysate" was employed as a source of recombinant luciferase. Alternatively, the lysate may be subjected to additional purification steps (e.g., ion exchange chromatography or immunoaffinity chromatography) to further enrich the lysate or provide a homogeneous source of the purified enzyme (see e.g., U.S. Pat. Nos. 5,292,658 and 5,418,155).

EXAMPLE 4

Detction of Cancer Cells

The luciferase-based bioluminescent detection method has broad application in the visualization and precise localization of cancer cells. In such applications, the luciferase or luciferin molecule may be conjugated to a targeting agent, such as an anti-tumor antigen antibody, which specifically recognizes certain cancer cells that express the antigen. Alternatively, the luciferase is coupled to a microcarrier and the targeting agent is conjugated to the luciferase and/or the microcarrier. The conjugate is introduced into a subject, for example, through intravenous, intraperitoneal or subcutaneous injection or through topical application or direct application during surgery using a laparoscope or trocar. Through formation of an antibody-antigen complex, the luciferase or luciferin is linked to the target cancer cells and available for interaction with luciferin substrate (if the conjugate contains luciferase) or luciferase enzyme (if the conjugate contains luciferin). Thus, the substrate or enzyme is then introduced into the subject, eg., through injection or application, and allowed to react with the partner molecule contained in the antibody conjugate to yield the readily detectable light emission only the precise areas where the conjugate is stably present as an antibody-antigen complex.

The sensitivity and biocompatibility of this bioluminescence detection system make it possible to discover cancer in its early stages, e.g, small numbers of cancer cells, in contrast to other less sensitive methods which are able to detect cancer cells only after the neoplasm has developed to a more advanced and potentially life-threatening stage. In addition, diagnostic methods disclosed herein may be utilized in the absence of invasive surgical procedures. For example, surgical viewing devices, computer tomograms or miniature surgical viewing instruments, see above, that has been modified to detect low intensity levels of visible red and near infrared light emitted through the tissues of the patient may also be used to assist the surgeon.

The bioluminescence detection system is particularly applicable in surgical procedures to remove cancerous lesions. The targeting of luciferase and/or luciferin to, e.g., a tumor, results in the precise delineation of the boundaries of the lesion and thereby facilitates a more exact excision and complete eradication of the cancer without removal of surrounding healthy tissue. This is of critical importance in the excision of cancerous lesions in complex, vital tissues, such as nervous tissue. The sensitivity of the bioluminescence generating system also makes it well-suited for post-surgery evaluations and identification of metastases in which the ability to detect small numbers of any remaining cancer cells enables a more accurate assessment of the effectiveness of the procedure in eradicating the cancer.

The bioluminescence generating system finds further use in monitoring the progression and spread of cancer. Such information is invaluable in assessing the effectiveness of therapies, such as chemotherapy and radiation therapy, as well as the efficacy of drug-based therapies in treating cancer patients.

Detection of Cervical Cancer

A luciferase-based bioluminescence detection system can be used in the detection of cervical cancer. For example, luciferin or luciferase may be conjugated, directly or through a linker or microcarrier, to antibodies specific for cervical cancer cell antigens (e.g., see Table 3). The conjugate is then directly applied in an appropriate formulation to the cervical tissue which is then rinsed to eliminate any unbound conjugate. The remaining components of the bioluminescent reaction, i.e., luciferin if the conjugate contains luciferase or luciferase if the conjugate contains luciferin, is then applied to the cervical tissue, along with any necessary activators, and allowed to interact with any bound conjugate. Light emission is then monitored. The light emitted may be of any visible wavelength detectable by a human eye. If cancer cells presenting the recognized antigen are present in the tissue, those cells will glow and thereby be visualized. The bioluminescence serves to provide a more precise localization of the cancer which guides a surgeon in removal of the cancerous lesion.

Detection of Carcinoembryonic Antigen (CEA)

A luciferase-based bioluminescence detection system can also be used in the detection of neoplastic cells presenting CEA, such as, e.g., cancerous cells present in colorectal cancers (e.g., see Table 3). In this application, the luciferase or luciferin is conjugated, directly or indirectly, to an antibody specific for CEA, and detection is accomplished as described above for the detection of cervical cancer. The migration of CEA-bearing cancer cells, for instance into the wall of the colon and further into the lymphatics, may also be monitored with this detection system. The modified laparoscope that detects low intensity visible light may be further employed to enhance the detection and visualization of the CEA-bearing cancer cells.

Detection of Urinary Bladder Cancer

For detection of urinary bladder cancers, the luciferase or luciferin is conjugated to a targeting agent, e.g., an antibody that recognize antigens presented on bladder cancer cells, that serve to link the conjugate to the cancerous lesions. The conjugate is introduced into the bladder, for example through a catheter, and the lesions are visualized and delineated upon subsequent introduction of the remaining components of the bioluminescent reaction into the bladder. This embodiment is particularly useful for urinary cancers of the bladder, which are currently removed during surgery by transurethral burning of the tumor located in the bladder wall using an electro-cautery. This technique would minimize cauterization of healthy bladder tissue, identify potential areas of metastasis and ensure complete surgical removal of the target.

In another embodiment, the location and margins of neoplastic bladder tissue may be defined with greater particularity by detecting the presence of the tumor with targeting agent coupled to the luciferase-bound microparticle. After administration of the target agent conjugate, the bioluminescent reaction is initiated (e.g., by addition of a luciferin and/or any activators). A secondary, GFP-bound microparticle is covalently linked to a targeting agent which is directed against nearby surrounding tissue or which preferentially targets identical, non-tumorigenic tissue. The GFP conjugate is administered to the patient. Thus, for example, the neoplastic tissue would glow emitting a blue light, e.g., using aequorin or Renilla luciferase-targeting agent conjugate whereas the GFP-bound surrounding tissue would absorb the blue light and emit green light thereby providing additional contrast to clearly define the margins of the tissue to be surgically removed.

Detection of the Spread of Migratory Cancer Cells

The infiltration of the lymphatic system by migratory cancer cells, such as from cutaneous melanomas, deep breast tumors and hepatic metastases originating in colon cancer, may be readily detected using the bioluminescence detection system. The luciferase or luciferin conjugated to a targeting agent, such as an antibody that recognizes a cancer cell antigen, complexes specifically with the cells, no matter where they are in the migratory process. The remaining bioluminescence generating components are then allowed to circulate throughout the body to interact only with the cells to which conjugate is bound. In instances in which the cancer cells have invaded the epithelial tissues at or near the surface of the skin, the conjugate and/or partner molecule may be topically applied and the resulting light emission readily detected by the human eye without invasive procedures. Additionally, a photomultiplier or surgical viewing devices may also be used to amplify the light output through the skin. In this manner, it may be possible to trace lymphatic migration of tumor cells before surgery is attempted.

Detection of Breast Cancer

The benefits of early detection of breast cancer, e.g., increased survivability rate and greater options for treatment, are numerous and well documented. The bioluminescence detection system provides a sensitive method to facilitate early diagnosis of breast cancers. For example, in such applications, the luciferase or luciferin may be conjugated to anti-estrogen or anti-progesterone receptor antibodies which target molecules that are greatly increased in number in breast cancer tissue as opposed to normal breast tissue. Thus, in this essentially quantitative assay system, the diagnosis depends on the level of luminescence detected, for example, in biopsied breast tissue. The level of luminescence may be quantified using a photometer, photomultipliers or other suitable means.

Alternatively, the targeting agent may be coupled directly or indirectly to the luciferase isolated from Aristostomias, Malacosteus or Pachystomias, which emit red light [e.g., see Widder et al. (1984) *Science* 225:512–514]. Particularly preferred are bioluminescence components isolated from the species *Aristostomias scintillans* and *Malacosteus niger*. In this application, the luciferase-containing targeting agent is administered to the patient followed by the remaining components of the bioluminescence generating system (e.g., a luciferin and/or activators). Light emissions in this wavelength are detected directly through the tissue without an invasive surgical procedure using a photomultiplier, computer tomograph or using surgical vision device that is highly sensitive to red light. Alternatively, a surgical viewing instrument may be used in which the optical detector means contains a CCD imager or an image intensifier that is particularly sensitive to red light emissions.

Since modifications will be apparent to those of skill in this art, it is intended that this invention be limited only by the scope of the appended claims.

Summary of Sequences of Representative Luciferases and the Reductase set forth in the Sequence Listing 1. SEQ ID NO. 1 *Renilla reinformis* Luciferase [U.S. Pat. No. 5,418,155]
2. SEQ ID NO. 2 *Cypridina hilgendorfii* luciferase [EP 0 387 355]
3. SEQ ID NO. 3 Modified *Luciola cruciata* Luciferase [firefly; U.S. Pat. No. 4,968,613]
4. SEQ ID NO. 4 Vargula (Cypridina) luciferase [Thompson et al. (1989) *Proc. Natl. Acad. Sci. U.S.A.* 86:6567–6571 and from JP 3-30678 Osaka
5. SEQ ID NO. 5 Apoaequorin-encoding gene [U.S. Pat. No. 5,093,240, pAQ440]
6. SEQ ID NO. 6 Recombinant Aequorin AEQ1 [Prasher et al. (1987) "Sequence Comparisons of cDNAs Encoding for Aequorin Isotypes," *Biochemistry* 26:1326–1332]
7. SEQ ID NO. 7 Recombinant Aequorin AEQ2 [Prasher et al. (1987)]
8. SEQ ID NO. 8 Recombinant Aequorin AEQ3 [Prasher et al. (1987)]
9. SEQ ID NO. 9 Aequorin photoprotein [Charbonneau et al. (1985) "Amino Acid Sequence of the Calcium-Dependent Photoprotein Aequorin," *Biochemistry* 24:6762–6771]
10. SEQ ID NO. 10 Aequorin mutant with increased bioluminescence activity [U.S. Pat. No. 5,360,728; Asp 124 changed to Ser]
11. SEQ ID NO. 11 Aequorin mutant with increased bioluminescence activity [U.S. Pat. No. 5,360,728; Glu 135 changed to Ser]
12. SEQ ID NO. 12 Aequorin mutant with increased bioluminescence activity [U.S. Pat. No. 5,360,728 Gly 129 changed to Ala]
13. SEQ ID NO. 13 Recombinant apoaequorin [sold by Sealite, Sciences, Bogart, Ga. as AQUALITE®, when reconstituted to form aequorin]
14. SEQ ID NO. 14 Vibrio fisheri Flavin reductase [U.S. Pat. No. 5,484,723]

What is claimed is:

1. A diagnostic system containing a bioluminescence generating system, comprising:
   (a) a first composition comprising, in a pharmaceutically acceptable vehicle, a conjugate that comprises a targeted agent that is a luciferase or a luciferin and a targeting agent, wherein:
      a bioluminescence generating system comprises a luciferase as one component and a luciferin as another component;
      the conjugate binds to a cell surface receptor;
      the targeting agent specifically binds to a cell surface protein; and
   (b) a second composition, comprising, in a pharmaceutically acceptable vehicle: a luciferin or a luciferase, wherein the composition comprises a luciferin if the targeted agent in the first composition is a luciferase, and a luciferase if the targeted agent in the first composition is a luciferin; and
   (c) a compound that is a spectral shifter that shifts the spectrum of light generated by the bioluminescence generating system.

2. The diagnostic system of claim 1, wherein the conjugate comprises the following components: (targeting agent)$_n$, (L)$_q$ and (targeted agent)$_m$, wherein:
   L is a linker;
   the targeting agent is a protein or peptide that specifically binds to a cell surface protein;
   at least one targeting agent is linked at any residue polypeptide via (L)$_q$ to at least one targeted agent;
   m and n, which are selected independently, are at least 1;
   q is 0 or more as long as the resulting conjugate binds to a cell surface protein on the targeted cells.

3. The diagnostic system of claim 2, wherein m and n, which are selected independently, are 1–6.

4. The diagnostic system of claim 2, wherein q is 1, n is 1 and m is 1.

5. The diagnostic system of claim 2, wherein L is selected from the group consisting of protease substrates, linkers that increase the flexibility of the conjugate, linkers that increase the solubility of the conjugate, linkers that increase the serum stability of the conjugate, photocleavable linkers and acid cleavable linkers.

6. The diagnostic system of claim 2, wherein the targeting agent is a monoclonal antibody or a growth factor.

7. The system of claim 6, wherein the antibody is selected from the group consisting of FO23C5, A10, MN14 F(ab)2, MAb J28, MAb PA8-15, MAb C 50, MAb 19-9, MAb C 242, MAb AR-3, MAb DU-PAN-2, MAb Ypan-1, MAb Span-1, MAb BW494, MAb MUSE 11, MAb 17-1A, OC125, DF3, GA733MoAb, YH206MoAb and A78-G/A7.

8. The method of claim 6, wherein the antibody is humanized.

9. The diagnostic system of claim 2, wherein the targeting agent is a tumor specific antibody.

10. The diagnostic system of claim 1, wherein the conjugate is a chimeric protein produced by fusing a luciferase to a targeting agent.

11. The diagnostic system of claim 1, wherein the conjugate is a non-covalent complex containing a targeting agent and a luciferin or luciferase.

12. The system of claim 1, wherein the spectral shifter is selected from the group consisting of fluorochrome, green fluorescent proteins, red fluorescent proteins, and luciferins altered chemically or enzymatically to cause shifts in frequency of emission.

13. The system of claim 1, wherein the bioluminescence generating system is selected from the group consisting of those isolated from the ctenophores, coelenterases, mollusca, fish, ostracods, insects, bacteria, a crustacea, annelids, and earthworms.

14. The system of claim 13, wherein the bioluminescence generating system is selected from those isolated from: fireflies, Mnemiopsis, *Beroe ovata,* Aequorea, Obelia, Pelagia, Renilla, Pholas Aristostomias, Pachystomias, Poricthys, Cypridina, Aristostomias, Pachystomias, Malacosteus, Gonadostomias, Gaussia, Watensia, Halisturia, Vampire squid, Glyphus, Mycotophids, Vinciguerria, Howella, Florenciella, Chaudiodus, Melanocostus, Sea Pens, Chiroteuthis, Eucleoteuthis, Onychoteuthis, Watasenia, cuttlefish, Sepiolina, Oplophorus, Acanthophyra, Sergestes, Gnathophausia, Argyropelecus, Yarella, Diaphus, Gonadostomias, Ptilosarcus and Neoscopelus.

15. The diagnostic system of claim 1, wherein the compositions are formulated for topical, local or systemic administration.

16. The diagnostic system of claim 15, wherein the first composition is formulated for systemic administration.

17. A kit comprising the diagnostic system of claim 1:
   wherein each of the compositions are contained within packaging that prevents mixing of the contents of each composition.

18. The kit of claim 17, wherein the conjugate comprises the following components: (targeting agent)$_n$, (L)$_q$ and (targeted agent)$_m$, wherein:
   L is a linker;
   the targeting agent is a protein or peptide that specifically binds to a cell surface protein;
   at least one targeting agent is linked at any residue polypeptide via (L)$_q$ to at least one targeted agent;
   m and n, which are selected independently, are at least 1;
   q is 0 or more as long as the resulting conjugate binds to a cell surface protein on the targeted cells.

19. The kit of claim 17, wherein the compositions are formulated in pharmaceutically acceptable vehicles for topical, local or systemic administration.

20. The kit of claim 17, wherein the targeting agent is a tumor specific antibody.

21. The kit of claim 20, wherein the antibody is selected from the group consisting of FO23C5, A10, MN14 F(ab)2, MAb J28, MAb PA8-15, MAb C 50, MAb 19-9, MAb C 242, MAb AR-3, MAb DU-PAN-2, MAb Ypan-1, MAb Span-1, MAb BW494, MAb MUSE 11, MAb 17-1A, OC125, DF3, GA733MoAb, YH206MoAb and A78-G/A7.

22. The kit of claim 20, wherein the antibody is humanized.

23. The kit of claim 17, wherein the conjugate is a chimeric protein produced by fusing a luciferase to a targeting agent.

24. The kit 17, wherein the conjugate is a non-covalent complex containing a targeting agent and a luciferin or luciferase.

25. The kit of claim 17, wherein the spectral shifter is selected from the group consisting of fluorochrome, green fluorescent proteins, red fluorescent proteins, and luciferins altered chemically or enzymatically to cause shifts in the frequency of emission.

26. The system of claim 17, wherein the compound that is a spectral shifter shifts the spectrum of the generated light towards the red end of the spectrum.

27. The system of claim 1, wherein the compound that is a spectral shifter shifts the spectrum of the generated light towards the red end of the spectrum.

28. A kit, comprising:
(a) a first composition comprising a conjugate that comprises a luciferase or a luciferin and a targeting agent, wherein:
the conjugate binds to a cell surface receptor and the targeting agent specifically binds to a cell surface protein; and
(b) a second composition, comprising in a pharmaceutically acceptable vehicle a luciferin or a luciferase; and
(c) a third composition that contains a spectral shifter.

29. A method for in vivo labeling of selected tissues, comprising:
contacting the tissue with a conjugate comprising a first component of a bioluminescence generating system, wherein the first component is a luciferin or luciferase; and
then contacting the tissue with the remaining components of the system, whereby light is generated, wherein:
contacting is effected in vivo; and
the luciferase is a red emitting luciferase or the bioluminescence generating system further comprises a compound that shifts light generated by the bioluminescence generating system to the red, whereby the generated light is visible through the skin.

30. The method of claim 29, wherein the selected tissue is neoplastic tissue or specialty tissue.

31. The method of claim 29, wherein:
the conjugate further comprises a targeting agent, and
the targeting agent is a tumor specific monoclonal antibody.

32. The method of claim 31, wherein the antibody is selected from the group consisting of FO23C5, A10, MN14 F(ab)2, MAb J28, MAb PA8-15, MAb C 50, MAb 19-9, MAb C 242, MAb AR-3, MAb DU-PAN-2, MAb Ypan-1, MAb Span-1, MAb BW494, MAb MUSE 11, MAb 17-1A, OC125, DF3, GA733MoAb, YH206MoAb and A78-G/A7.

33. The method of claim 31, wherein the antibody is humanized.

34. The method of claim 29, wherein the bioluminescence generating system is selected from the group consisting of those isolated from the ctenophores, coelenterases, mollusca, fish, ostracods, insects, bacteria, a crustacea, annelids, and earthworms.

35. The method of claim 34, wherein the bioluminescence generating system is selected from those isolated from: fireflies, Mnemiopsis, *Beroe ovata,* Aequorea, Obelia, Pelagia, Renilla, Pholas Aristostomias, Pachystomias, Poricthys, Cypridina, Aristostomias, such Pachystomias, Malacosteus, Gonadostomias, Gaussia, Watensia, Halisturia, Vampire squid, Glyphus, Mycotophids, Vinciguerria, Howella, Florenciella, Chaudiodus, Melanocostus, Sea Pens, Chiroteuthis, Eucleoteuthis, Onychoteuthis, Watasenia, cuttlefish, Sepiolina, Oplophorus, Acanthophyra, Sergestes, Gnathophausia, Argyropelecus, Yarella, Diaphus, Gonadostomias and Neoscopelus.

36. The method of claim 29, wherein one or both compositions are administered by topical, enteric, local, parenteral, intracystal, intracutaneous, intravitreal, subcutaneous, intramuscular, or intravenous administration.

37. The method of claim 29, wherein one or both compositions are formulated for time release upon administration.

38. A method for in situ visualization of selected tissues, comprising:
(a) administering a first composition, comprising, in a pharmaceutically acceptable vehicle, a conjugate that comprises a targeted agent that is a luciferase or a luciferin, and a targeting agent, wherein the targeting agent specifically binds to a cell surface protein;
(b) performing surgery that exposes selected tissues; and
(c) administering a second composition, comprising, in a pharmaceutically acceptable vehicle, a luciferin or a luciferase and a spectral shifter, wherein the second composition comprises a luciferin and a spectral shifter if the targeted agent is a luciferase or it comprises a luciferase and a spectral shifter if the targeted agent is a luciferin,
whereby, if the selected tissue includes cells that express the cell surface protein light is produced in the exposed tissue.

39. The method of claim 38, wherein the conjugate comprises the following components: (targeting agent)$_n$, (L)$_q$ and (targeted agent)$_m$, wherein:
L is a linker;
the targeting agent is a protein or peptide that specifically binds to a cell surface protein;
at least one targeting agent is linked at any residue polypeptide via (L)$_q$ to at least one targeted agent;
m and n, which are selected independently, are at least 1;
q is 0 or more as long as the resulting conjugate binds to a cell surface protein on the targeted cells.

40. The method of claim 39, wherein L is selected from the group consisting of protease substrates, linkers that increase the flexibility of the conjugate, linkers that increase the solubility of the conjugate, linkers that increase the serum stability of the conjugate, photocleavable linkers and acid cleavable linkers.

41. The method of claim 39, wherein the targeting agent is a monoclonal antibody or a growth factor.

42. The method of claim 41, wherein the antibody is selected from the group consisting of FO23C5, A10, MN14 F(ab)2, MAb J28, MAb PA8-15, MAb C 50, MAb 19-9, MAb C 242, MAb AR-3, MAb DU-PAN- 2, MAb Ypan-1, MAb Span-1, MAb BW494, MAb MUSE 11, MAb 17-1A OC125, DF3, GA733MoAb, YH206MoAb and A78-G/A7.

43. The method of claim 41, wherein the antibody is humanized.

44. The method of claim 39, wherein the targeting agent is a tumor specific antibody.

45. The method of claim 39, wherein the conjugate is a chimeric protein produced by fusing a luciferase to a targeting agent.

46. The method of claim 39, wherein the conjugate is a non-covalent complex containing a targeting agent and a luciferin or luciferase.

47. The method of claim 39, wherein the targeting agent is a tumor specific antibody is selected from the group consisting of FO23C5, A10, MN14 F(ab)2, MAb J28, MAb PA8-15, MAb C 50, MAb 19-9, MAb C 242, MAb AR-3, MAb DU-PAN-2, MAb Ypan-1, MAb Span-1, MAb BW494, MAb MUSE 11, MAb 17-1A, OC125, DF3, GA733MoAb, YH206MoAb and A78-G/A7.

48. The method of claim 47, wherein the detecting method is non-invasive;
both compositions are administered systemically; and
resulting light can be detected by scanning or viewing the surface of the body.

49. The method of claim 39, wherein one or both compositions are administered by topical, local, enteric, parenteral, intracystal, intracutaneous, intravitreal, subcutaneous, intramuscular, or intravenous administration.

50. The method of claim 47, wherein one or both compositions are formulated for time release upon administration.

51. The method of claim 47, wherein the surgical procedure is a tumor excision or excision of specialty tissue.

52. The method of claim 39, wherein one or both compositions are formulated for time release upon administration.

53. The method of claim 38, wherein m and n, which are selected independently, are 1–6.

54. The method of claim 53, wherein q is 1, n is 1 and m is 1.

55. The method of claim 38, wherein the spectral shifter is selected from the group consisting of fluorochrome, green fluorescent proteins, red fluorescent proteins, and luciferins altered chemically or enzymatically to cause shifts in frequency of emission.

56. The method of claim 38, wherein the bioluminescence generating system is selected from the group consisting of those isolated from the ctenophores, coelenterases, mollusca, fish, ostracods, insects, bacteria, a crustacea, annelids, and earthworms.

57. The method of claim 38, wherein the bioluminescence generating system is selected from those isolated from: fireflies, Mnemiopsis, *Beroe ovata,* Aequorea, Obelia, Pelagia, Renilla, Pholas Aristostomias, Pachystomias, Poricthys, Cypridina, Aristostomias, Pachystomias, Malacosteus, Gonadostomias, Gaussia, Watensia, Halisturia, Vampire squid, Glyphus, Mycotophids, Vinciguerria, Howella, Florenciella, Ptilosarcus, Chaudiodus, Melanocostus, Sea Pens, Chiroteuthis, Eucleoteuthis, Onychoteuthis, Watasenia, cuttlefish, Sepiolina, Oplophorus, Acanthophyra, Sergestes, Gnathophausia, Argyropelecus, Yarella, Diaphus, Gonadostomias and Neoscopelus.

58. The method of claim 38, wherein the first composition is administered systemically.

59. The method of claim 38, wherein the first and second composition are administered systemically.

60. The method of claim 38, wherein the first composition is administered systemically prior to a surgical procedure, and, the second composition is applied topically during the surgical procedure.

61. The method of claim 38, wherein the first composition is administered systemically prior to a surgical procedure, and, the second composition is administered locally the surgical procedure.

62. The method of claim 38, wherein the first composition is administered locally during a surgical procedure, and, the second composition is applied topically or locally during the surgical procedure.

63. The method of claim 38, wherein one or both compositions are administered by topical, local, enteric, parenteral, intracystal, intracutaneous, intravitreal, subcutaneous, intramuscular, or intravenous administration.

64. The method of claim 38, further comprising detecting the emitted light.

65. The method of claim 38, further comprising detecting the emitted light.

66. The method of claim 38, wherein emitted light is detected by endoscopic localization.

67. The method of claim 38, wherein emitted light is detected by endoscopic localization.

68. A method of detecting of neoplasia or specialty tissue prior to surgical removal, comprising:

preoperatively administering to a mammal a targeting agent conjugated, directly or through a linker, to one or more component(s) of a bioluminescence generating system, wherein the components are a luciferase or luciferin;

waiting a predetermined period of time following administration to localize the conjugate in the neoplasia or specialty tissue;

administering a composition containing an effective amount of any remaining components or activators of the bioluminescence generating system, whereby the bioluminescence generating system produces light; and detecting neoplasia or specialty tissue that glows; wherein a compound that is a spectral shifter, whereby the spectrum of light generated by the bioluminescence generating system is shifted, is administered with the composition that contains the remaining components of the bioluminescence generating system.

69. The method of claim 68, further comprising surgically removing the glowing tissue.

70. The method of claim 68, wherein the targeting agent is selected from the group consisting of antibodies, methotrexate and growth factors.

71. The method of claim 68, wherein the targeting agent is an antibody or antigen binding fragment thereof.

72. The method of claim 71, wherein the targeting agent is a monoclonal antibody.

73. The method of claim 72, wherein the targeting agent is a humanized murine monoclonal antibody.

74. The method of claim 71, wherein the antibody is selected from the group consisting of FO23C5, A10, MN14 F(ab)2, MAb J28, MAb PA8-15, MAb C 50, MAb 19-9, MAb C 242, MAb AR-3, MAb DU-PAN-2, MAb Ypan-1, MAb Span-1, MAb BW494, MAb MUSE 11, MAb 17-1A, OC125, DF3, GA733MoAb, YH206MoAb and A78-G/A7.

75. The method of claim 68, wherein the targeting agent is conjugated to the targeted agent through a linker.

76. The method of claim 68, wherein the component of the bioluminescence generating system is a luciferase.

77. The method of claim 68, wherein the bioluminescence generating system is selected from the group consisting of those isolated from the ctenophores, coelenterases, mollusca, fish, ostracods, insects, bacteria, a crustacea, annelids, and earthworms.

78. The method of claim 77, wherein the luciferase is selected from among Aequorea, Vargula, Renilla, Obelin, Porichthys, Odontosyllis, Aristostomias, Pachystomias, firefly bacterial systems and *Gaussia luciferases.*

79. The method of claim 68, wherein the neoplasia is selected from the group consisting of melanoma, lymphoma, osteosarcoma, glioma, leukemia, teratocarcinoma, adenocarcinoma, colorectal carcinoma, primary hepatoma, lung carcinoma, mucinous cystadenocarcinoma, hepatocellular carcinoma, medulloblastoma, pancarcinoma, squamous tumors, neuroblastoma, gastrointestinal carcinoma, medullary thyroid carcinoma, breast tumors, brain tumors, ovarian tumors, cervical tumors, prostate tumors, bladder tumors and meningioma.

80. The method of claim 68, wherein the specialty tissue is selected from among ligaments, tendons, endometriotic tissue and fetal tissue of an ectopic pregnancy.

81. The method of claim 68, wherein a photosensitizing composition is administered prior to administering the second composition, whereby, upon reaction of luciferin with the luciferase at the targeted tissue to produce a glow, some or all of the glowing tissue is destroyed.

82. A pharmaceutical composition formulated as spray, foam or aerosol comprising one or more components of a bioluminescence generating system selected from the group consisting of luciferins and luciferases.

83. The composition of claim 82, wherein at least one of the components is a luciferin or a luciferase and the concentration is between about 0.1 mg/l and 10 mg/l.

84. The composition of claim 83, wherein the concentration is between about 1 mg/l and 5 mg/l.

85. A method of detecting neoplasia or specialty tissue, comprising:
   a) preoperatively administering to a mammal an effective amount of a composition wherein:
      the composition comprises, in a pharmaceutically acceptable vehicle, a conjugate that comprises a targeted agent that is a component of a bioluminescence generating system, and a targeting agent;
      a bioluminescence generating system comprises a luciferase as one component and a luciferin as another component;
      the conjugate binds to a cell surface receptor, the targeted agent is a luciferase or luciferin, the targeting agent specifically binds to a cell surface protein;
   b) waiting a predetermined period of time following administration to allow the targeting agent to preferentially localize in the neoplasia or specialty tissue;
   c) exposing a predetermined area surrounding the neoplasia or specialty tissue using a surgical procedure;
   d) contacting the predetermined area with a composition containing any remaining components or activators of the bioluminescence generating system, whereby any neoplasia or specialty tissue in the exposed area glows; and
   e) detecting the glowing tissue.

86. The method of claim 85, further comprising excising the glowing tissue.

87. A method of photodynarnic therapy, comprising:
   administering to a mammal an effective amount of a photosensitizing drug;
   administering composition containing a conjugate comprising a component of a bioluminescence generating system, wherein the first component is a luciferin or luciferase; and
   then administering additional components of the system, wherein light generated by the bioluminescence generating system activates the drug.

88. A method for in vivo labeling of selected tissues, comprising:
   contacting the tissue with a conjugate comprising a first component of a bioluminescence generating system, wherein the first component is a luciferin or luciferase;
   then contacting the tissue with the remaining components of the system to generate light; wherein:
   the bioluminescence generating system further comprises a compound that shifts the spectrum of the light generated by the bioluminescence generating reaction; and
   contacting is effected in vivo.

89. The method of claim 88, wherein the compound shifts the spectrum of the generated light towards the red end of the spectrum.

* * * * *